(12) United States Patent
Safe

(10) Patent No.: US 12,264,150 B2
(45) Date of Patent: Apr. 1, 2025

(54) NR4A1 LIGANDS, PHARMACEUTICAL COMPOSITIONS, AND RELATED METHODS OF USE

(71) Applicant: The Texas A&M University System, College Station, TX (US)

(72) Inventor: Stephen Safe, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 17/510,904

(22) Filed: Oct. 26, 2021

(65) Prior Publication Data

US 2022/0332703 A1  Oct. 20, 2022

Related U.S. Application Data

(63) Continuation of application No. 16/638,101, filed as application No. PCT/US2018/046115 on Aug. 9, 2018, now abandoned.

(60) Provisional application No. 62/543,761, filed on Aug. 10, 2017.

(51) Int. Cl.
*C07D 403/06* (2006.01)
*A61P 3/10* (2006.01)
*A61P 35/00* (2006.01)

(52) U.S. Cl.
CPC .............. *C07D 403/06* (2013.01); *A61P 3/10* (2018.01); *A61P 35/00* (2018.01)

(58) Field of Classification Search
CPC .................................................... C07D 403/06
See application file for complete search history.

(56) References Cited

U.S. PATENT DOCUMENTS

| | | | |
|---|---|---|---|
| 2001/0047029 | A1 | 11/2001 | Handelsman et al. |
| 2003/0130335 | A1 | 7/2003 | Mjalli et al. |
| 2006/0084694 | A1 | 4/2006 | Safe et al. |
| 2010/0087504 | A1 | 4/2010 | Tjalkens |
| 2016/0037773 | A1 | 2/2016 | Qian et al. |
| 2016/0303081 | A1 | 10/2016 | Safe et al. |
| 2017/0009272 | A1 | 1/2017 | Yousuf et al. |
| 2018/0312568 | A1 | 11/2018 | Hedrick et al. |
| 2018/0320170 | A1 | 11/2018 | Konieczka et al. |
| 2020/0239448 | A1 | 7/2020 | Safe et al. |
| 2021/0401823 | A1 | 12/2021 | Sacher et al. |
| 2022/0265606 | A1 | 8/2022 | Safe et al. |
| 2023/0113363 | A1 | 4/2023 | Safe et al. |

FOREIGN PATENT DOCUMENTS

| | | |
|---|---|---|
| CA | 3072456 A1 | 2/2019 |
| CN | 1268134 A | 9/2000 |
| CN | 10545237 A | 4/2016 |
| CN | 110573146 A | 12/2019 |
| EP | 0887348 A1 | 12/1998 |
| JP | 2002-507206 A | 3/2002 |
| WO | 99/00381 A1 | 1/1999 |
| WO | 2006023891 A2 | 3/2006 |
| WO | 2006/133943 A1 | 12/2006 |
| WO | 2012/065139 A2 | 5/2012 |
| WO | 2014002613 A1 | 2/2014 |
| WO | 2019/032902 A1 | 2/2019 |
| WO | 2021/022220 A2 | 2/2021 |
| WO | 02/080906 A1 | 10/2022 |

OTHER PUBLICATIONS

Rekha, et al. (abstract) Journal of Industrial and Engineering Chemistry (Amsterdam, Netherlands) (2013), 19 (1), 337-346. Accession No. 2012:1769704 retrieved from CAPLUS.*
Ji, et al. Synlett (2003), (13), 2077-2079 (abstract); Accession No. 2003:865551, retrieved from STN.*
Lin, et al. CN 101979631 (abstract); Feb. 23, 2011; Accession No. 2011:230668, retrieved from STN.*
Zhang, et al. Synthetic Communications (2011), 41(16), 2446-2454 (abstract); Accession No. 2011:751510, retrieved from STN.*
Khan, et al. Bioorganic& Medicinal Chemistry Letters (2014), 24(7), 1825-1829 (abstract); Accession No. 2014:366830, retrieved from STN.*
Sarva, et al. Chinese Chemical Letters (2016), 27(1), 16-20 (abstract); Accession No. 2015:1434534; retrieved from STN.*
Chakrabarty, et al. Heterocycles (2006), 68(8), 1659-1668 (abstract); Accession No. 2006:881513; retrieved from STN.*
Zhungietu, et al. Khimiya Geterotsiklicheskikh Soedinenii (1973), (1), 40-4 (abstract); Accession No. 1973:111201; retrieved from STN.*
Bharate, et al. European Journal of Medicinal Chemistry (2013), 63, 435-443 (abstract); Accesion No. 2013:892485; retrieved from STN.*
Khazaei, et al. Journal of Chemical Research (2013), 37(1), 617-619. Accession No. 2014:252703, retrieved from STN.*
Kim, et al. Bulletin of the Korean Chemical Society (2009), 30(1), 197-200. Accession No. 2009:272800, retrieved from STN.*
Nikoofar, et al. Arabian Journal of Chemistry (2019), 12(8), 3776-3784. Accession No. 2016:242202, retrieved from STN.*
Tabatabaeian, et al. Canadian Journal of Chemistry (2006), 84(11), 1541-1545. Accession No. 2006:1261579, retrieved from STN.*
International Search Report mailed Nov. 26, 2018, for International Application No. PCT/US2018/046115. (5 pages).
Written Opinion mailed Nov. 26, 2018, for International Application No. PCT/US2018/046115. (5 pages).
Chakrabarty et al., Document No. 145:438485, retrieved from CAPLUS, 2006.
Zhang et al., Document No. 143:347015, retrieved from CAPLUS, 2005.

(Continued)

*Primary Examiner* — Shawquia Jackson
(74) *Attorney, Agent, or Firm* — CHRISTENSEN O'CONNOR JOHNSON KINDNESS PLLC

(57) ABSTRACT

NR4A1 ligands, pharmaceutical compositions including the NR4A1 ligands, and related methods of use are described. Methods of treating a disease or condition in an individual treatable by modulation of NR4A1 activity, comprising administering to the individual a therapeutically effective amount of a compound or a pharmaceutical composition described herein.

37 Claims, 42 Drawing Sheets

(56) References Cited

OTHER PUBLICATIONS

Palaniappan et al., Document No. 143:327199, retrieved from CAPLUS, 2005.
Rani et al., Document No. 156:533580, retrieved from CAPLUS, 2012.
Ghorbani-Vaghei et al, Document No. 153:358813, retrieved from CAPLUS, 2010.
Lala, P.K. and Orucevic, A., "Role of nitric oxide in tumor progression: Lessons from experimental tumors," Cancer and Metastasis Reviews, 17(1):91-106, 1998.
Golub, T.R. et al., "Molecular Classification of Cancer: Class Discovery and Class Prediction by Gene Expression Monitoring," Science, 286:531-537, Oct. 15, 1999.
"Cancer" [online: MedlinePlus], retrieved from the Internet <http://www.nlm.nih.gov/medlineplus/cancer.html> [retrieved on Jul. 6, 2007], 10 pages.
Naidu, Kalla Reddi Mohan; Khalivulla, Shaik Ibrahim; Rasheed, Syed; Fakurazi, Sharida; Arulselvan, Palanisamy; Lasekan, Ola; Abas, Faridah, Synthesis of bisindolylmethanes and their cytotoxicity properties, International Journal of Molecular Science, 2013, 14, 1843-1853.
Sharma, Deepak K.; Rah, Bilal; Lambu, Mallikharjuna R.; Hussain, Altaf; Yousuf, Syed K.; Tripathi, Anil K.; Singh, Baldev; Jamwal, Gayatri; Ahmed, Zabeer; Chanauria, Nayan; Nargotra, Amit; Goswami, Anindya; Mukherjee, Debaraj, Design and synthesis of novel N, N'-glycoside derivatives of 3, 3∝-diindolylmethanes as potential antiproliferative agents, MedChem Comm, 2012, 3(9), 1082-1091.
Velasco-Bejarano, Benjamin; Sanchez-Torres, Luvia Enid; Garcia-Estrada, Jose Guadalupe; Miranda-Ruvalcaba, Rene; Alvarez-Toledano, Cecilio; Penieres-Carrillo, Guillermo, Diindolylmethane derivatives as apoptosis inductors in L5178y cells, Journal of the Mexican Chemical Societ., 2008, 52(3), 224-228.
Nasreen, Aayesha; Varala, Ravi; Rao, Kulakarni Sripad, A green protocol for the synthesis of bis(indolyl)methanes catalyzed by succinic acid under microwave irradiation, Organic Communications, 2017, 10(2), 104-113.
Database Registry, 2006, RN 893250-92-5, 893250-47-0, 892218-53-0, 694453-96-8, 694444-38-7, 694442-88-1, Retrieved from STN international [online]; retrieved on Aug. 2, 2022.
Zhan, Yan-yan, et al., The orphan nuclear receptor Nur77 regulates LKB1 localization and activate AMPK, Nature Chemical Biology, 2012, 8, 897-904.
English Translation of Japanese Notice of Reasons for Rejection mailed on Aug. 22, 2022, issued in corresponding Japanese Application No. 2020-507693, filed on Aug. 9, 2018, 7 pages.
Notice of Deficiencies dated Mar. 16, 2022 in corresponding Israeli Patent Application No. 272571, 6 pages.
Das Pranab J et al, "Synthesis of aryl/alkyl(2,2'-bis-3-methylindolyl)methanes and aryl(3,3'-bis indolyl)methanes promoted by secondary amine based ionic liquids and microwave irradiation", Tetrahedron Letters, Jun. 28, 2012, vol. 53, No. 35, doi:10.1016/J.TETLET.2012.06.106, ISSN 0040-4039, pp. 4718-4720.
Scientific Exchange Inc., Registry, Chemical Abstracts Service, Columbus, Ohio, US, (Jul. 16, 2006), Database accession No. 893250-47-0.
ChemBridge Corp, Registry, Chemical Abstracts Service, Columbus, Ohio, US, (Jun. 17, 2004), Database accession No. 694442-88-1.
Kamal Ahmed et al, "Synthesis, anticancer activity and apoptosis inducing ability of bisindole linked pyrrolo[2,1-c][1,4]benzodiazepine conjugates", Biorganic & Medicinal Chemistry Letters, Elsevier, Amsterdam , NL, Oct. 31, 2011, vol. 22, No. 1, doi:10.1016/J.BMCL.2011.10.080, ISSN 0960-894X, pp. 571-578.
Joshi R S et al, "Ultrasound assisted green synthesis of bis(indol-3-yl)methanes catalyzed by 1-hexenesulphonic acid sodium salt", Ultrasonics: Sonochemistry, Butterworth-Heinemann, GB, vol. 17, No. 2, doi:10.1016/J.ULTSONCH.2009.08.015, ISSN 1350-4177, Aug. 29, 2009, pp. 298-300.
Registry, Chemical Abstracts Service, Columbus, Ohio, US, (JUn. 17, 2004), Database accession No. 694444-38-7.
Decision of Rejection issued Mar. 22, 2023 for CN Patent App. No. 201880065793.1 filed Aug. 9, 2018.
Ghorbani-Vaghei, R., et al., "Facile and Mild Synthesis of bis(3-Indolyl)methanes," Organic Preparations and Procedures International, 2010, 42(2)., 175-182.
Decision of Rejection mailed Mar. 20, 2023 for JP Patent App. No. 2020-507693 filed Aug. 9, 2018.
International Search Report mailed on May 6, 2021, issued in corresponding International Application No. PCT/US2021/19402, filed on Feb. 24, 2021, 3 pages.
Written Opinion of the International Searching Authority mailed on May 6, 2021, issued in corresponding International Application No. PCT/US2021/19402, filed on Feb. 24, 2021, 4 pages.
Mohankumar, Kumaravel et al.; "Nuclear Receptor 4A1 (NR4A1) Antagonists Induce ROSdependent Inhibition of mTOR Signaling in Endometrial Cancer"; Gynecologic Oncology; vol. 154(1); 2019; 19 paqes.
Lee, Syng-Ook et al.; "Diindolylmethane Analogs Bind NR4A1 and Are NR4A1 Antagonists in Colon Cancer Cells"; Molecular Endocrinology; vol. 28(10); Oct. 2014; pp. 1729-1739.
Mohankumar, Kumaravel et al.; "Bis-Indole-Derived NR4A1 Ligands and Metformin Exhibit NR4A1-Dependent Glucose Metabolism and Uptake in C2C12 Cells"; Endocrinology; vol. 159(5); May 2018; 24 paqes.
Lee, Syng-Ook et al.; "Targeting NR4A1 (TR3) in Cancer Cells and Tumors"; Expert Opinion on Therapeutic Targets; vol. 15(2); Feb. 2011; 20 paqes.
Examination Report mailed Nov. 8, 2022, issued in corresponding Australian Application No. 2018313925, filed Aug. 9, 2018, 10 pages.
Rani, V. Jhansi, K. Veena Vani, and C. Venkata Rao. "PEG-SO3H as a Catalyst for the Preparation of Bis-Indolyl and Tris-Indolyl Methanes in Aqueous Media." Synthetic Communications 42.14 (2012): 2048-2057. CAS RN 692290-53-2, Retrieved from STNext [online) on May 22, 2021.
Challa, Chandrasekhar, et al. "Expedient synthesis of indolo [2, 3-b] quinolines, chromeno [2, 3-b] indoles, and 3-alkenyl-oxindoles from 3, 3'-diindolylmethanes and evaluation of their antibiotic activity against methicillin-resistant Staphylococcus aureus." ACS omega 2.8 (2017): 5187-5195.
Slam, Md Ataul, and Tahir S. Pillay. "Structural requirements for potential HIV-integrase inhibitors identified using pharmacophore-based virtual screening and molecular dynamics studies." Molecular Biosystems 12.3 (2016): 982-993.
Sarva, Santhisudha, et al. "Synthesis, antibacterial and anti-inflammatory activity of bis (indolyl) methanes." Chinese Chemical Letters (2015).
Khan, Khalid Mohammed, et al. "Evaluation of bisindole as potent β-glucuronidase inhibitors: Synthesis and in silico based studies." Bioorganic & medicinal chemistry letters 24.7 (2014): 1825-1829.
Substances/CAS RN 315235-11-1, STN Entry Date Jan. 19, 2001, Retrieved from SciFinder [online) on Dec. 6, 2022.
Substances/CAS RNs 315235-11-1 (Jan. 19, 2001), 486994-88-1 (Feb. 7, 2003), 486442-81-3 (Feb. 6, 2003), 510765-97-6 (May 5, 2003), 898679-19-1 (Aug. 4, 2006), 893251-07-5 (Jul. 16, 2006), and 486994-82-5 (Feb. 7, 2003), Retrieved from SciFinder [online) on Dec. 6, 2022.
Substances/CAS RNs 496839-88-4 (Mar. 4, 2003), 666818-76-4 (Mar. 24, 2004), 666818-70-8 (Mar. 24, 2004), 694453-96-8 (Jun. 17, 2004), 737769-31-2 (Sep. 2, 2004), 666818-67-3 (Mar. 24, 2004), 892225-57-9 (Jul. 12, 2006), and 693832-30-3 (Jun. 16, 2004), Retrieved from SciFinder [online) on Dec. 6, 2022.
Substances/CAS RNs 693827-98-4 (Jun. 16, 2004), 694447-96-6 (Jun. 17, 2004), 694447-49-9 (Jun. 17, 2004), and 893250-85-6 (Jul. 16, 2006), Retrieved from SciFinder [online) on Dec. 6, 2022.
Zoifigol, M.A., et al., "The first urea-based ionic liquid-stabilized magnetic nanoparticles: an efficient catalyst for the synthesis of bis(indolyl)methanes and pyrano[2,3-d]pyrimidinone derivatives," Applied Organometallic Chemistry, Longman Group UK, Ltd, Hoboken, USA, vol. 30, No. 5, Feb. 4, 2016, pp. 273-281.

(56) References Cited

OTHER PUBLICATIONS

Khazaei, A., et al., "Iconic Liquid Tributyl (Carboxymethyl) Phosphonium Bromide as an efficient Catalyst for the Synthesis of bis(indolyl) Methandes under Solvent-Free Conditions," Journal of Chemcial Research, vol. 37, No. 10, Oct. 1, 2013, pp. 617-619.
Shirini, F., et al., "Succinimide-N-sulfonic acid catalyzed synthesis of bis(indolyl)methane and courmarin derivatives under mild conditons," Chinese Journal of Catalysis, vol. 34, No. 10, Oct. 1, 2013, pp. 1890-1896.
Communication pursuant to Article 94(3) EPC for European Application No. 18843943.3 dated Feb. 13, 2023.
Australian Examination Report No. 3 for AU Application No. 2018313925 dated Mar. 2, 2023.
First Chinese Office Action mailed on Sep. 26, 2022, issued in corresponding Chinese Application No. 2018800657931, filed Aug. 9, 2018, and its English translation thereof, 13 pages.
Examination report No. 4 for Australian patent application No. 2018313925, dated May 8, 2023.
Kumar, K.S., et al. "Micelle promoted synthesis of bis-(indolyl)methanes." Letters in Organic Chemistry, 2012, 9(4), 294-299.
First Office Action dated May 30, 2023 for Chinese patent application No. 202080068950.1 filed on Jul. 31, 2020.
Li, Xi et al. "Structure-dependent activation of gene expression by bis-indole and quinoline-derived activators of nuclear receptor 4A2." Chemical Biology & Drug Design, vol. 94, Issue 4, pp. 1711-1720, published May 18, 2019.
Australian Examination Report mailed on Nov. 30, 2023, issued in Australian Application No. 2023203349, filed on Jul. 31, 2020, 3 pages.
Extended European Search Report mailed on Jul. 21, 2023, issued in European Application No. 20846800.9, filed on Jul. 31, 2020, 11 pages.
First Chinese Office Action mailed on Sep. 5, 2023, issued in Chinese Application No. 202180030854.0, filed on Aug. 23, 2022, 13 pages.
Second Chinese Office Action mailed om Dec. 29, 2023, issued in Chinese Application No. 202080068950.1, filed on Jul. 31, 2020, 8 pages.
Lee, S.O. et al., "Diindolylmethane Analogs Bind NR4A 1 and Are NR4A 1 Antagonists in Colon Cancer Cells," Mol Endocrinol. Oct. 2014, 28(10):1729-1739.
Mattiazzi, J. et al. "Incorporation of 3,3'-Diindolylmethane into Nanocapsules Improves Its Photostability, Radical Scavenging Capacity, and Cytotoxicity Against Glioma Cells," AAPS PharmSciTech, (2019) 20:49, pp. 1-11.
Mohankumar, K. et al., "Nuclear Receptor 4A1 (NR4A1) Antagonists Induce ROSdependent Inhibition of mTOR Signaling in Endometrial Cancer," Gynecol Oneal. Jul. 2019; I 54(1): 218--227. doi: 10.1016/j.ygyno.20! 9 04.678.
Morales-Prieto, D. M. et al., "Comparison of dienogest effects upon ,'-diindolylmethane supplementation in models of endometriosis and clinical cases," Science Direct: Reproductive Biology, vol. 18, Issue 3, Sep. 2018, pp. 252-258.
Rahimi, M. et al., "3,3'-Diindolylmethane (DIM) inhibits the growth and invasion of drug-resistant human cancer cells expressing EGFR mutants," Elsevier: Cancer Letters 295 (2010) 59-68.
Canadian Office Action mailed on Feb. 19, 2024, issued in Canadian Application No. 3,173,724, filed on Feb. 24, 2021; 3 pages.
Chinese Decision on Rejection mailed on Jun. 17, 2024, issued in Chinese Application No. 202080068950.1, filed on Jul. 31, 2020; 10 pages.
Japanese Notice of Reasons for Rejection mailed on Jul. 30, 2024, issued in Japanese Application No. 2022-506375, filed on Jul. 31, 2020; 11 pages.
Decision of Rejection mailed on Mar. 20, 2023, issued in Japanese Application No. 2023-118472, filed on Aug. 9, 2018; 6 pages.
Canadian Office Action mailed on Feb. 19, 2024, issued in Canadian Application No. 3,072,456, filed on Aug. 9, 2018; 6 pages.
European Supplementary Search Report mailed on Apr. 2, 2024, issued in European Application No. 21760941.1, filed on Feb. 24, 2021; 12 pages.
Liu, et al., "Overexpression of TGF-B enhances the migration and invasive ability of ectopic endometrial cells via ERK/MAPK signaling pathway," Experimental and Therapeutic Medicine 17: 4457-4464, 2019.
Palumbo-Zerr, K. et al., "Orphan nuclear receptor NR4A1 regulates transforming growth factor-B signaling and fibrosis," Nature Medicine, vol. 21, No. 2, Feb. 2015, pp. 150-160.
Safe, S. et al., "Orphan nuclear receptor 4A1 (NR4A1) and novel ligands," Essays in Biochemistry (2021) 65; 877-886. <https://doi.Org/10.1042/EBC20200164>.

\* cited by examiner

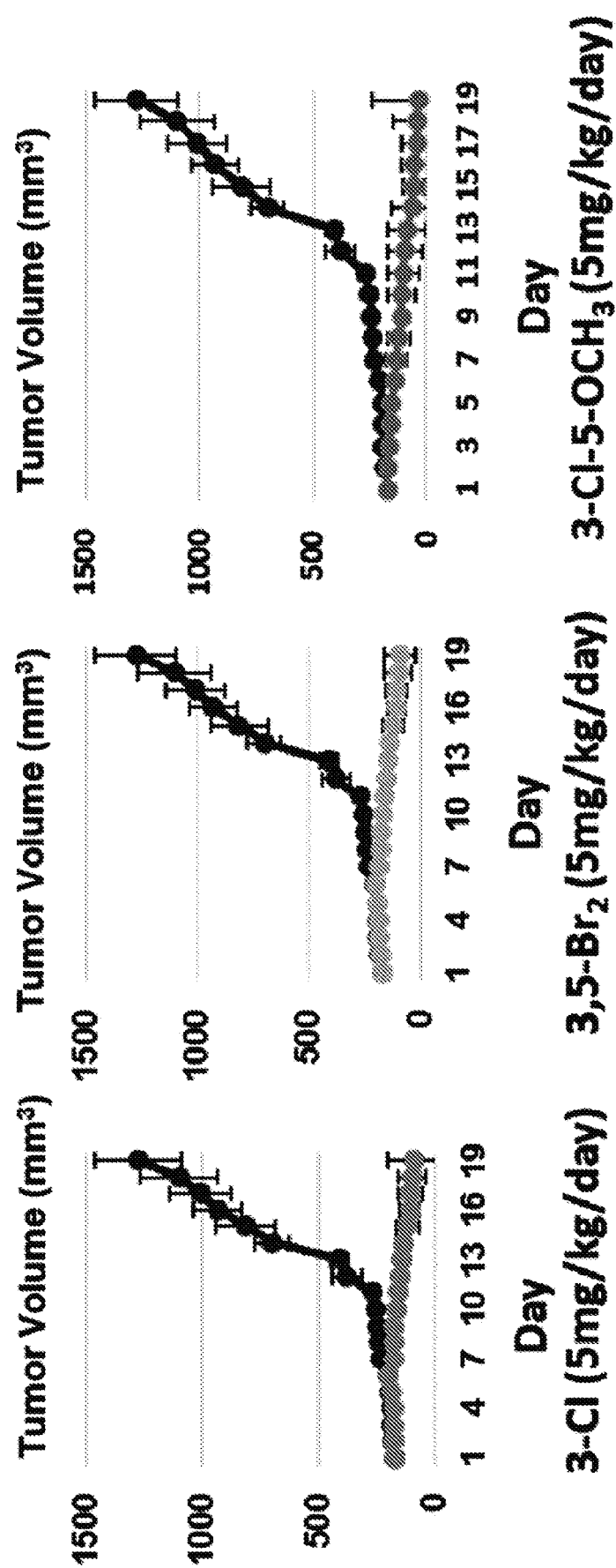

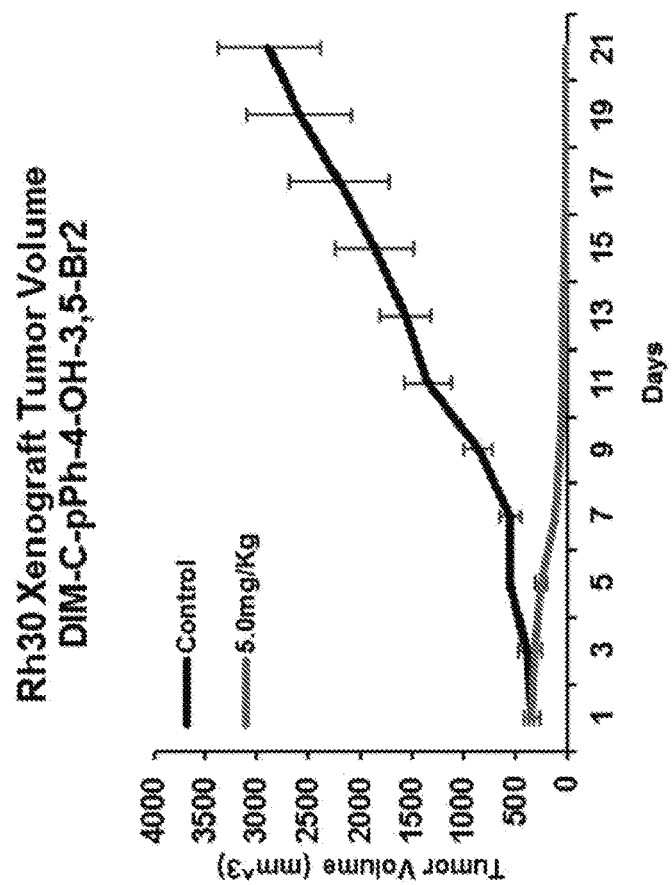
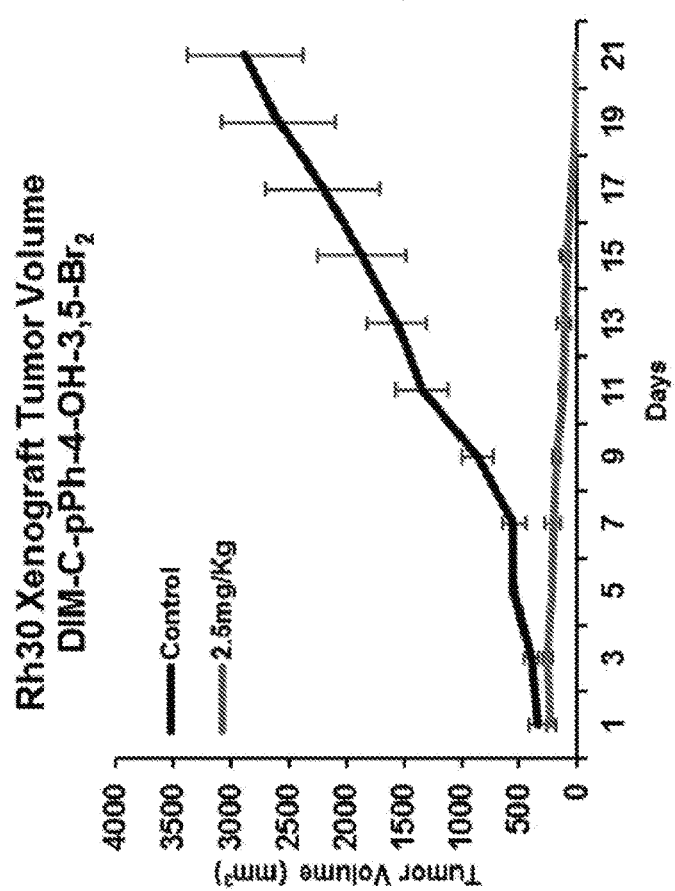
FIG. 24A
FIG. 24B

NR4A1 LIGANDS, PHARMACEUTICAL COMPOSITIONS, AND RELATED METHODS OF USE

CROSS-REFERENCE TO RELATED APPLICATION

This application is a Continuation of U.S. patent application Ser. No. 16/638,101, filed Feb. 10, 2020, which is a U.S. national stage entry of International Patent Application No. PCT/US2018/046115, filed Aug. 9, 2018, which claims the benefit of U.S. Provisional Patent Application No. 62/543,761, filed on Aug. 10, 2017, the contents of each of which are incorporated herein by reference in their entireties.

BACKGROUND

Nuclear Receptor Subfamily 4 Group A Member 1 (NR4A1) is overexpressed in colon, pancreatic, breast (estrogen receptor positive and negative), and lung tumors; in breast, colon, and lung tumor patients, high expression of NR4A1 predicts decreased survival. The functional activity of NR4A1 in cancer has been extensively investigated in cancer cell lines by either knockdown or overexpression, and results have shown that in lung, melanoma, lymphoma, pancreatic, colon, breast, kidney, cervical, ovarian, and gastric cancer cell lines, NR4A1 regulates one or more of cancer cell proliferation, survival, cell cycle progression, migration and invasion (FIG. 1). Studies have identified β1- and other integrins as NR4A1-regulated genes. Studies also demonstrate that NR4A1 is overexpressed in tumors from rhabdomyosarcoma (RMS) patients and this receptor regulates the pro-oncogenic pathways in RMS cells as illustrated in FIG. 1. The pro-oncogenic functions of NR4A1 include the regulation of several genes that are themselves individual drug targets, including integrins, survivin, EGFR, and other receptor tyrosine kinases.

This suggests that development of an NR4A1 antagonist would represent a unique chemotherapy that simultaneously targets multiple pro-oncogenic pathways associated with the growth, survival, and migration/invasion of solid tumors. Studies initially showed that several 1,1-bis(3'-indolyl)-1-(p-substituted phenyl)methane (C-DIM) compounds inactivated NR4A1, and subsequent studies identified DIM-C-pPhOH and other p-substituted phenyl analogs as NR4A1 ligands. DIM-C-pPhOH and related compounds block the pro-oncogenic pathways outlined in FIG. 1 at concentrations of 10-20 µM in cell culture and partially inhibit tumor growth at doses of 30-40 mg/kg/d. DIM-C-pPhOH has a high binding affinity for NR4A1 ($K_o$–0.100 µM) but exhibits a short in vivo half-life.

As above, studies have focused on the development of NR4A1 ligands that bind NR4A1 and act as antagonists (inverse agonists). Research by one or more of the present inventors has relied upon RNA interference (RNAi) to knockdown NR4A1 and molecular/biochemical studies to determine the effects of receptor knockdown on cell functions and associated pathways required for cell function. Initial studies showed that knockdown of NR4A1 resulted in decreased pancreatic cancer cell growth and induction of apoptosis; this has also been observed in rhabdomyosarcoma, lung, breast, kidney and colon cancer cell lines. Mechanistic studies demonstrate that NR4A1 acts as a cofactor to activate pro-survival (survivin and bcl2) and growth promoting (EGFR and other receptor tyrosine kinases) genes by interacting with Sp transcription factors bound to the proximal GC-rich regions of these genes. NR4A1 coupled with other cofactors (e.g. p300) activate and regulate expression of these genes.

It has been demonstrated that among a series of C-DIM analogs, the p-hydroxyphenyl analog (DIM-C-pPhOH; CDIM8) not only binds to NR4A1 but acts as an antagonist. Thus, DIM-C-pPhOH inhibits cancer cell growth and survival, and inhibits expression of survivin, EGFR, and other NR4A1/Sp-regulated genes. Knockdown of NR4A1 by RNAi also inhibits mTOR signaling through p53-dependent and -independent activation of sestrin; similar results are observed for DIM-C-pPhOH and other NR4A1/C-DIM antagonists in multiple cancer cell lines. NR4A1 also plays a critical role in maintaining low oxidant stress in cancer cell lines by regulating expression of isocitrate dehydrogenase 1 (IDH1) and thioredoxin domain containing 5 (TXNDC5). Knockdown of NR4A1, or treatment with DIM-C-pPhOH and other NR4A1 antagonists, decreases expression of IDH1 and TXNDC6, resulting in the induction of reactive oxygen species (ROS), ROS-dependent endoplasmic reticulum stress, and cell death in many cancer cell lines (FIG. 1). Recent studies showed that NR4A1 plays a key role in cancer cell migration/invasion and this is due to NR4A1/Sp-mediated regulation of β1-integrin, a pro-invasion gene. NR4A1 knockdown or treatment with DIM-C-pPhOH or other NR4A1 antagonists decreased cancer cell migration and down-regulated β1-integrin and other integrins (FIG. 1).

These studies confirmed that NR4A1 is pro-oncogenic in solid tumors, and DIM-C-pPhOH and other C-DIMs have been characterized as NR4A1 antagonists in cancer cell lines. The first generation C-DIM compounds all contain p-substituted phenyl moieties, and DIM-C-pPhOH (p-hydroxyphenyl) was characterized as a high affinity ligand that primarily exhibits NR4A1 antagonist activity in cancer cell lines with minimal receptor-independent activities such as mitochondrial toxicity; however, the activity of DIM-C-pPhOH and related compounds as tumor growth inhibitors in vivo is in the –30 mg/kg/d range, and the in vivo half-life is very short.

The present disclosure seeks to fulfill these needs and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In an aspect, the present disclosure provides a Nuclear Receptor Subfamily 4 Group A Member 1 (NR4A1) ligand. In an embodiment, the ligand is a compound of the formula:

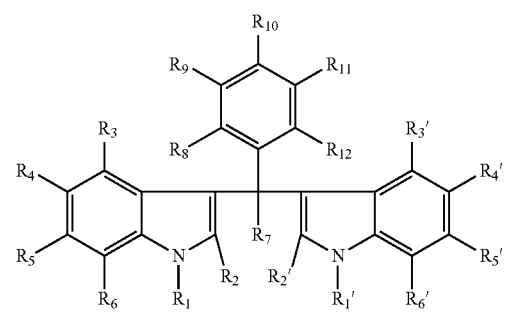

or a salt thereof,
wherein,
$R_1$, $R_2$, $R_1'$, and $R_2'$ are each independently selected from the group consisting of hydrogen, a linear alkyl group containing one to about ten carbon atoms, and a branched alkyl group containing one to about ten carbon atoms;

$R_3$, $R_4$, $R_5$, $R_6$, $R_3'$, $R_4'$, $R_5'$, and $R_6'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

$R_7$ is selected from the group consisting of hydrogen, a linear alkyl group containing one to about ten carbon atoms, a branched alkyl group containing one to about ten carbon atoms, a cycloalkyl group containing one to about ten carbon atoms, and an aryl group;

$R_8$, $R_9$, $R_{10}$, $R_{11}$, and $R_{12}$ are independently selected from the group consisting of H, a halogen, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a hydroxyl group, and a haloalkoxy group containing one to about ten carbon atoms;

wherein at least one of $R_8$, $R_9$, $R_{10}$, $R_{11}$, and $R_{12}$ is OH, and wherein when $R_{10}$ is OH at least one of $R_8$, $R_9$, $R_{11}$, and $R_{12}$ is not hydrogen.

In another aspect, the present disclosure provides pharmaceutical composition, comprising a therapeutically effective amount of a compound described herein and a pharmaceutically acceptable carrier.

In another aspect, the present disclosure provides method of treating a disease or condition in an individual treatable by modulation of NR4A1 activity, comprising administering to the individual a therapeutically effective amount of a compound or a pharmaceutical composition described herein.

In another aspect, the present disclosure provides method of modulating NR4A1 activity in a cell, comprising administering to the cell a compound or a pharmaceutical composition described herein.

DESCRIPTION OF THE DRAWINGS

The foregoing aspects and many of the attendant advantages of the claimed disclosure will become more readily appreciated as the same become better understood by reference to the following detailed description, when taken in conjunction with the accompanying drawings, wherein:

FIGS. 23A-23D graphically illustrate xenograft breast tumor volume (A-C) and mass (D) in mice treated with C-DIM analogs, according to embodiments of the present disclosure;

FIGS. 24A-24D graphically illustrate tumor volume of RMS xenograft tumor in mice treated with 3,5-dibromo-4-hydroxy C-DIM compound, according to embodiments of the present disclosure;

DETAILED DESCRIPTION

Figure 1:
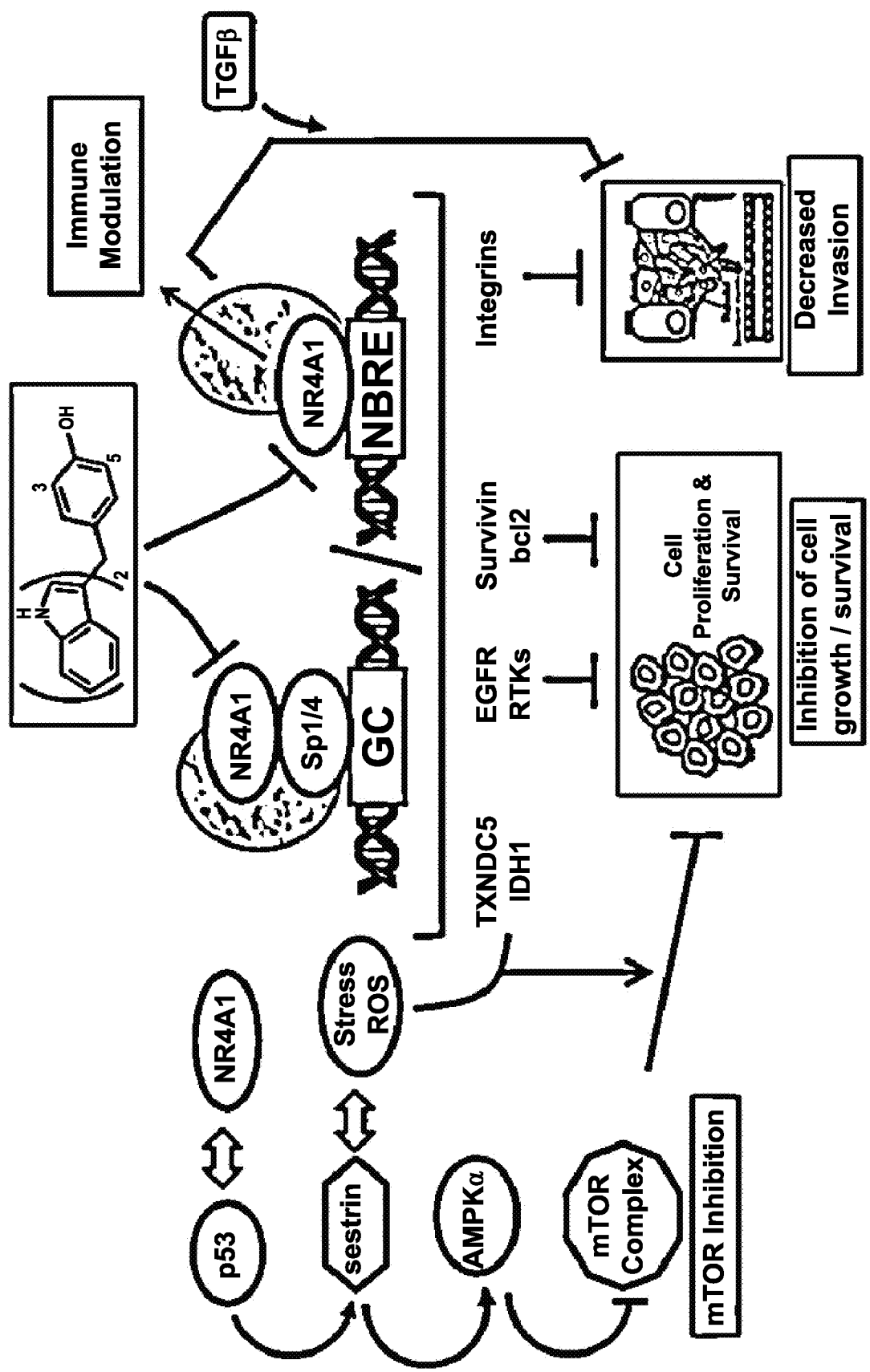
FIG. 1 schematically illustrates inhibition of Nuclear Receptor Subfamily 4 Group A Member 1 (NR4A1) as 1,1-bis(3'-indolyl)-1-(p-substituted phenyl)methane (C-DIM)/NR4A1 ligand attenuates NR4A1-dependent growth and survival pathways.
Figure 2:
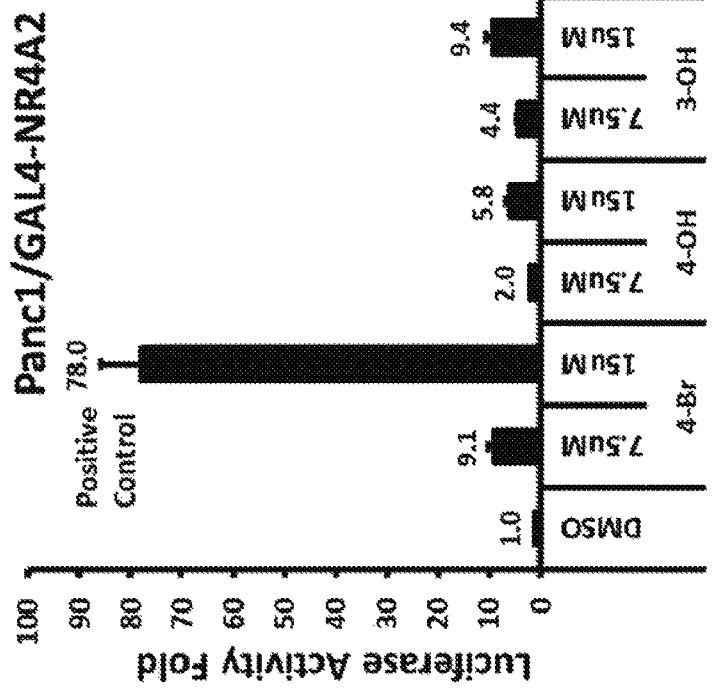
FIG. 2 graphically illustrates luciferase activity in Panc1 cells transfected with GAL4-NR4A1 and GAL4-NR4A2 and UAS-Luc (GAL4-binding luciferase construct) treated with 4-, 3- and 2-hydroxy C-DIM analogs according to embodiments of the present disclosure.
Figure 2:
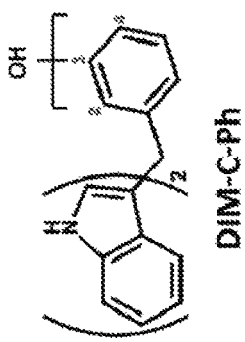
Figure 2:
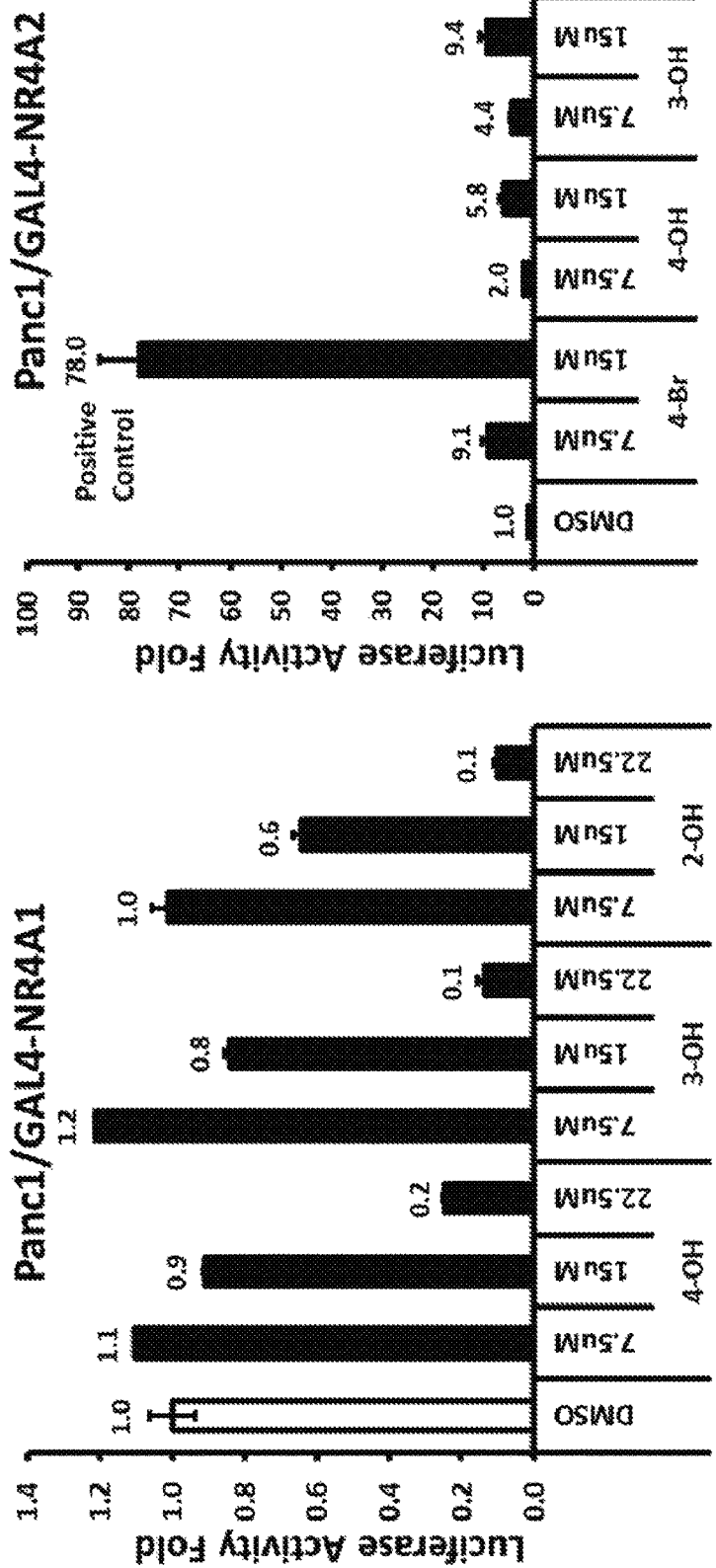

The present invention provides Nuclear Receptor Subfamily 4 Group A Member 1 (NR4A ligands, pharmaceutical compositions including a therapeutically effective amount of such NR4A1 ligands, and related methods of use.

Nr4A1 Ligands

In an aspect the present disclosure provides a compound that is NR4A1 ligand. As described further herein, in certain embodiments 4-, 3- and 2-hydroxyphenyl C-DIM analogs are used as scaffolds to investigate the synthesis and ultimate development of a second generation of NR4A1 ligands that exhibit potent activity against cancer and other diseases where NR4A1 is a potential therapeutic target, such as in metabolic, and neurological diseases.

Accordingly, in an embodiment, the ligand is a compound having the formula:

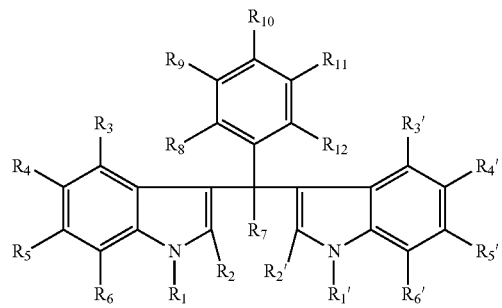

or a salt thereof,
wherein, $R_1$, $R_2$, $R_1'$, and $R_2'$ are each independently selected from the group consisting of hydrogen, a linear alkyl group containing one to about ten carbon atoms, and a branched alkyl group containing one to about ten carbon atoms;

$R_3$, $R_4$, $R_5$, $R_6$, $R_3'$, $R_4'$, $R_5'$, and $R_6'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

$R_7$ is selected from the group consisting of hydrogen, a linear alkyl group containing one to about ten carbon atoms, a branched alkyl group containing one to about ten carbon atoms, a cycloalkyl group containing one to about ten carbon atoms, and an aryl group;

$R_8$, $R_9$, $R_{10}$, $R_{11}$, and $R_{12}$ are independently selected from the group consisting of H, a halogen, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a hydroxyl group, and a haloalkoxy group containing one to about ten carbon atoms;

wherein at least one of $R_8$, $R_9$, $R_{10}$, $R_{11}$, and $R_{12}$ is OH, and wherein when $R_{10}$ is OH at least one of $R_8$, $R_9$, $R_{11}$, and $R_{12}$ is not hydrogen.

As discussed further herein, the compounds of the present disclosure are NR4A1 ligands. In that regard, in some embodiments, the antagonist ligand blocks the constitutive function of the receptor and its ability for stimulatory, cognate ligands to bind to the NR4A1 protein and to activate NR4A1-dependent genes.

Chemical moieties referred to as univalent chemical moieties (e.g., alkyl, aryl, and the like) also encompass structurally permissible multivalent moieties, as understood by those skilled in the art. For example, while an "alkyl" moiety generally refers to a monovalent radical (e.g., CH$_3$CH$_2$—), in appropriate circumstances an "alkyl" moiety can also refer to a divalent radical (e.g., —CH$_2$CH$_2$—, which is equivalent to an "alkylene" group). Similarly, under circumstances where a divalent moiety is required, those skilled in the art will understand that the term "aryl" refers to the corresponding divalent arylene group.

Terms used herein may be preceded and/or followed by a single dash, "—", or a double dash, "=", to indicate the bond order of the bond between the named substituent and is parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is 0 the moiety is B and when a is 1 the moiety is AB.

Where a substituent can vary in the number of atoms or groups of the same kind (e.g., alkyl groups can be $C_1$, $C_2$, $C_3$, and the like), the number of repeated atoms or groups can be represented by a range (e.g., $C_1$-$C_6$ alkyl) which includes each and every number in the range and any and all sub ranges. FOE example, $C_1$-$C_3$ alkyl includes $C_1$, $C_2$, $C_3$, $C_{1-2}$, $C_{1-3}$, and $C_{2-3}$ alkyl.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3).

"Alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocycle heterocyclyl portions of the bicyclic aryl are optionally substituted with one or two oxo and/or this group.

"Halogen" refers to a chloro, bromo, fluoro or iodo atom radical. The terra "halogen" also contemplates terms "halo" or "halide".

The terms "haloalkyl", "haloalkenyl" and "haloalkoxy" refer to an alkyl, alkenyl or alkoxy group, as the case may be, which is substituted with one or more halogen atoms.

The term "nitro" as used herein, means a —$NO_2$ group.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

2-Hydroxy Ligands

In some embodiments, $R_8$ is OH. In certain instances, such ligands are referred to herein as "2-hydroxy" and/or "2-OH" ligands due to the placement of the OH group on the central phenyl group. In certain such embodiments, $R_9$, $R_{10}$, $R_{11}$, and $R_{12}$ are each H. In certain other embodiments, $R_9$, $R_{10}$, $R_{11}$, and $R_{12}$ are independently selected from the group consisting of a halogen, $CH_3$, $OCCl_3$, $CF_3$, t-butyl, $OCH_3$, OH, $C_6H_5$, and CN. In an embodiment, $R_{10}$ is $OCH_3$. In an embodiment, $R_{11}$ is selected from the group consisting of $CH_3$, $OCH_3$, and $CF_3$. In an embodiment, $R_9$ and $R_{11}$ are Br.

In an embodiment, the compositions of the disclosure have one of the following structures:

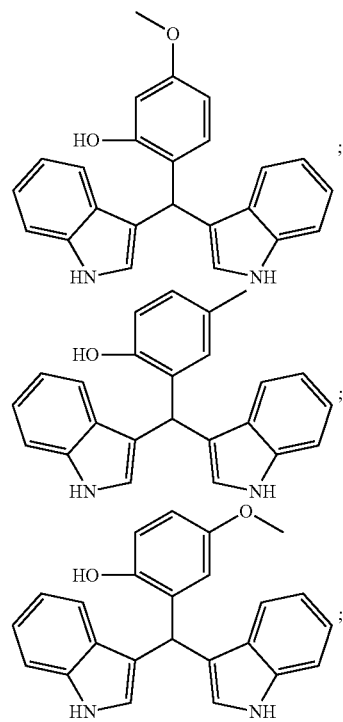

-continued

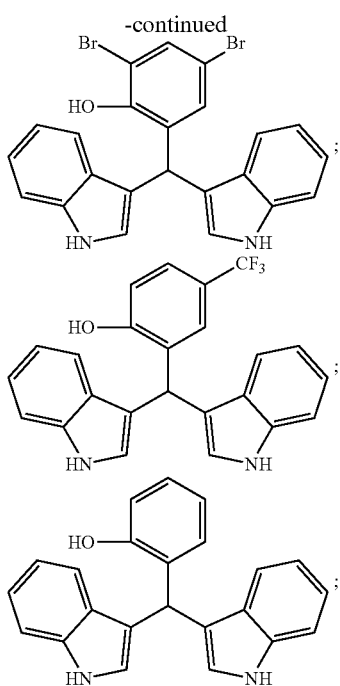

and salts thereof.

3-Hydroxy Ligands

In some embodiments, $R_9$ is OH. In certain instances, such ligands are referred to herein as "3-hydroxy" and/or "3-OH" ligands due to the placement of the OH group on the central phenyl group. In certain such embodiments, $R_8$, $R_{10}$, $R_{11}$ and $R_{12}$, are each H. In certain other embodiments, $R_8$, $R_{10}$, $R_{11}$, and $R_{12}$ are independently selected from the group consisting of a halogen; $CH_3$, $OCCl_3$, $CF_3$, t-butyl, $OCH_3$, OH, $C_6H_5$, and CN. In certain embodiments, $R_8$ is a halogen.

In an embodiment, the compositions of the disclosure have one of the following structures:

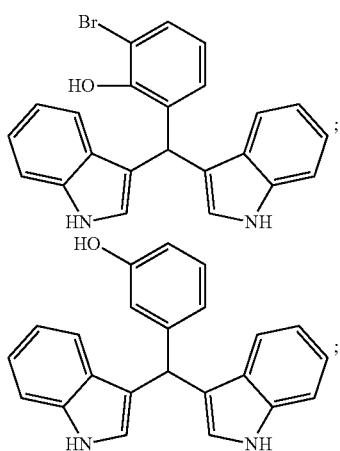

and salts thereof.

4-Hydroxy Ligands

In some embodiments, $R_{10}$ is OH. In certain instances, such ligands are referred to herein as "4-hydroxy" and/or "4-OH" ligands due to the placement of the OH group on the central phenyl group. In certain such embodiments, $R_8$, $R_9$, $R_{11}$, and $R_{12}$ are independently selected the group consisting of a halogen, $CH_3$, $OCCl_3$, $CF_3$, t-butyl, $OCH_3$, OH, $C_6H_5$, and CN. In certain other embodiments, $R_9$ is a halogen and $R_{11}$ is selected from the group consisting of H, a halogen, and $OCH_3$.

In an embodiment, the compositions of the disclosure have one of the following structures:

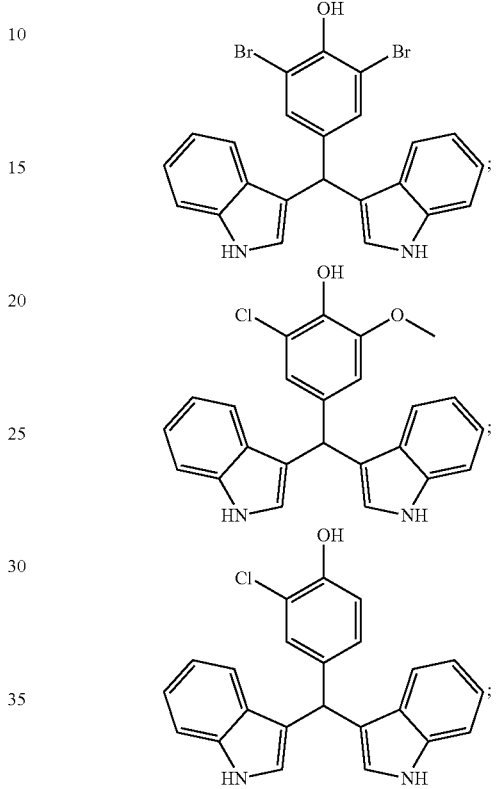

and salts thereof.

The C-DIM compounds of the present disclosure can be prepared by condensation of substituted benzaldehydes with indole or substituted indoles. The compounds can be synthesized by incubating two parts indole or substituted indole with one part benzaldehyde or substituted benzaldehyde in dilute acetic acid at 80-90° C. for 24 48 hours. The solid is recovered by filtration and crystalized from benzene or benzene/hexane to give a 70-90% yield of C-DIM. Use of a single indole starting material will lead to symmetrical products, while use of two different indole starting materials will lead to asymmetrical products.

The preparation and characterization of representative C-DIM compounds is described, for example, in U.S. Pat. No. 7,232,843, incorporated herein by reference in its entirety.

Pharmaceutical Compositions

In certain aspects, the disclosure provides for a pharmaceutical composition comprising a therapeutically effective amount of a compound of the present disclosure together with a pharmaceutically acceptable carrier, and optionally other therapeutic and/or prophylactic ingredients.

The term "therapeutically effective amount" used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth). In some embodiments, an effective amount is an amount sufficient to delay development. In some embodiments, an effective amount is an amount sufficient to prevent occurrence and/or recurrence. An effective amount can be administered in one or more administrations.

"Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sortie acid and esters of p-hydroxybenzoic acid can be added as preservatives. Id. at 1449. In addition, antioxidants and suspending agents can be used. Id.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

The disclosure includes a pharmaceutical composition comprising a compound of the disclosure including isomers, racemic or non-racemic mixtures of isomers, or pharmaceutically acceptable salts or solvates thereof together with one or more pharmaceutically acceptable carriers, and optionally other therapeutic and/or prophylactic ingredients.

In general, the compounds of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the disclosure for a given disease.

Thus, the compounds of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); poly-anions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compounds of the disclosure can be combined with an oral, nontoxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Thus, for example, capsules can be prepared by conventional procedures so that the dosage unit is 100 mg of the compounds of the disclosure, 100 mg of cellulose and 10 mg of magnesium stearate. A large number of unit capsules can also prepared by filling standard two-piece hard gelatin capsules each with 100 mg of powdered active ingredient, 150 mg of lactose, 50 mg of cellulose, and 10 mg magnesium stearate. Or, tablets can be prepared by conventional procedures so that the dosage unit is 100 mg of the compounds of the disclosure, 150 mg of lactose, 50 mg of cellulose and 10 mg of magnesium stearate. A large number of tablets can also be prepared by conventional procedures such that the dosage unit was 100 mg of the compounds of the disclosure, and other ingredients can be 0.2 mg of colloidal silicon dioxide, 5 mg of magnesium stearate, 250 mg of microcrystalline cellulose, 10 mg of starch and 100 mg of lactose. Appropriate coatings can be applied to increase palatability or delay absorption.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms sinkable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered liming a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a steak injectable solution or a suspension in a nontoxic parenterally acceptable diluent or solvent. Among the acceptable vehicles and solvents that can be employed are water, Ringer's solution and isotonic sodium chloride solution. In addition, suede, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the composition, by irradiating the compositions, or by heating the compositions. They can also be manufactured using sterile water, or some other sterile injectable medium, immediately before use.

The formulations can optionally contain an isotonicity agent. The formulations preferably contain an isotonicity agent and glycerin is the most preferred isotonicity agent. The concentration of glycerin, when it is used, is in the range known in the art, such as for example, about 1 mg/mL to about 20 mg/mL.

The pH of the parenteral formulations can be controlled by a buffering agent such as phosphate, acetate, TRIS or L-arginine. The concentration of the buffering agent is preferably adequate to provide buffering of the pH during storage to maintain the pH at a target pH±0.2 pH unit. The preferred pH is between about 7 and about 8 when measured at room temperature.

Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) can optionally be added to the formulation, and can be useful if the formulations will contact plastic materials. In addition, the parenteral formulations can contain various antibacterial and antifungal agents, for example, parabens, chlorobutanol, phenol, sorbic acid, thimerosal, and the like.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base ID be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmuscosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compounds of the disclosure can be formulated for aerosol administration, particularly to the respiratory tract and including intranasal administration. The compound will generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of ding can be controlled by a metered valve. Alternatively the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the disclosure, generally a therapeutic amount will be in the range of about 0.01 mg/kg to about 250 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself or it can be the appropriate number of any of these in packaged form.

Methods of Modulating NR4A1 Activity

In another aspect, the present disclosure provides a method of modulating NR4A1 activity in a cell, comprising administering to the cell a compound or a pharmaceutical composition described herein.

In some embodiments, modulating NR4A1 activity comprises the binding of a compound described elsewhere herein to the NR4A1 protein. In some embodiments, the compound has antagonistic activity, namely the compound has reduced or no efficacy in stimulating the cognate function of the receptor (e.g., an antagonist ligand). In some embodiments, the antagonist ligand blocks the constitutive function of the receptor and its ability for stimulatory, cognate ligands to bind to the NR4A1 protein and to activate NR4A1-dependent genes. In some embodiments, the NR4A1 ligand can be a tissue-, response-, or gene-specific agonist.

The term "antagonist" refers to a compound that can combine with a NR4A1 receptor to reduce or inhibit a molecular and cellular activity. An antagonist may be a ligand that directly binds to the receptor. Alternatively, an antagonist may combine with a receptor indirectly by, for example, (a) forming a complex with another molecule or protein that directly binds to the receptor, or (b) otherwise results in the modification of another compound so that the other compound directly binds to the NR4A1 receptor.

The term "agonist" refers to a compound that can combine with a NR4A1 receptor to produce or increase a molecular and cellular activity. An agonist may be a ligand that directly binds to the receptor. Alternatively, an agonist may combine with a receptor indirectly by, for example, (a) forming a complex with another molecule or protein that directly binds to the receptor, or (b) otherwise results in the modification of another compound so that the other compound directly binds to the NR4A1 receptor.

The term "activate", and variations thereof refers to any measurable increase in molecular and cellular activity.

In an embodiment, the cell is a cancer cell.

In an embodiment, the cell is contacted with the compound or pharmaceutical composition in vitro. In an embodiment, the cell is contacted with the compound or pharmaceutical composition in vivo by administering an effective amount of the compound or pharmaceutical composition to a subject.

In an embodiment, modulation of NR4A1 activity induces down-regulation of a protein selected from the group consisting β1-integrin, TXNDC5, survivin, EFGR, PAX3-FOX01A, and combinations thereof. In an embodiment, modulation of NR4A1 activity induces up-regulation of a protein selected from the group consisting of SERPINB5, GADD45α, and combinations thereof.

In an embodiment, the compound has the formula:

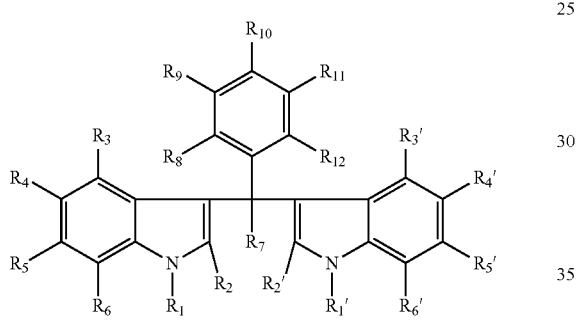

or a salt thereof,
wherein, $R_1$, $R_2$, $R_1'$, and $R_2'$ are each independently selected from the group consisting of hydrogen, a linear alkyl group containing one to about ten carbon atoms, and a branched alkyl group containing one to about ten carbon atoms;

$R_3$, $R_4$, $R_5$, $R_6$, $R_3'$, $R_4'$, $R_5'$, and $R_6'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

$R_7$ is selected from the group consisting of hydrogen, a linear alkyl group containing one to about ten carbon atoms, a branched alkyl group containing one to about ten carbon atoms, a cycloalkyl group containing one to about ten carbon atoms, and an aryl group;

$R_8$, $R_9$, $R_{10}$, $R_{11}$, and $R_{12}$ are independently selected from the group consisting of H, a halogen, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a hydroxyl group, and a haloalkoxy group containing one to about ten carbon atoms;

wherein at least one of $R_8$, $R_9$, $R_{10}$, $R_{11}$ and $R_{12}$ is OH, and wherein when $R_{10}$ is OH at least one of $R_8$, $R_9$, $R_{11}$, and $R_{12}$ is not hydrogen.

4-Hydroxy Ligands

In an embodiment, $R_{10}$ is OH. In certain such embodiments, $R_8$, $R_9$, $R_{11}$, and $R_{12}$ are independently selected the group consisting of a halogen, $CH_3$, $OCCl_3$, $CF_3$, t-butyl, $OCH_3$, OH, $C_6H_5$, and CN. In certain other embodiments, $R_9$ is a halogen and $R_{11}$ is selected from the group consisting of H, a halogen, and $OCH_3$.

In an embodiment, the compositions of the disclosure have one of the following structures:

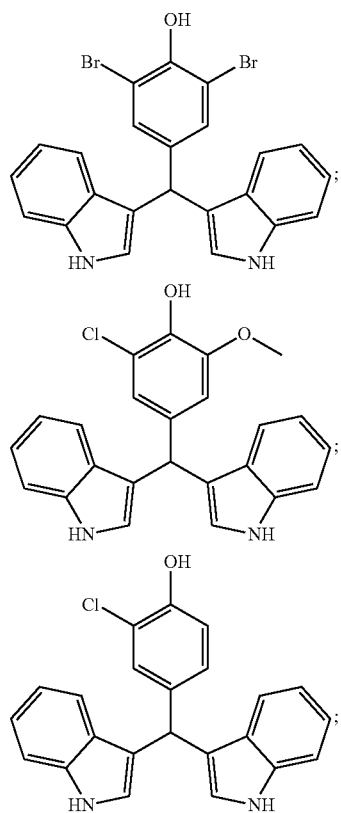

and salts thereof.

2-Hydroxy Ligands

In an embodiment, $R_9$ is OH. In certain such embodiments, $R_8$, $R_{10}$, $R_{11}$, and $R_{12}$ are each H. In certain other embodiments, $R_8$, $R_{10}$, $R_{11}$, and $R_{12}$ are independently selected from the group consisting of a halogen, $CH_3$, $OCCl_3$, $CF_3$, t-butyl, $OCH_3$, OH, $C_6H_5$, and CN. In certain embodiments, $R_8$ is a halogen.

In an embodiment, the compositions of the disclosure have one of the following structures:

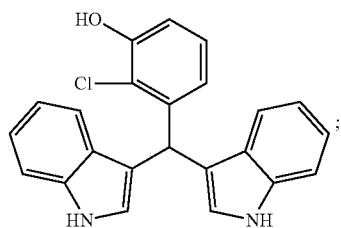

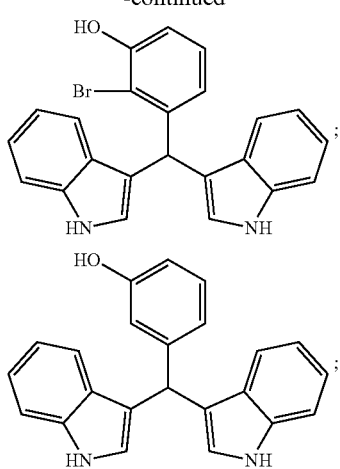

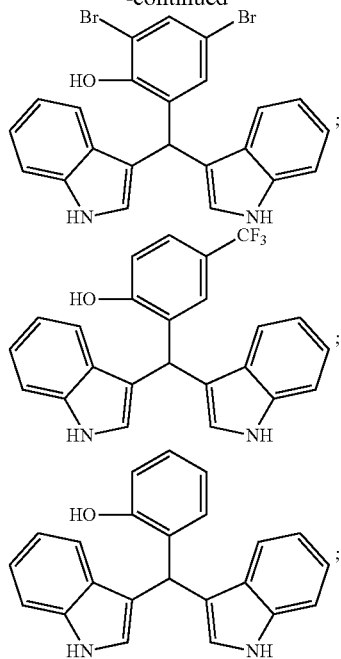

and salts thereof.

3-Hydroxy Ligands

In an embodiment, $R_8$ is OH. In certain such embodiments, $R_9$, $R_{10}$, $R_{11}$, and $R_{12}$ are each H. In certain other embodiments, $R_9$, $R_{10}$, $R_{11}$, and $R_{12}$ are independently selected from the group consisting of a halogen, $CH_3$, $OCCl_3$; $CF_3$, t-butyl, $OCH_3$, OH, $C_6H_5$, and CN. In an embodiment, $R_{10}$ is $OCH_3$. In an embodiment, $R_{11}$ is selected from the group consisting of $CH_3$, $OCH_3$, and $CF_3$. In an embodiment, $R_9$ and $R_{11}$ are Br.

In an embodiment, the compositions of the disclosure have one of the following structures:

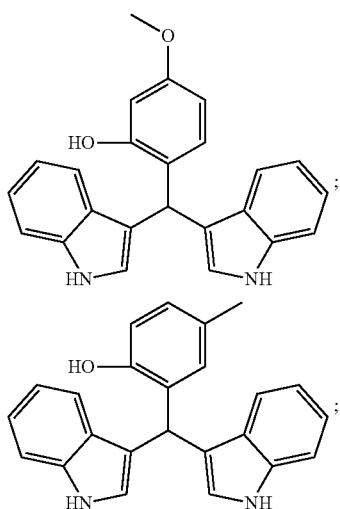

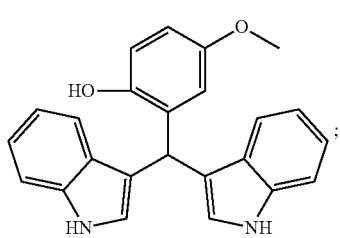

and salts thereof.

Methods of Treating a Disease or Condition

In another aspect, the present disclosure provides methods of treating a disease or condition in an individual treatable by modulation of NR4A1 activity comprising administering to the individual a therapeutically effective amount of a compound or a pharmaceutical composition described herein.

Those having ordinary skill in the art will be able to ascertain the most effective dose and times for administering the compositions, considering route of delivery, metabolism of the compound, and other pharmacokinetic parameters such as volume of distribution, clearance, age of the subject, and so on. For example, the NR4A1 antagonist can be administered in any well-known method, such as by topical administration, oral administration, intravenous injection, intraperitoneal injection, intramuscular injection, intranasal administration, transdermal administration, rectal administration, or by any means which delivers an effective amount of the active agent to the tissue or site to be treated. Suitable dosages are those which achieve the desired endpoint. It will be appreciated that different dosages may be required for treating different disorders. An effective amount of an agent is, for example, that amount which causes a cessation or significant decrease in neoplastic cell count, growth, size, cell migration or cell invasion.

The compositions can be administered along with a pharmaceutical carrier and/or diluent. The agents may also be administered in combination with other agents, for example, in association with other chemotherapeutic or immuno-stimulating drugs or therapeutic agents, such as in the treatment of cancer. Examples of pharmaceutical carriers or diluents useful in the present invention include any physiological buffered medium, i.e., about pH 7.0 to 7.4 comprising a suitable water soluble organic carrier. Suitable water soluble organic carriers include, but are not limited to corn oil, dimethylsulfoxide, gelatin capsules, and so on.

The individual can be any animal, such as a mammal, bird, reptile, or fish. Exemplary mammalian categories include rodents, primates, canines, felines, ungulates, lagomorphs, and the like. For example, the individual can be a human, monkey, ape or other primate, mouse, rat or other rodent, dog, cat, pig, horse, cow, or rabbit, etc.

As used herein, the term "treatment" means providing an ameliorative, curative, or preventative effect on the disorder or condition. In some embodiments, treatment includes preventing the escalation or progression, or slowing the rate of escalation or progression, of the condition (as compared to no or other treatment). In the context of cancers (more described below), treatment includes slowing or preventing the cell growth or rate of cell division, slowing or preventing cell migration, and/or slowing or preventing cell invasion.

Exemplary conditions include cancer, diabetes mellitus, thrombosis, colitis, Crohn's disease, inflammatory bowel disease, multiple sclerosis, rheumatoid arthritis immunosuppression disorder, arthritis, asthma, stroke, restenosis, rhinitis, and osteoporosis. Exemplary cancers include pancreatic, kidney, colon, rhabdomyosarcoma, lung, and breast cancer.

In an embodiment, the disease is cancer. In an embodiment, the cancer is selected from the group consisting of pancreatic cancer, breast cancer, colon cancer, rhabdomyosarcoma, and lung cancer.

In an embodiment, modulation of NR4A1 activity induces down-regulation of a protein selected from the group consisting β1-integrin, TXNDC5, survivin, EFGR, PAX3-FOX01A, and combinations thereof. In an embodiment, modulation of NR4A1 activity induces up-regulation of a protein selected from the group consisting of SERPINB5, GADD45α, and combinations thereof.

In an embodiment, the disease is diabetes mellitus and modulation of NR4A1 activity induces glucose uptake in the individual. In an embodiment, modulation of NR4A1 activity induces up-regulation GLUT-4 and Rab4 and phosphorylation of AMPK.

NR4A1 Binding with 4-Hydroxy Substituted NR4A1 Ligands

The following is a description of compounds in accordance with embodiments of the disclosure binding with NR4A1.

Figure 9:
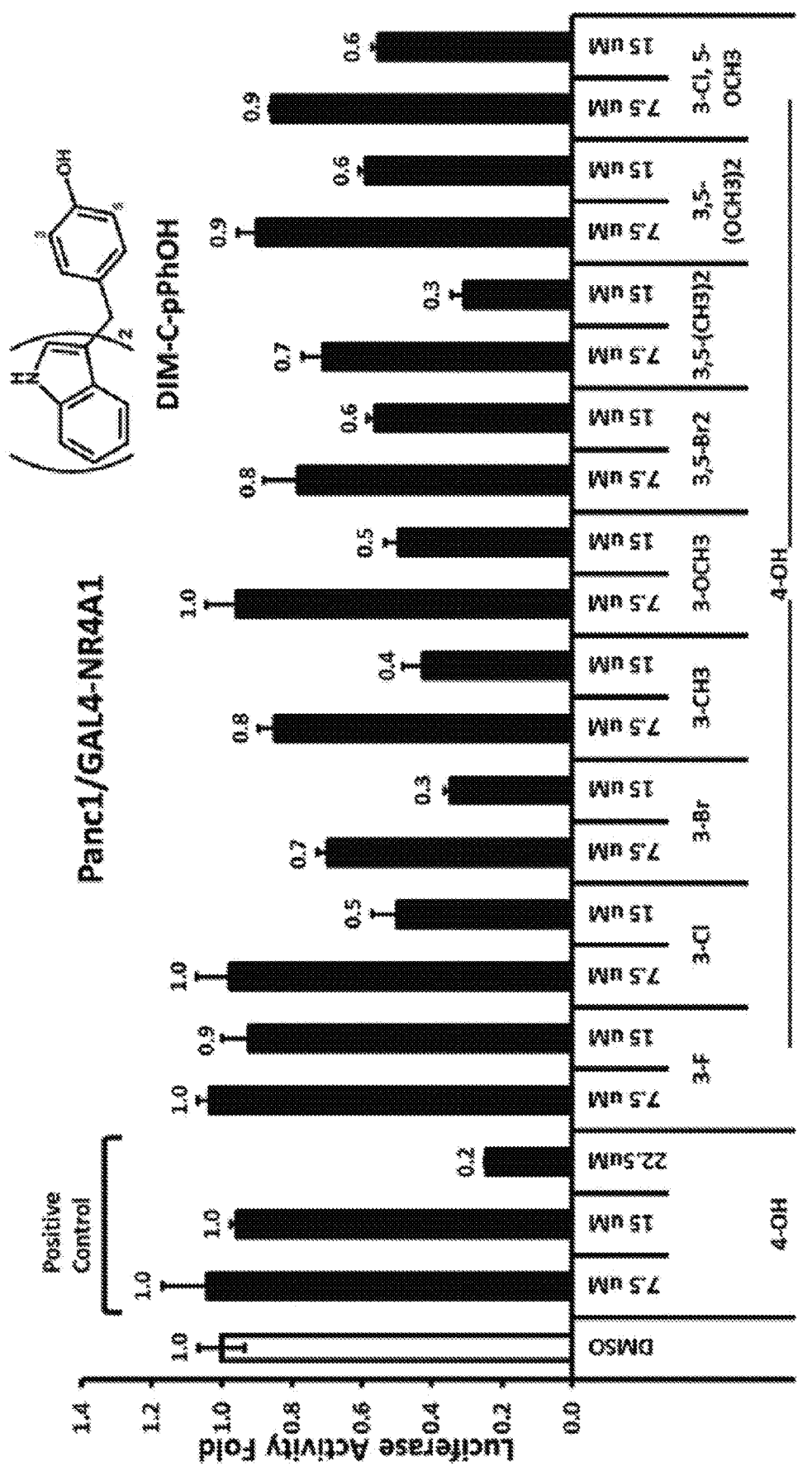
FIG. 9 graphically illustrates luciferase activity in Panc1 cells transfected with GAL4-NR4A1 and UAS-Luc treated with 4-hydroxy C-DIM analogs, according to embodiments of the present disclosure.

The 4-hydroxy compound (C-DIM8) bound with high affinity to NR4A1 and was an effective NR4A1 antagonist that inhibited expression of several pro-oncogenic NR4A1-regulated genes/pathways. Although the 4-hydroxy analog is a relatively potent tumor growth inhibitor in mouse xenograft models, it has a relatively short serum half-life. Therefore, nine substituted 4-hydroxy analogs were synthesized to investigate their relative potencies as NR4A1 ligands and their half-lives since some of the substituents buttress the hydroxy group. Their effects on activation/inactivation of GAL4-NR4A1 and GAL4-NR4A2 in Panc1 cells were determined (see FIGS. 9 and 13).

Significant inhibition of GAL4-NR4A1 transactivation by the 4-hydroxy reference compound was only observed at 22.5 µM and not at 15 µM (steep dose response curve). The substituted 4-hydroxy analogs were tested at concentrations of 7.5 µM and 15 µM and with the exception of the 3-fluoro-4-hydroxy analog, the 8 remaining 4-hydroxy substituted compounds were more potent than the 4-hydroxy reference compound as inhibitors of NR4A1-dependent transactivation. See FIG. 9.

The effects of the 4-hydroxy reference compound and the nine analogs were compared with respect to down-regulation of two NR4A1-regulated gene products in Rh30 rhabdomyosarcoma cells, namely TXNDC5 and PAX3-FOX01A. See FIG. 10B. At the high dose of 20 µM, the 4-hydroxy reference compound decreased expression of both gene products by 50-60%; in contrast, all nine analogs decreased expression of both gene products by 80 to >95% at a concentration of 5 µM. Thus, all of the analogs were >4 times more potent than the 4-hydroxy reference compound and thus represent a promising new second generation of NR4A1 ligands. The results also indicate that NR4A1-dependent transactivation assays appear to be less predictive than NR4A1-regulated gene products in determining differences in NR4A1 antagonist potencies.

Figure 14:
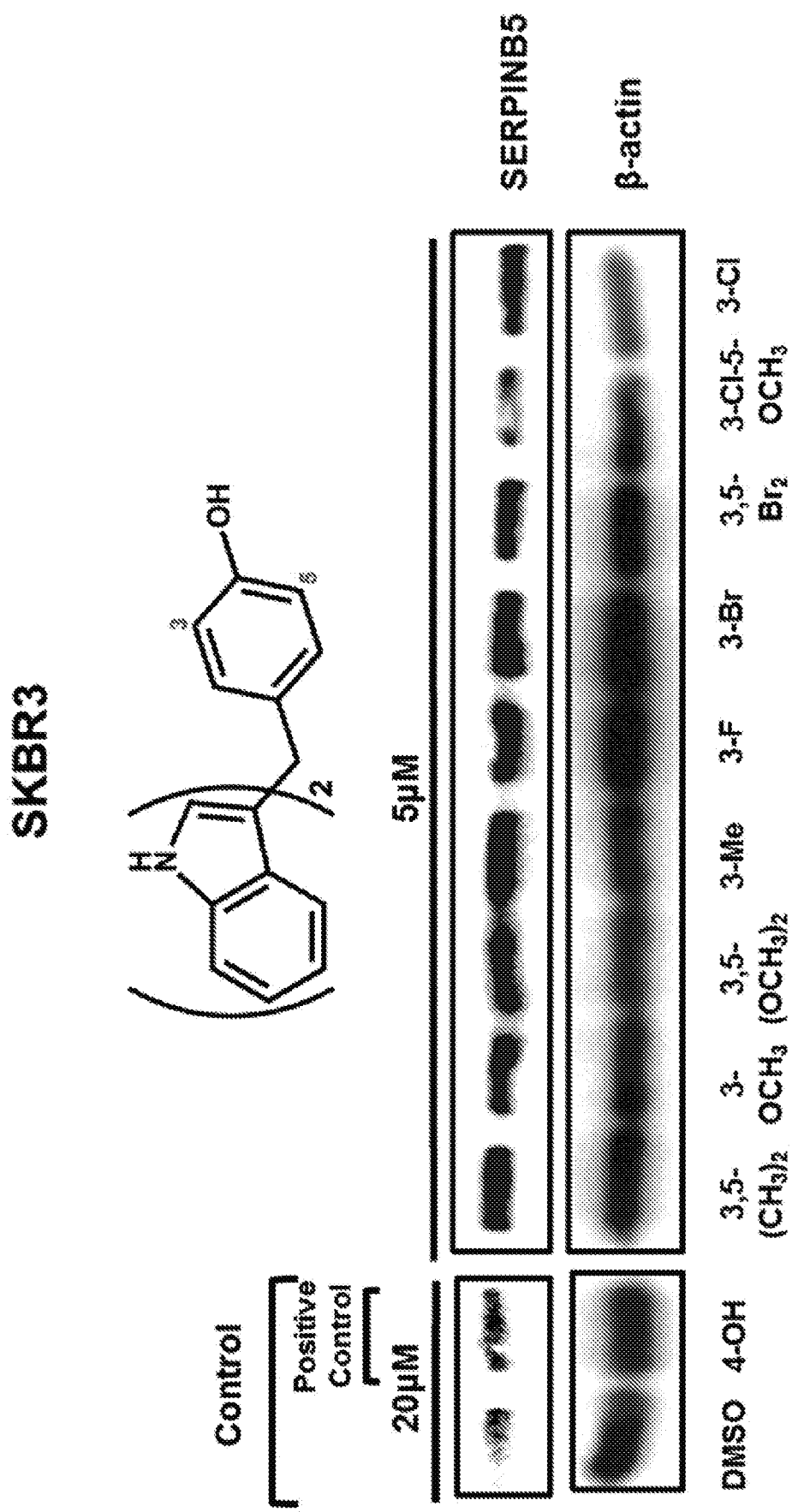
FIG. 14 includes an image of a western blot of SKBR3 cells treated with 3-hydroxy C-DIM analogs, according to embodiments of the present disclosure.
Figure 19:
FIG. 19 includes images of western blots of dissociated tumor cell lysate from an orthotopic breast cancer model treated with 4-hydroxy C-DIM analogs, according to embodiments of the present disclosure, showing down-regulation of NR4A1 gene products, and up-regulation of GADD45α, SERPINB5, and c-PARP.
Figure 19:
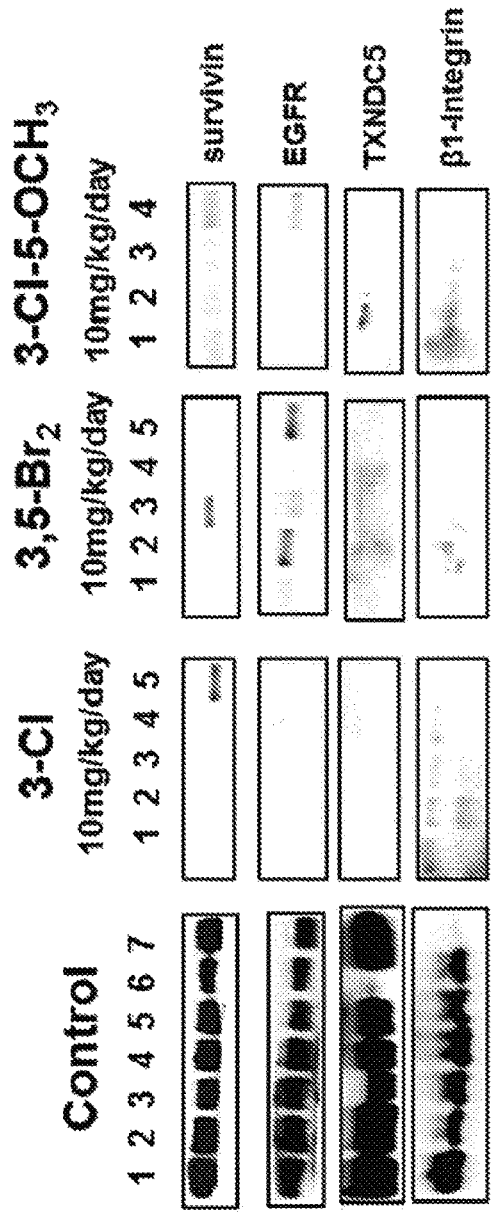
Figure 19:
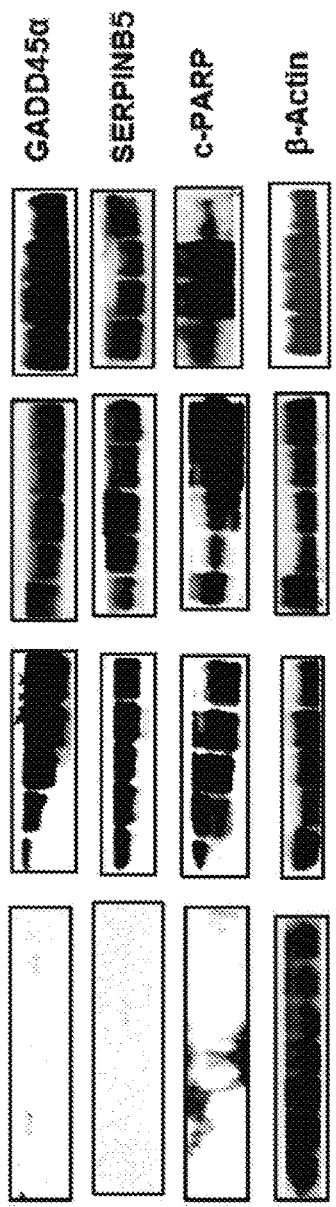

In addition, C-DIM-mediated inhibition of NR4A1-regulated gene products in Panc1 and SKBR3 cells by the same compounds were examined. See FIGS. 10A and 14, and 19. These results are similar to those observed in Rh30 cells.

Ligands for nuclear receptors both activate and repress gene expression and since NR4A1 is pro-oncogenic, we have focused on NR4A1 ligands as antagonists or inhibitors of NR4A1-regulated genes.

Compared to the 4-bromo reference compound [i.e. 1,1-bis(3'-indolyl)-1-(p-bromophenyl)methane], the 4-hydroxy analogs minimally activated GAL4-NR4A2, demonstrating that these compounds appear to be NR4A1-specific. See, for example, FIG. 13.

Structure Activity Relationship of 4-Hydroxy Ligands

The following is a description of structure activity relationships of compounds in accordance with embodiments of the disclosure.

It is likely that NR4A1 will be a major player in metabolic diseases, and derivatives of DIM-C-pPhOH (C-DIM8; NR4A1 standard) that represent a second generation of NR4A1 ligands that are potent in both in vivo and in vitro assays have been identified, as discussed further herein.

Figure 11A:
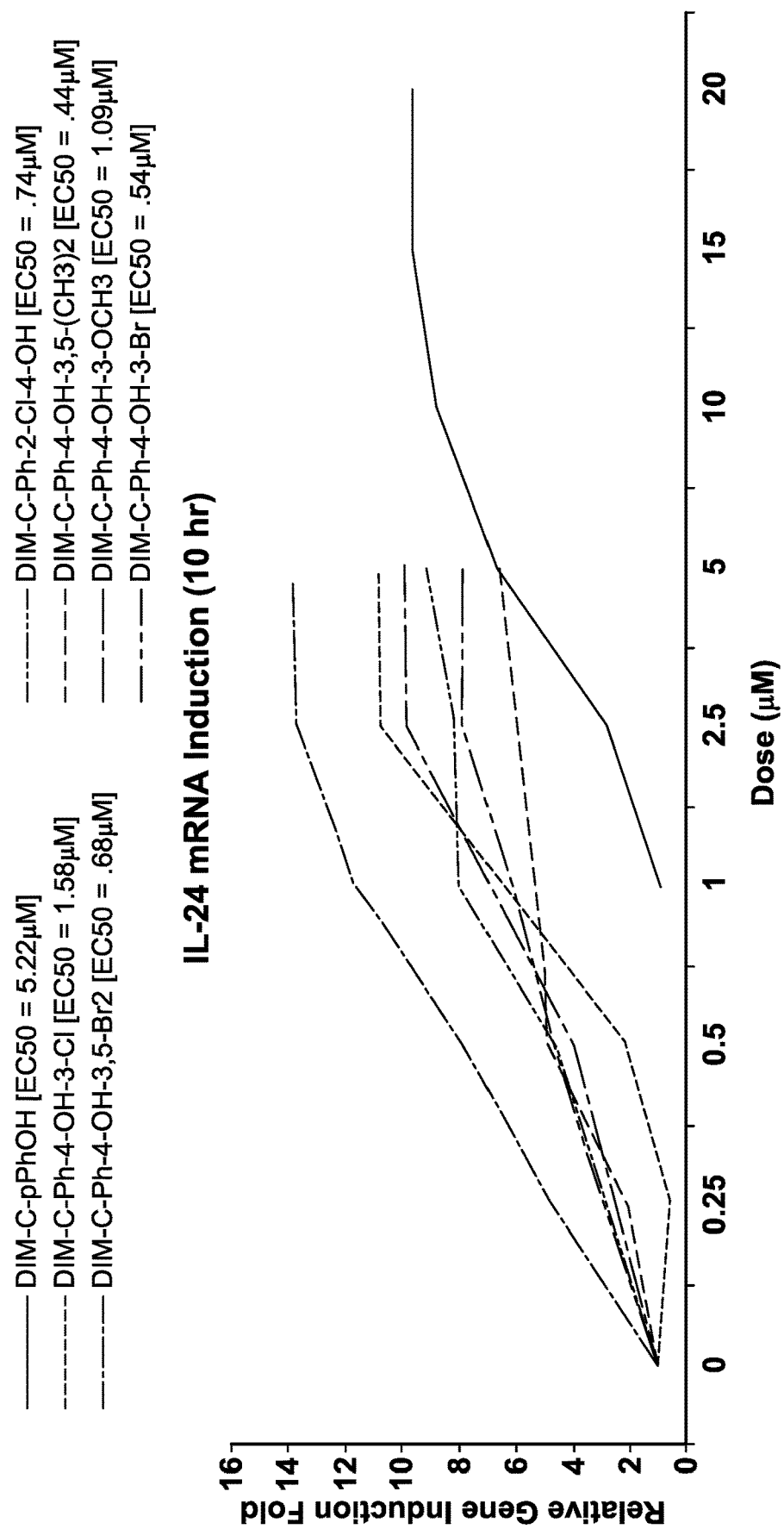
FIGS. 11A-11C graphically illustrate NR4A1-dependent induction of interleukin-24 (IL-24), guanine deaminase (GDA) and doublecortin domain containing 2 (DCDC2), respectively, by DIM-C-pPhOH (the 4-OH compound) and substituted C-DIM analogs, according to embodiments of the present disclosure, in Rh30 cells.
Figure 11B:
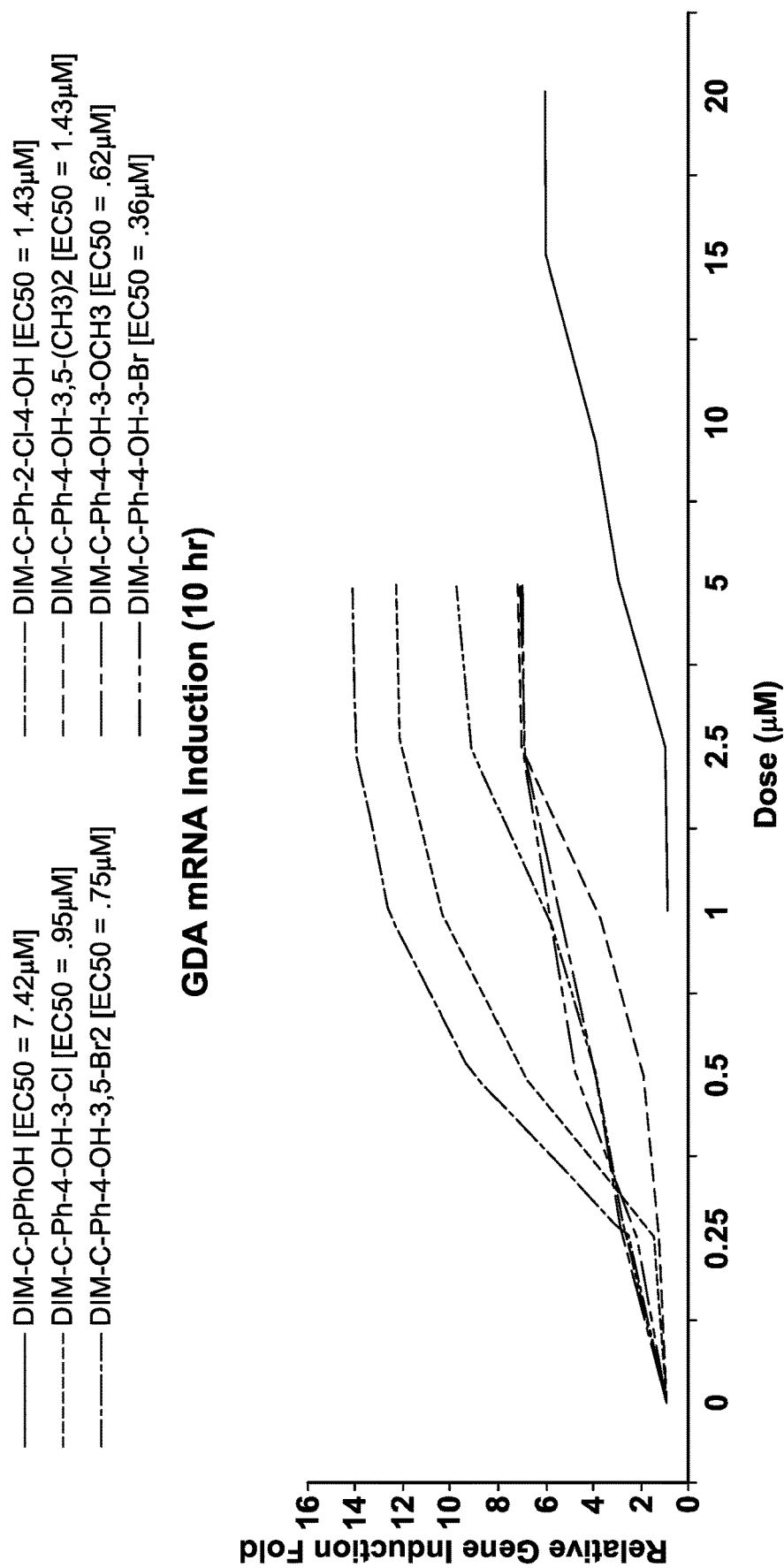
Figure 11C:
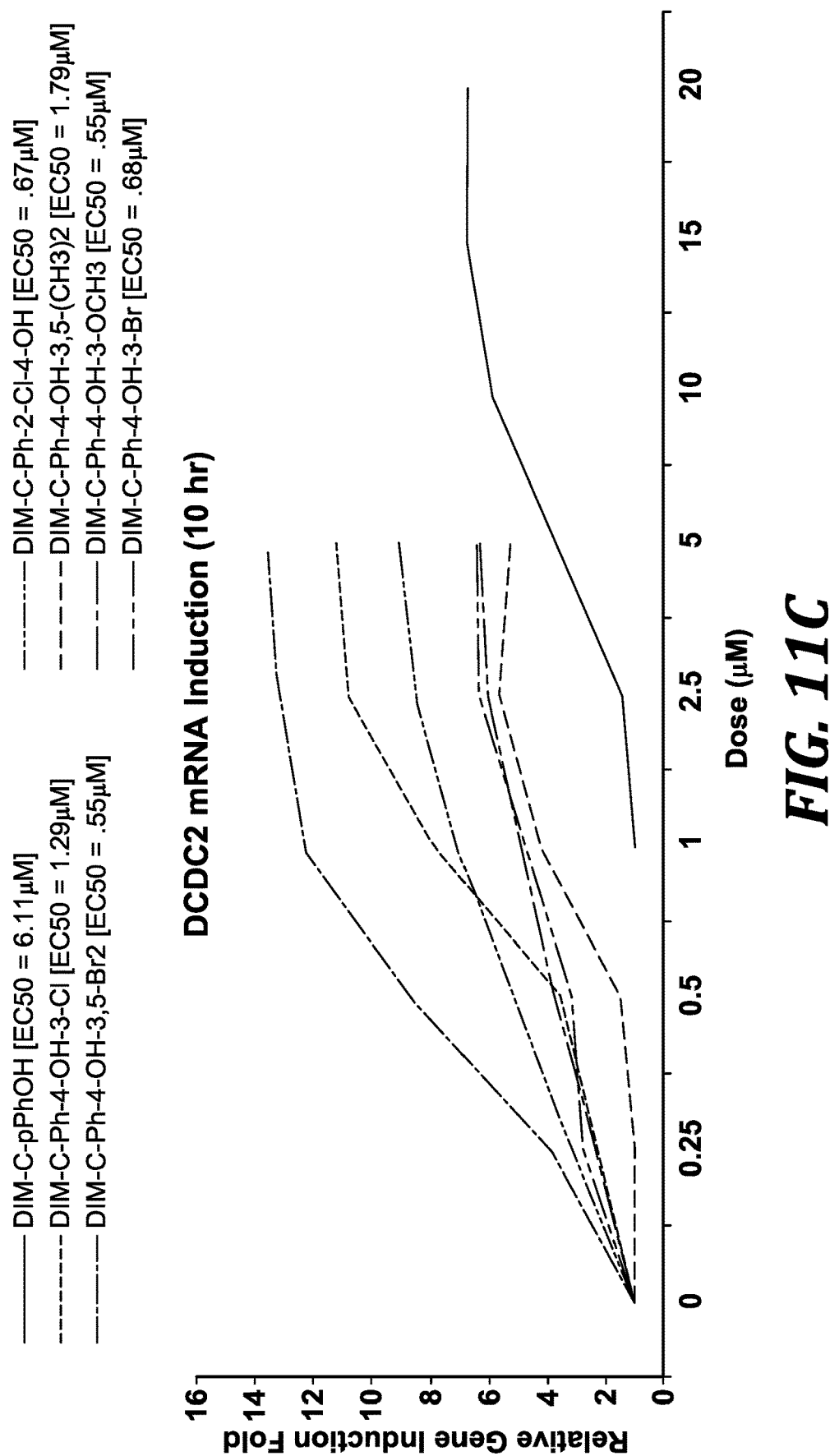

FIGS. 11A-11C summarize the completed structure-activity relationship studies for induction of interleukin-24 (IL-24), guanine deaminase (GDA) and doublecortin domain containing 2 (DCDC2) mRNAs by DIM-C-pPhOH and six substituted analogs in Rh30 cells. The $EC_{50}$ values for induction clearly show structure-dependent potencies and this is also reflected in their efficacies (i.e. maximal induction potencies).

NR4A1 and NR4A2 Binding with 4-Hydroxy Ligands Measured by Surface Plasmon Resonance The following is a description of binding of compounds in accordance with embodiments of the disclosure to NR4A1 using surface plasmon resonance (SPR).

Figure 22:
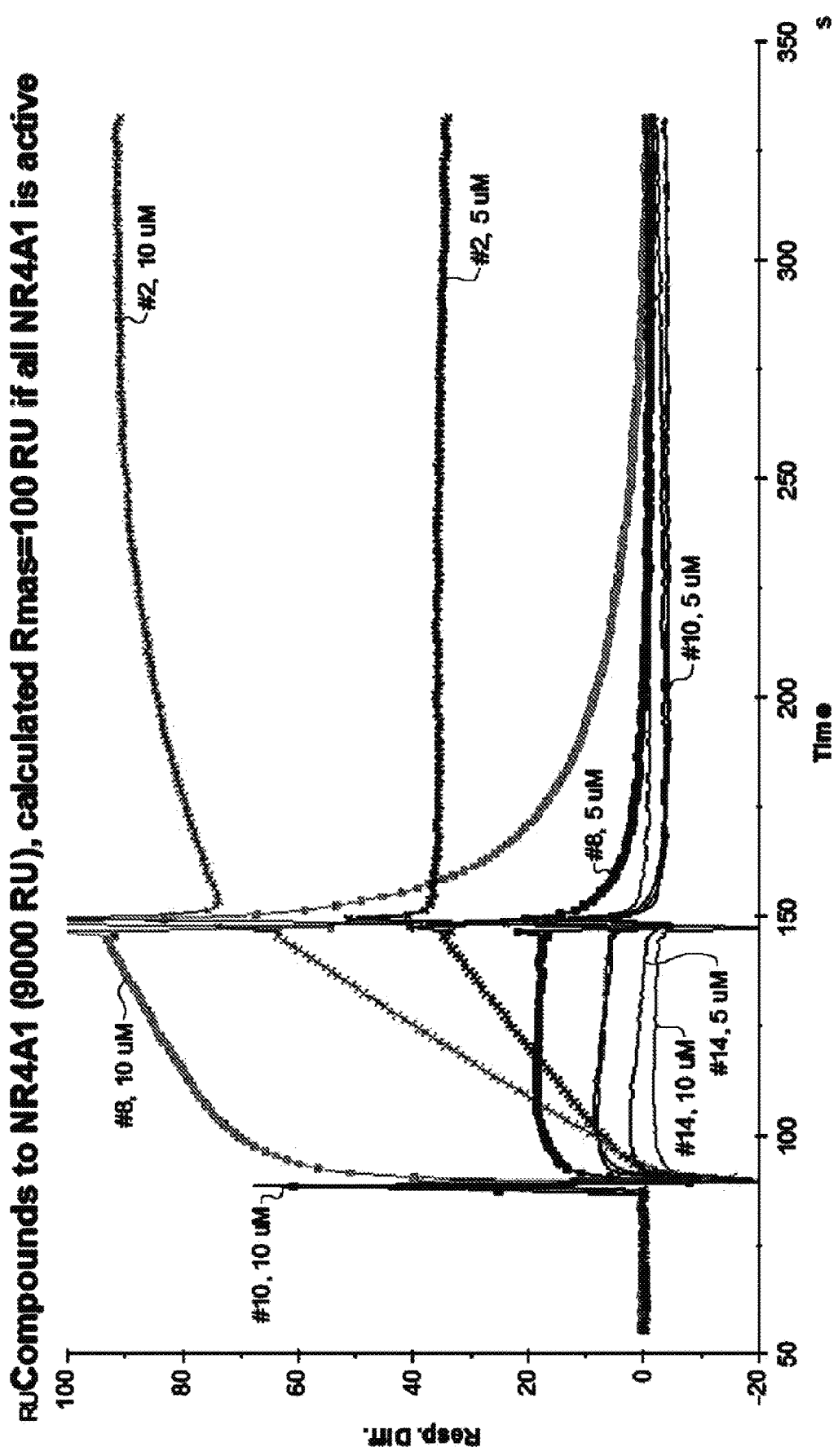
FIG. 22 is a surface plasmon resonance (SPR) response curve of C-DIM analogs, according to embodiments of the present disclosure, binding to NR4A1.

Binding experiments were performed using the SPR method at 25° C. on Biacore 3000 system (GE Healthcare). Purified NR4A1 and NR4A2 LBD proteins were covalently immobilized on CM5 sensor chip (GE) using an amine coupling procedure. Alternatively, the more expensive his-tag-binding NTA sensor chip (GE) can be used to insure correct protein surface orientation. SPR response curves (sensorgrams) were generated after ligand injection using 5 or 10 µM DIM-C-pPhX analogs with X=Br (#2), X=OH (#8), X=CN (#10) and X=$CO_2$Me (#14) (see FIG. 22). While both proteins were immobilized successfully on the chip, NR4A2 seemed to aggregate/oligomerize in the testing buffer condition hence the buffer ionic strength needs further optimization. DIM-C-pPhOH (C-DIM8) bound with high affinity to NR4A1 and DIM-C-pPhBr (C-DIM2) exhibited sticky interactions with both proteins and this is a problem for $K_d$ determinations.

NR4A2-Dependent Osteopontin Gene Expression of Cells Treated with 4-Hydroxy Ligands Induction of expression of osteopontin (OPN) by compounds in accordance with embodiments of the present disclosure is shown.

Figure 21:
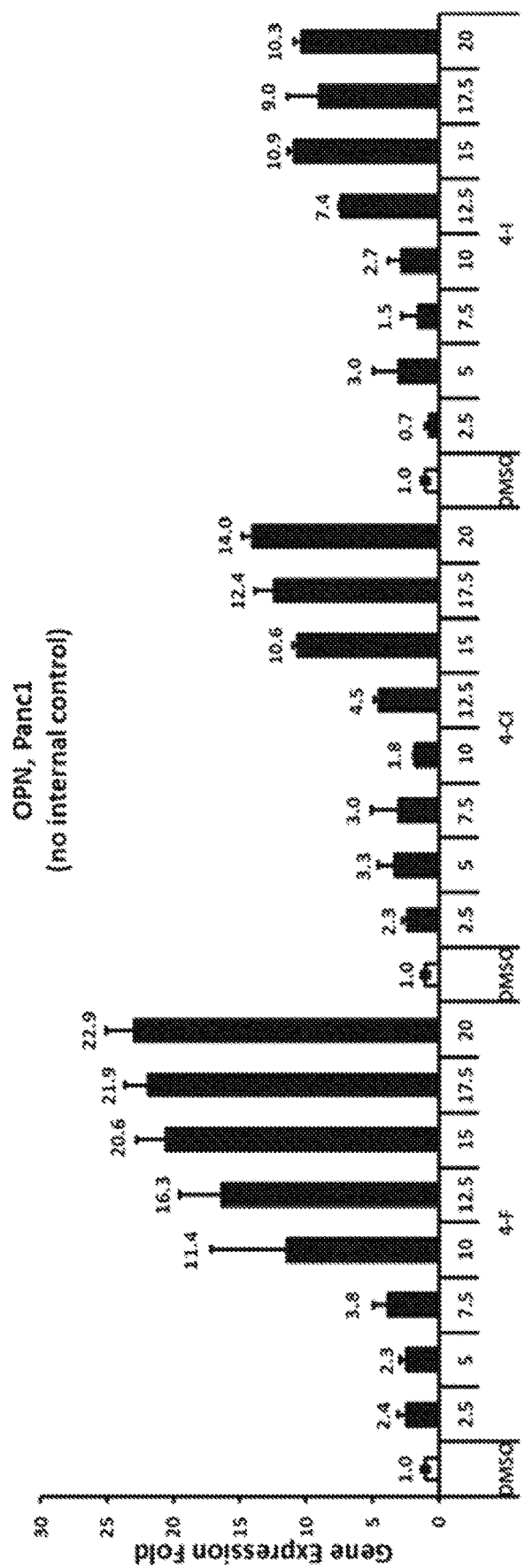
FIG. 21 graphically illustrates NR4A2-dependent induction of osteopontin (OPN) gene expression in Panc1 cells treated with C-DIM analogs, according to embodiments of the present disclosure.

Panc1 cells were treated with DIM-C-pPhX (halogen-substituted) analogs containing 4-F, 4-Cl and 4-I substituents at concentrations from 2.5 to 20 µM with 2.5 µM increments and NR4A2-dependent OPN gene expression was determined using qPCR analysis. The compound treatment affected the expression of GAPDH which was initially intended to serve as the internal control. However, mRNA levels were determined and same amount of mRNA was used for each qPCR reaction. The fold induction of OPN can be used to determine dose response curves and $EC_{50}$ values (FIG. 21). In certain embodiments, other housekeeping genes such as beta actin and 18S ribosomal RNA are currently used as internal controls.

NR4A1 Binding with 3-Hydroxy and 2-Hydroxy Ligands

The following is a description of NR4A1 binding by 3-hydroxy and 2-hydroxy compounds in accordance with embodiments of the disclosure.

The 4-hydroxy compound (C-DIM8) bound with high affinity to NR4A1 and was an effective NR4A1 antagonist that inhibited expression of several pro-oncogenic NR4A1-regulated genes/pathways. Above, it is shown that analogs of the 4-hydroxy compound represent a new generation of more potent NR4A1 ligands.

The results described herein indicate that, in certain embodiments, 3-hydroxy (3 OH) and 2-hydroxy (2-OH) compounds are more potent than the 4-OH standard as NR4A1 antagonists/agonists.

Figure 3:
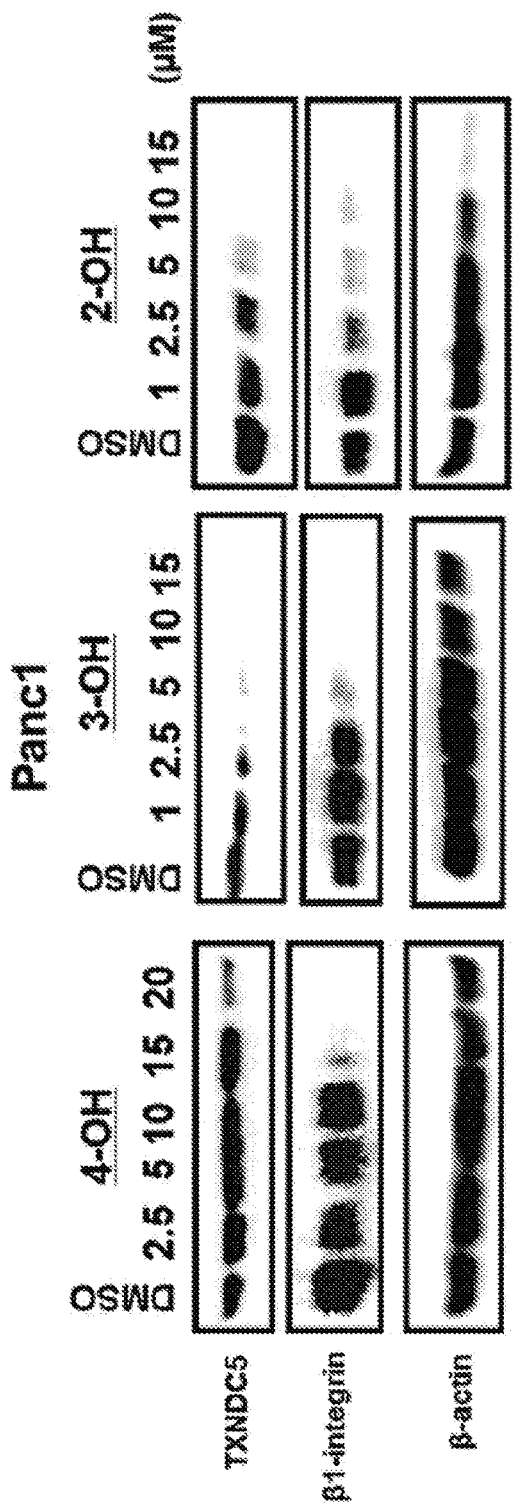
FIG. 3 includes images of western blots of Panc1 (pancreatic) and SKBR3 (breast) cancer cells treated with monohydroxy C-DIM compounds, according to embodiments of the present disclosure, showing down-regulation of expression of two NR4A1-dependent factors, β1-integrin and TXNDC5.
Figure 3:
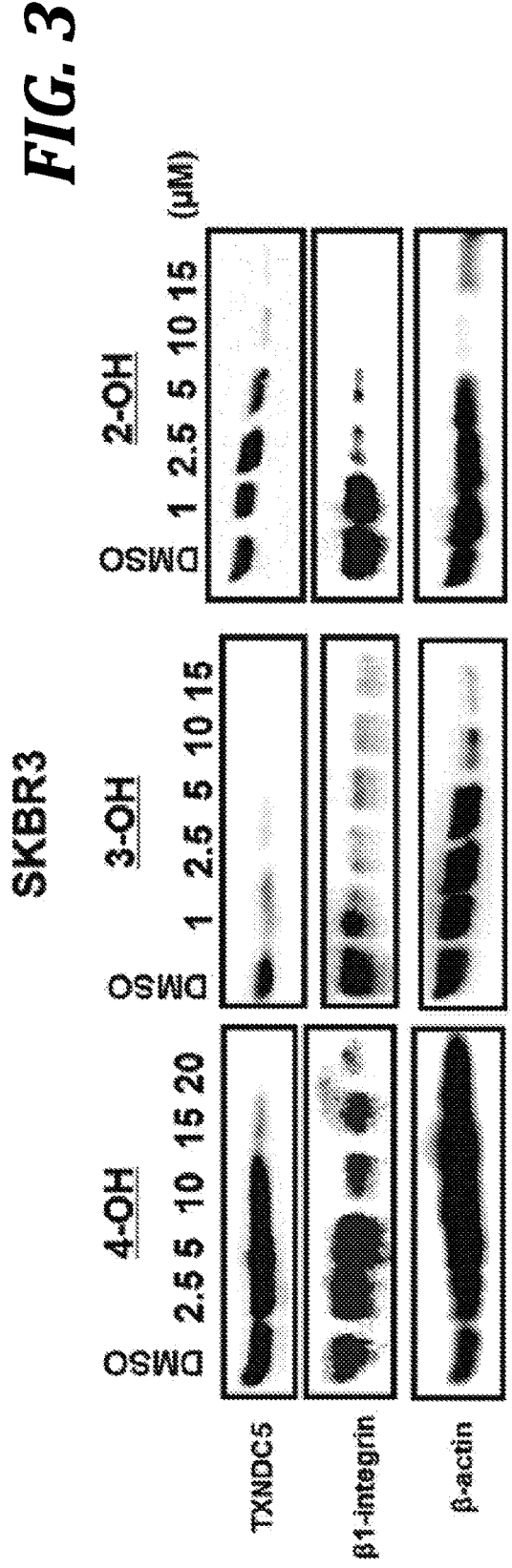
Figure 6:
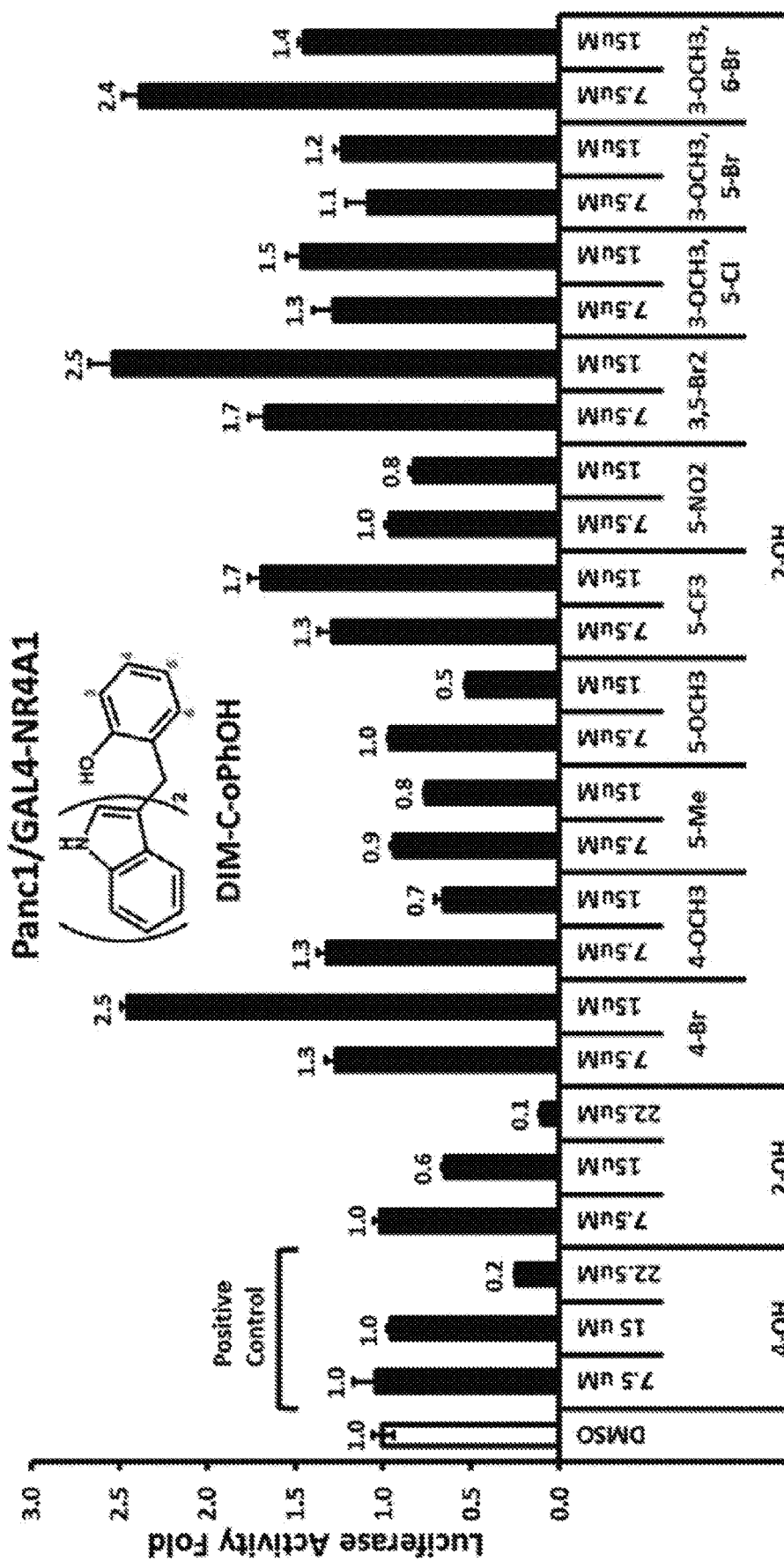
FIG. 6 graphically illustrates luciferase activity in Panc1 cells transfected with GAL4-NR4A1 and UAS-Luc treated with 2-hydroxy C-DIM analogs, according to embodiments of the present disclosure.
Figure 7:
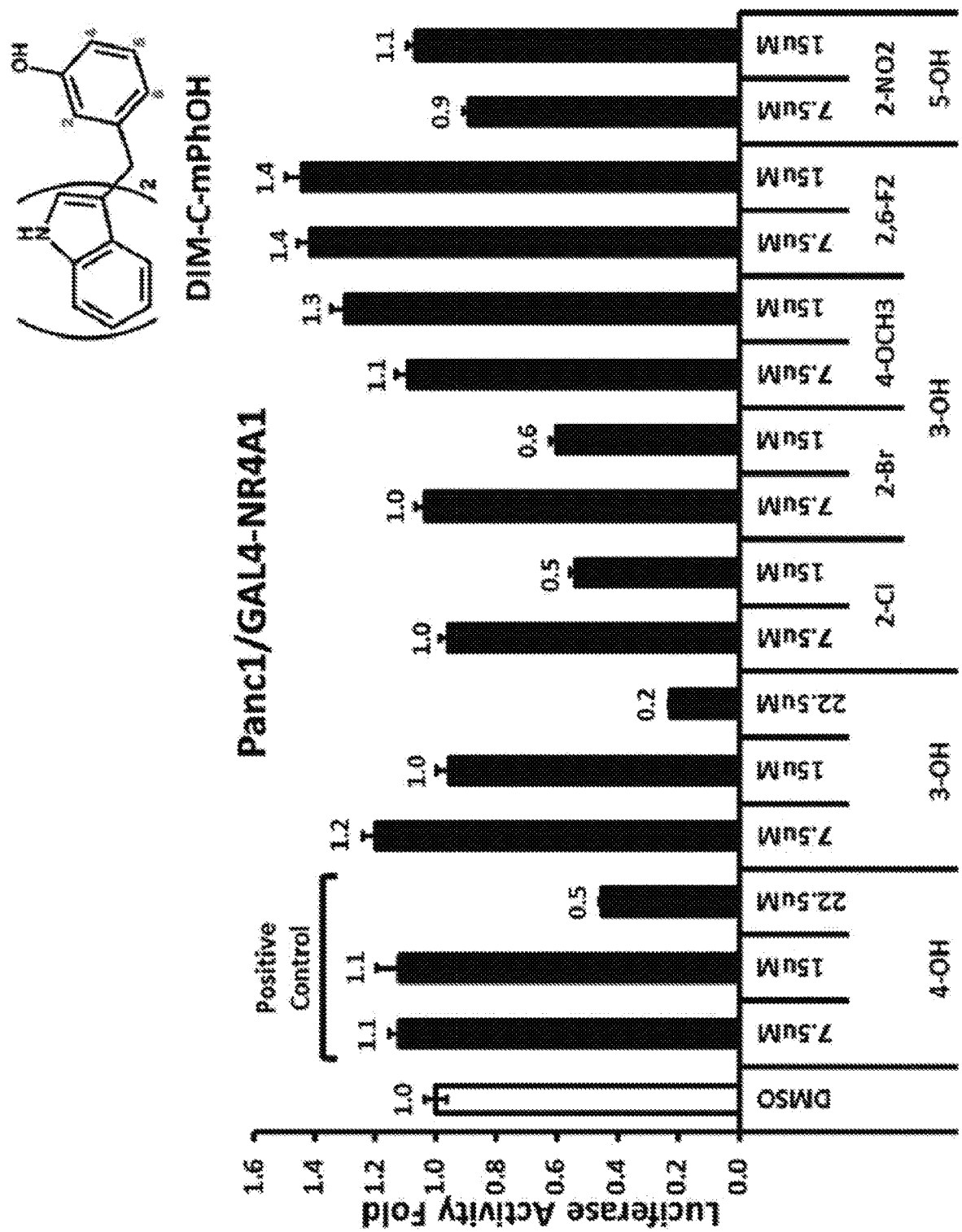
FIG. 7 graphically illustrates luciferase activity in Panc1 cells transfected with GAL4-NR4A1 and UAS-Luc treated with 3-hydroxy C-DIM analogs, according to embodiments of the present disclosure.
Figure 8:
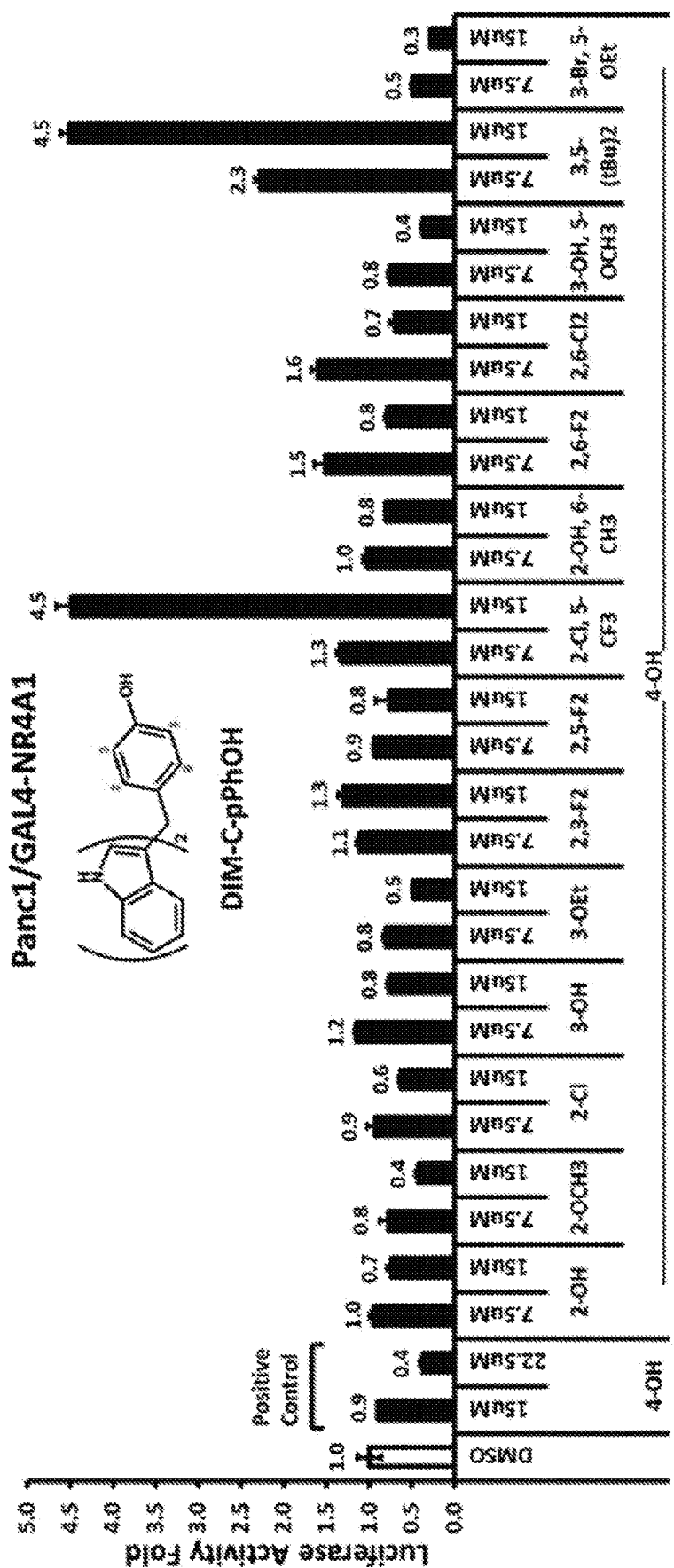
FIG. 8 graphically illustrates luciferase activity in Panc1 cells transfected with GAL4-NR4A1 and UAS-Luc treated with 4-hydroxy C-DIM analogs, according to embodiments of the present disclosure.
Figure 13:
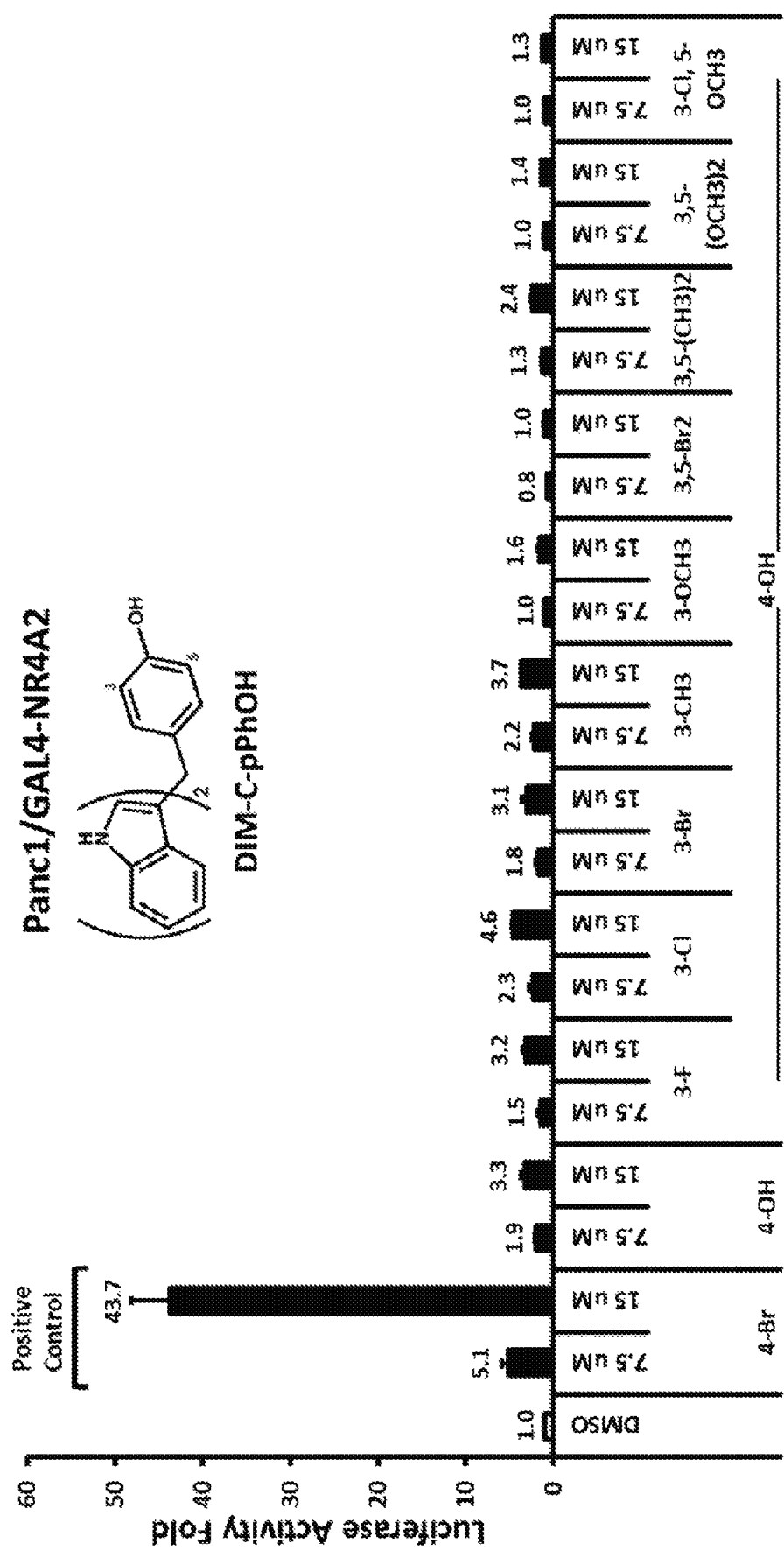
FIG. 13 graphically illustrates luciferase activity in Panc1 cells transfected with GAL4-NR4A2 and UAS-Luc treated with 3-hydroxy C-DIM analogs, according to embodiments of the present disclosure.
Figure 15:
FIG. 15 graphically illustrates luciferase activity in Panc1 cells transfected with GAL4-NR4A2 and UAS-Luc treated with 2-hydroxy C-DIM analogs, according to embodiments of the present disclosure.

The transactivation results demonstrate that the 4-, 3- and 2-hydroxy compounds all decrease transactivation in Panc1 cells transfected with GAL4-NR4A1 with a steep dose-response curve between 15 to 22.5 µM. See FIGS. 8, 7, and 6. Compared to the 4-bromo standard NR4A2 ligand, the 3- and 2-hydroxy isomers had minimal NR4A2 activity. See FIGS. 13 and 15 FIG. 3 shows that both the 2- and 3-hydroxy compounds were more potent than the 4-hydroxy compound in down-regulation of β1-integrin and TXNDC5 in Panc1 and SKBR3 cells. It is noted that the β1-actin loading control was also decreased at the higher concentrations of the 3-hydroxy (SKBR3 cells) and 2-hydroxy (SKBR3 and Panc1 cells) compounds. The results correlate with the transactivation data.

Figure 5:
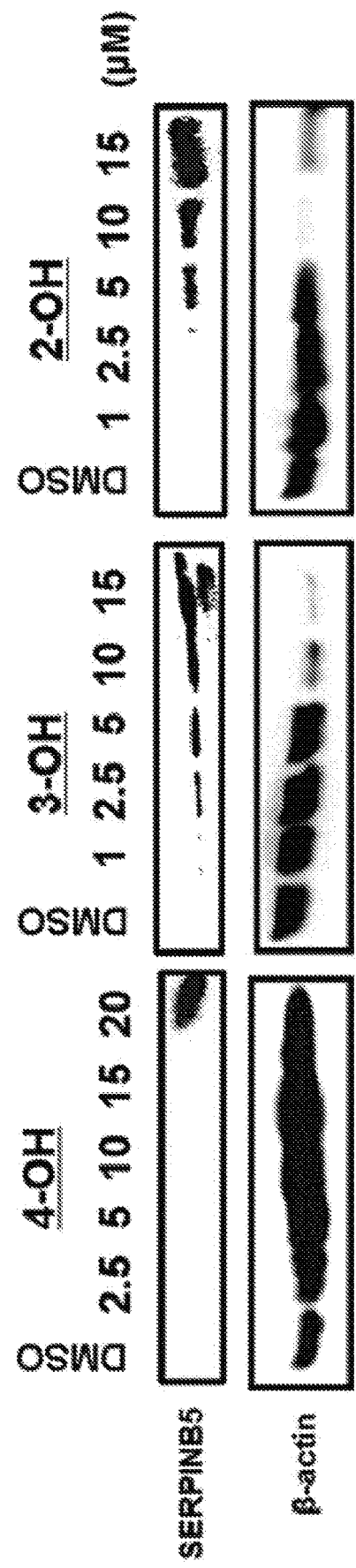
FIG. 5 includes images of western blots of SKBR3 (breast) cancer cells treated with 4-, 3- and 2-hydroxy C-DIM compounds, according to embodiments of the present disclosure, showing up-regulation of expression of SERPINB5.

Western blot analysis shows that the potencies of these 3- and 2-hydroxy CDIM compounds for inducing SERPINB5 (i.e. 2-OH/3-OH>4-OH) were similar to that observed for down-regulation of β1-integrin and TXNDC5. See, for example, FIGS. 3 and 5.

Figure 4:
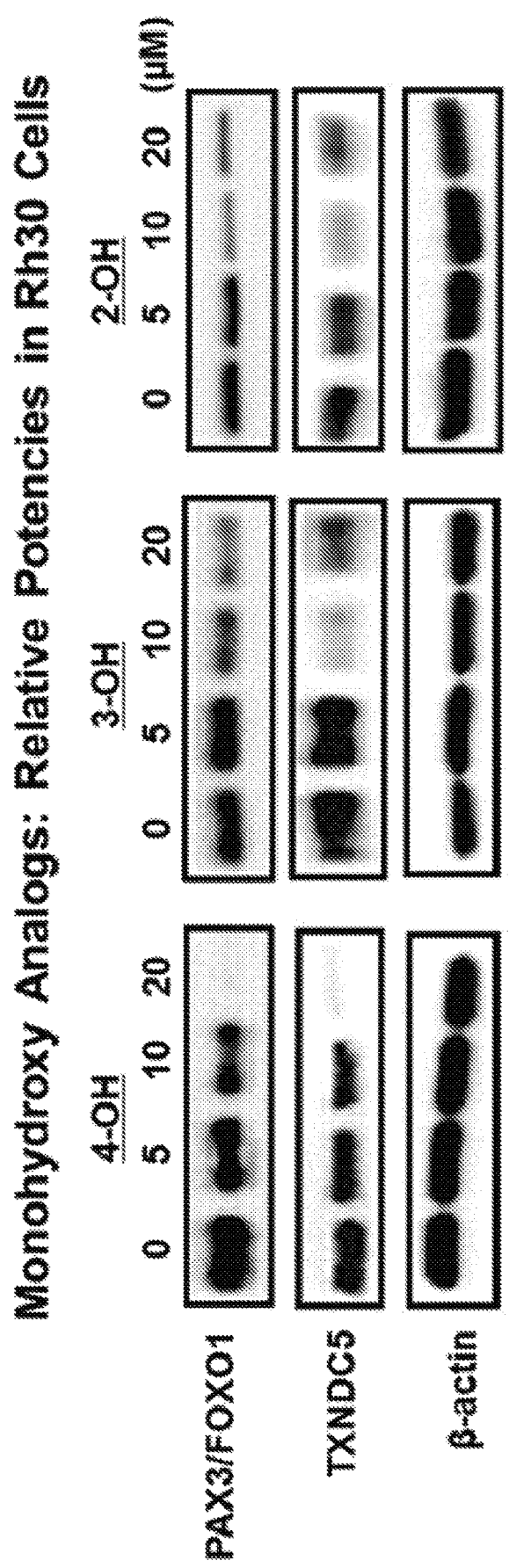
FIG. 4 includes images of western blots of Rh30 (RMS) cells treated with 4-, 3-, and 2-hydroxy C-DIM compounds, according to embodiments of the present disclosure, showing down-regulation of expression of PAX3-FOX01A and TXNDC5.

The potencies of the 2-, 3- and 4-hydroxy compounds in down-regulation of TXNDC5 and β1-integrin in Rh30 rhabdomyosarcoma cells were similar to those observed in Panc1 and SKBR3 cells. See FIG. 4.

Figure 16:
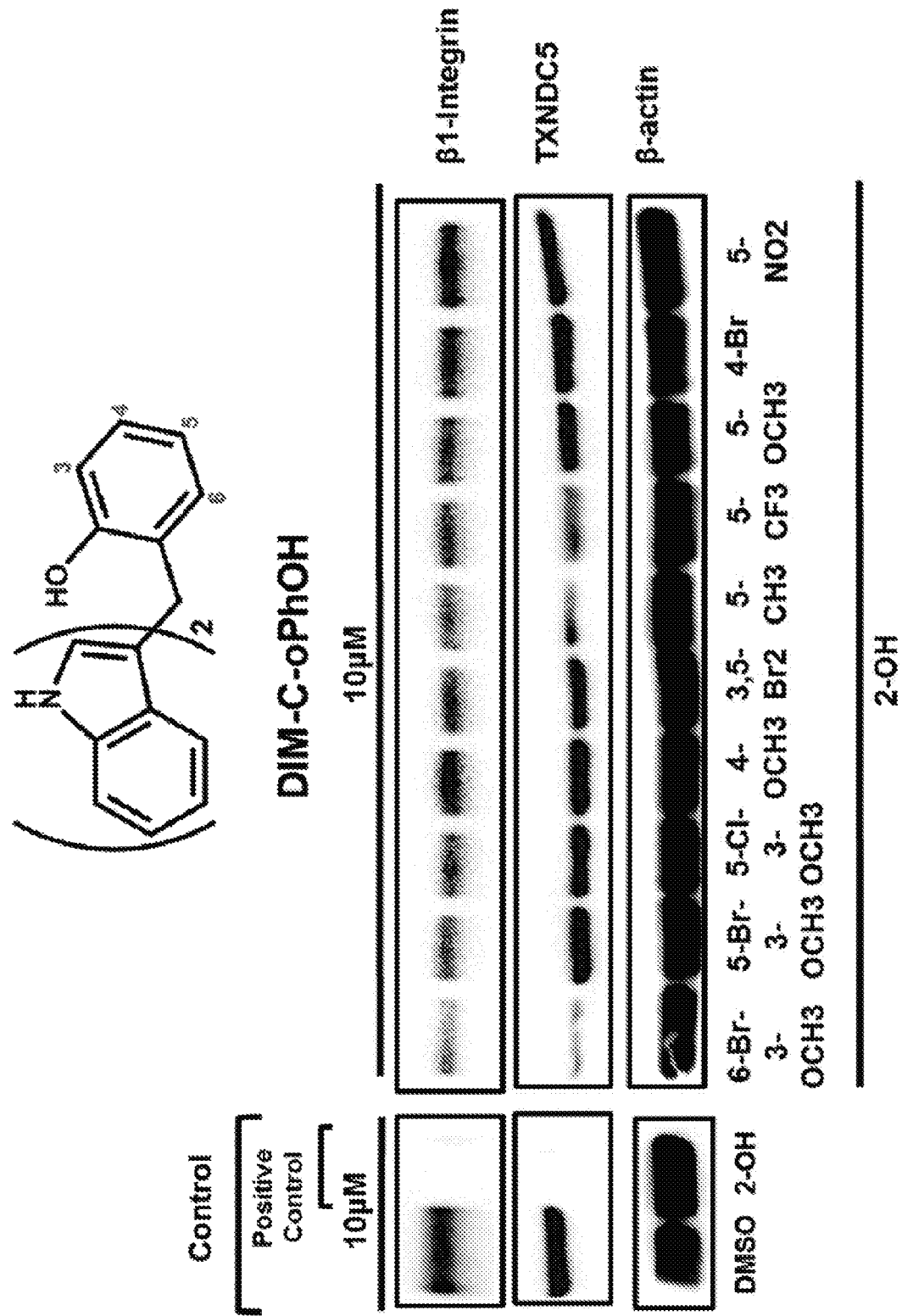
FIG. 16 includes an image of a western blot of Panc1 cells treated with 2-hydroxy C-DIM analogs, according to embodiments of the present disclosure, showing decrease in induction of TXNDC5 and β 1-integrin.
Figure 17:
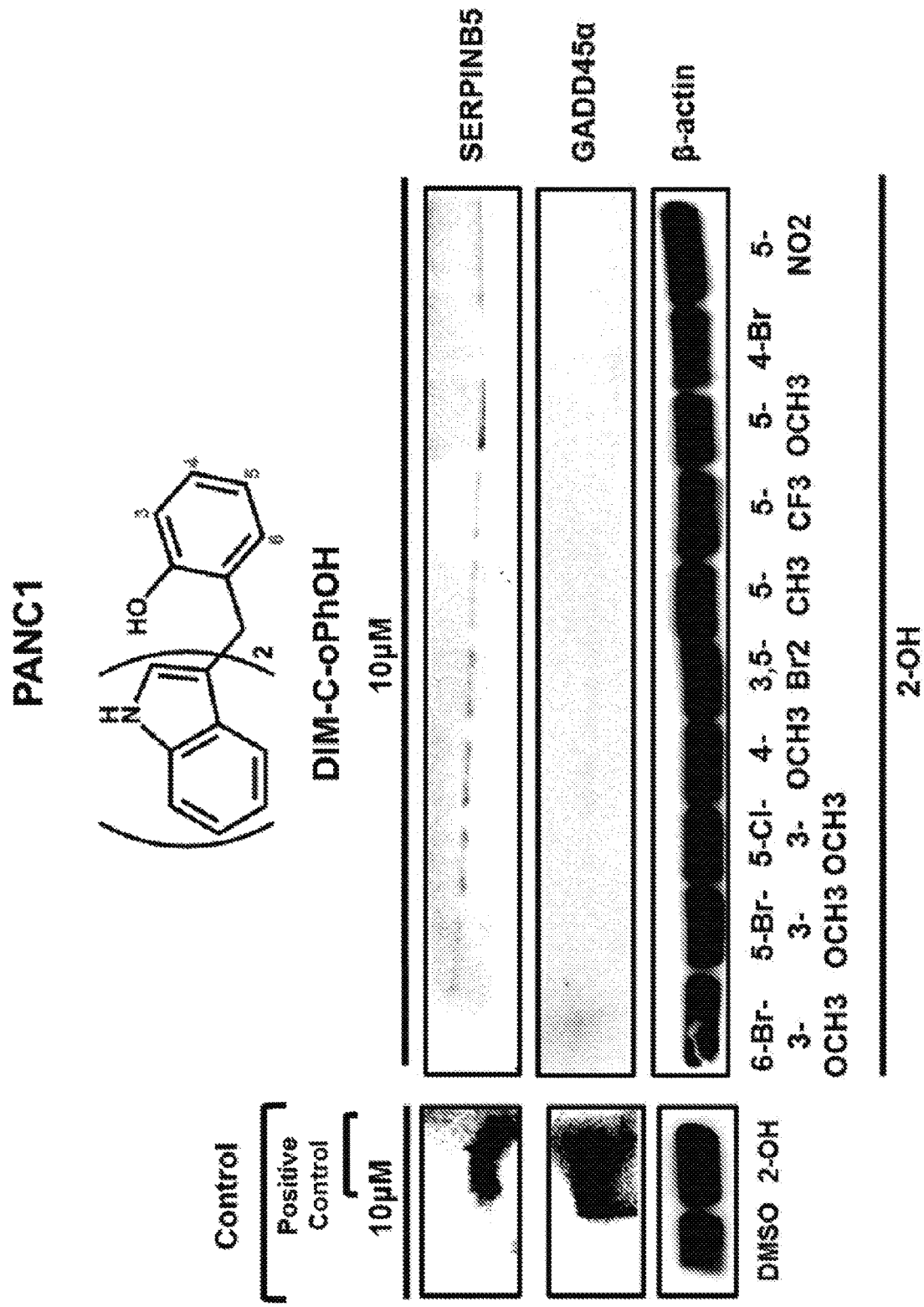
FIG. 17 includes an image of a western blot of Panc1 cells treated with 2-hydroxy C-DIM analogs, according to embodiments of the present disclosure, showing induction of SERPINB5 and GADD45α.

NR4A1 Binding and Transactivation of Substituted 2-Hydroxy and 3-Hydroxy Ligands Results obtained for the 2- and 3-hydroxy C-DIM analogs demonstrated that, in certain embodiments, they were more potent NR4A1 antagonists than the parent 4 hydroxy reference standard. Therefore, several substituted analogs of the 2- and 3-hydroxy DIMs were synthesized and investigated their activity in transactivation assays. Moreover, for the 2-hydroxy analogs, we also investigated their functional effects on gene induction (SERPINB5 and GADD45α), see FIG. 17, and repression (β1-integrin and TXNDC5), see FIG. 16.

The transactivation assays for ten 2-hydroxy analogs and their effects on NR4A1 showed that the 4-methoxy, 5-methyl and 5-methoxy derivatives decreased transactivation at concentrations similar to that observed for the parent 2-hydroxy compound. See FIG. 6.

Among this same set of substituted 2-hydroxy analog compounds, certain compounds (e.g. the 2-bromo, 5-trifluoromethyl and 3,5-dibromo) activated NR4A2, and the maximal induction response was >33% of that observed for the 4-bromo DIM reference standard. See FIG. 15.

The effects of the 2-hydroxy DIM analogs on NR4A1-dependent decreased (β1-integrin and TXNDC5—see FIG. 16) and increased (SERPINB5 and GADD45α—see FIG. 17) gene product expression in Panc1 and SKBR3 cells were investigated and compared the results with those observed for the 2-hydroxy DIM compound (unsubstituted). The results suggested that the substituted 2-hydroxy DIM compounds assayed were not significantly more active than the parent compound and this was in contrast to previous studies with the 4-hydroxy DIM and substituted analogs.

The effects of five substituted 3-hydroxy DIM analog compounds on NR4A1-dependent transactivation were also investigated in Panc1 cells. Both the 2-chloro and 2 bromo analogs were more potent than the unsubstituted 3- and 4-hydroxy DIM standards (note: the 5-hydroxy analog is equivalent to 3-hydroxy substitution). See FIG. 7.

4-Hydroxy Ligands Activate Tumor Suppressor SERPINB5

Ligands for nuclear receptors both activate and repress gene expression, and these effects are cell context-specific. Our initial studies focused on C-DIMs as NR4A1 antagonists which down-regulate pro-oncogenic genes such as β1-integrin and TXNDC5; however, C-DIMs also induce tumor suppressor gene expression in cancer cells.

Figure 10A:
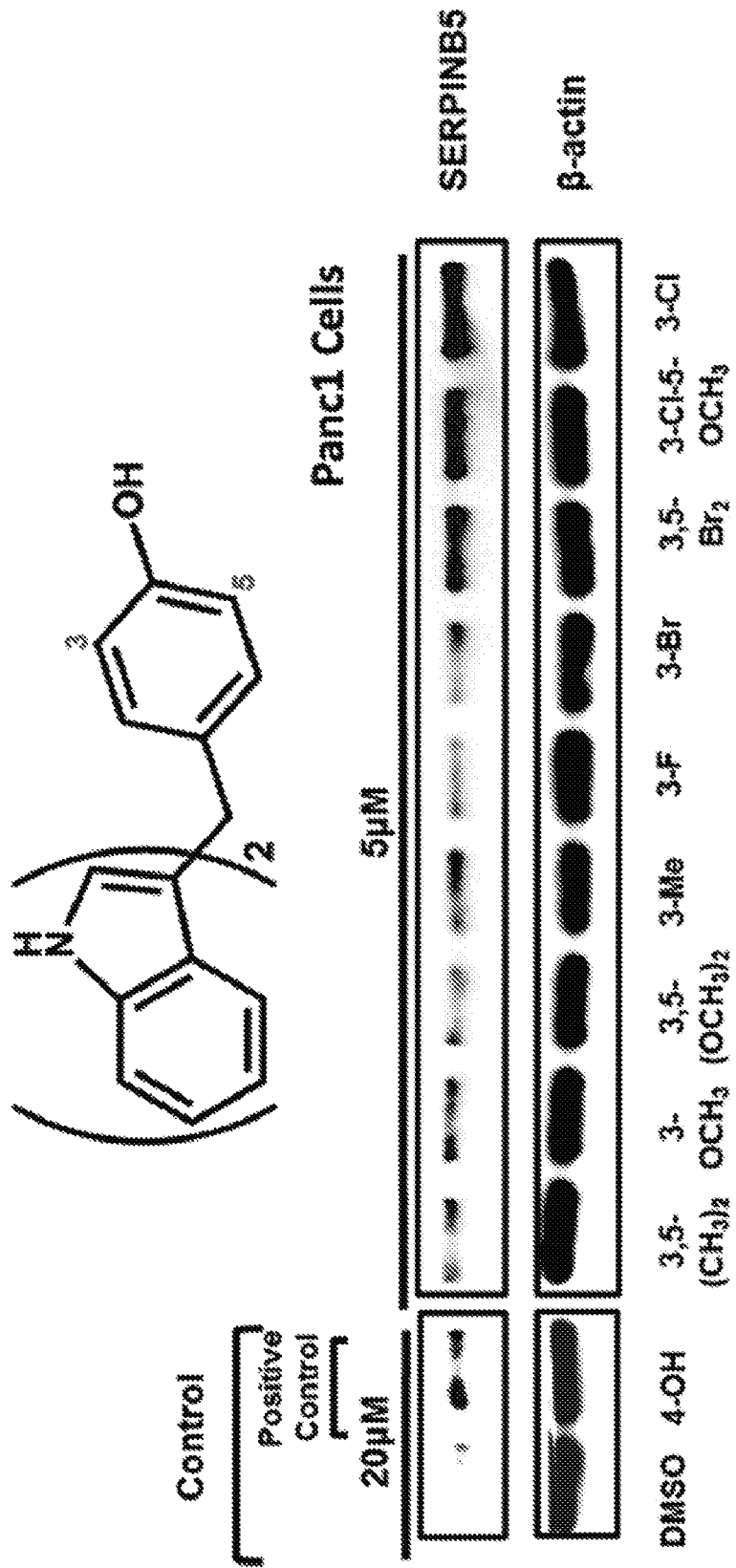
FIG. 10A includes an image of a western blot of Panc1 cells treated with 4-hydroxy C-DIM analogs (5 μM), according to embodiments of the disclosure, and with 4 OH (DIM-C-pPhOH, parent compound) showing induction of SERPINB5.
Figure 10B:
FIG. 10B includes an image of a western blot of Rh30 cells treated with 4-hydroxy C-DIM analogs (5 μM), according to embodiments of the disclosure, and with 4-OH (DIM-C-pPhOH, parent compound) showing decrease in induction of PAX3-FOX01A and TXNDC5.

In Panc1 cells, 20 µM of the 4-hydroxy positive control compound (C-DIM8) and 4 µM of the substituted analogs induced SERPINB5 (mapsin), see FIG. 10A, which is a tumor suppressor gene that suppresses cell invasion and metastasis. However, for this response in Panc1 cells, only the di-substituted 3,5-Br$_2$ and the 3-Cl-5-methoxy and the 3-Cl analogs were >4-fold more potent than the 4-hydroxy C-DIM positive control.

In SKBR3 breast cancer cells, 20 µM of the 4-hydroxy positive control compound minimally induced SERPINB5 whereas significant induction of SERPINB5 was observed in cells treated with 5 µM of the substituted 4-hydroxy analogs. See FIG. 14. In this study, the DMSO (control) value was relatively high, resulting in low induction by the 4-hydroxy compound, whereas in other experiment induction was observed due to lower basal SERPINB5 levels. Results in SKBR3 and Panc1 cells demonstrate that C-DIM analogs induce SERPINB5 with some differences in potency, and these results confirm that the 4-hydroxy substituted C-DIM analogs represent a second generation of potent NR4A1 ligands.

In Vitro and In Vivo Assays of 4-OH Ligands

The following is a description of three of the more active DIM-4-OH analogs in accordance with embodiments of the disclosure in both in vivo and in vitro assays.

Figures 12A, 12B, 12C:
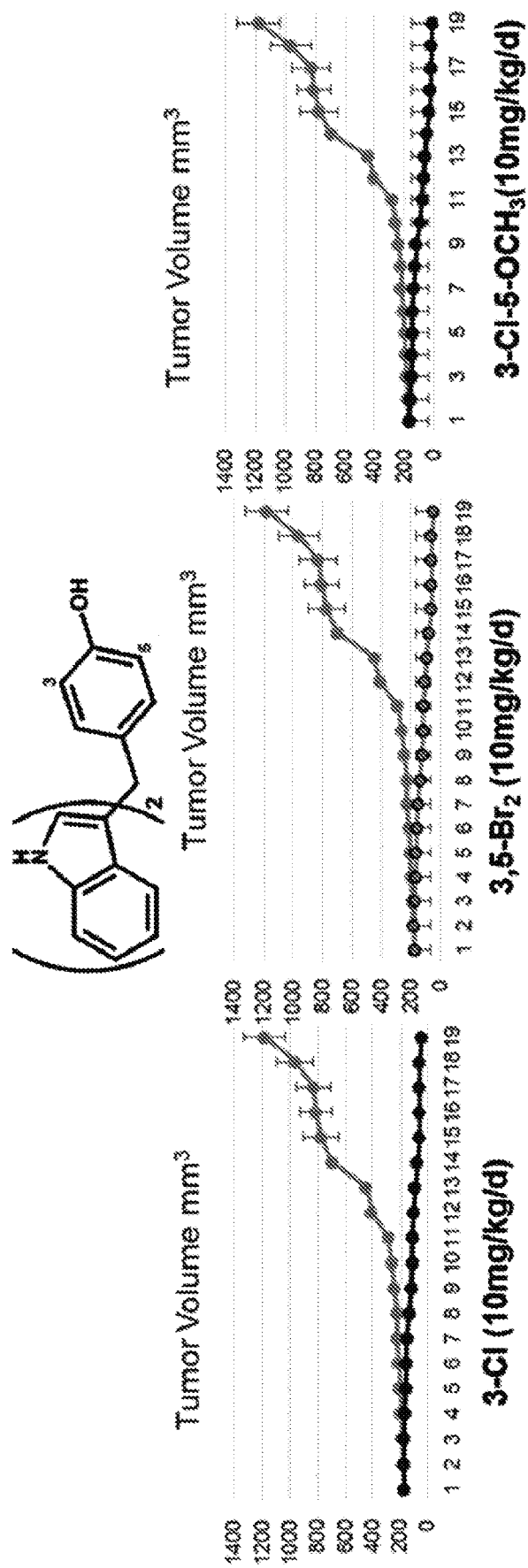
FIGS. 12A-12C graphically illustrate mammary tumor volume in an athymic nude mouse xenograft model using human MDA-MB-231 breast cancer cells treated with 4-hydroxy C-DIM analogs (10 mg/kg/day) (black) relative to a control (gray), according to embodiments of the present disclosure.

FIGS. 12A-12C summarize the in vivo tumor growth inhibition by three analogs of DIMC-pPh-OH in athymic nude mice bearing triple negative MDA-MD-231 cells in an orthotopic model (black trace) relative to a control (gray trace). The 3-chloro, 3,5-dibromo-, and 3-chloro-5-methoxy analogs of DIM-C-pPh-OH inhibited tumor growth at a dose of 10 mg/kg/day and it was evident that $ED_{50}$ values for tumor growth inhibition will be in the low mg/kg/day or high µg/kg/day range. See FIGS. 12A-12C. It is evident that the new substituted analogs represent a second generation of NR4A1 ligands, significantly more potent that DIM-C-pPh-OH, which only partially inhibited tumor growth at doses of 40-50 mg/Kg/day.

Figure 18:
FIG. 18 includes images of western blots of dissociated tumor cell lysate from an orthotopic breast cancer model treated with 4-hydroxy C-DIM analogs, according to embodiments of the present disclosure, showing inhibition of the mTOR pathway.

Tumor lysates from control and treated mice were analyzed for their effects on NR4A1-dependent responses previously characterized in in vitro studies. Lysates from individual tumors were analyzed by western blots and the three analogs (a) decreased the mTOR pathways, including phosphorylated mTOR, p70S6K, pS6RP, and p-EBP1 (see FIG. 18), (b) decreased NR4A1/Sp-regulated factors including survivin, EGFR, TXNDC5, and β1-Integrin (see FIG. 19) and (c) induced expression of NR4A1-regulated GAD045a and SERPINB5 gene products, and also induced PARP cleavage, a marker of apoptosis (see FIG. 19).

The structure-dependent induction of three NR4A1-responsive genes by DIM-C-pPhOH (DIM-4-OH) and two of the more potent DIM-C-pPhOH analogs (3-chloro- and 3,5-bibromo-) used in the in vivo studies were investigated in Rh30 cells. Three NR4A1-inducible genes, namely IL-24, GDA, and DCDC2, were identified by RNAseq. Preliminary studies showed maximal mRNA induction by the C-DIM NR4A1 ligands after 12 hours. The results (FIGS. 11A-11C) show structure dependent potency differences for the 3 NR4A1 ligands, as inducers of gene expression. Based on $EC_{50}$ values, the 3-chloro- or 3,5-dibromo analogs were up to >10× times more potent that DIM-C-pPhOH: however, these potency differences were compound and gene-dependent.

Figure 23D:
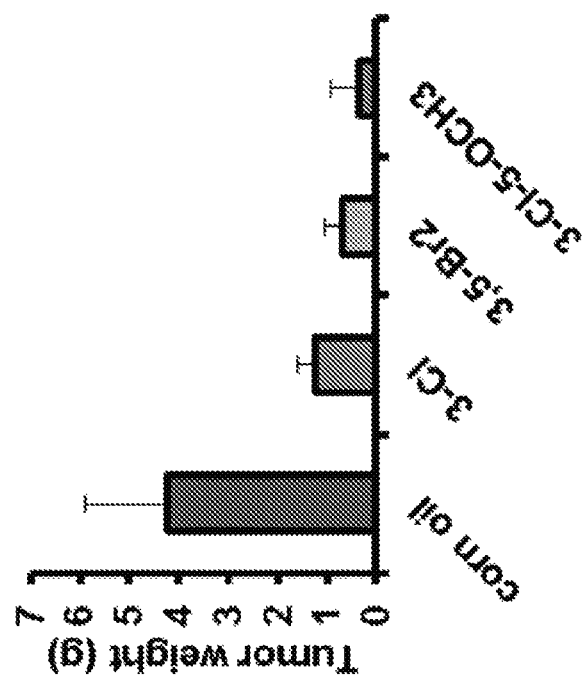
Figure 23D:

As confirmation of the in vitro SARs, FIG. 23 shows that three of the second generation C-DIM/NR4A1 ligands completely inhibit mammary tumor growth at a dose of 5 mg/kg/day, which is significantly lower than previous studies where 30-40 mg/kg/day of DIM-C-pPhOH (C-DIM8) only partially (40-50%) inhibited tumor growth.

Figures 24C, 24D:
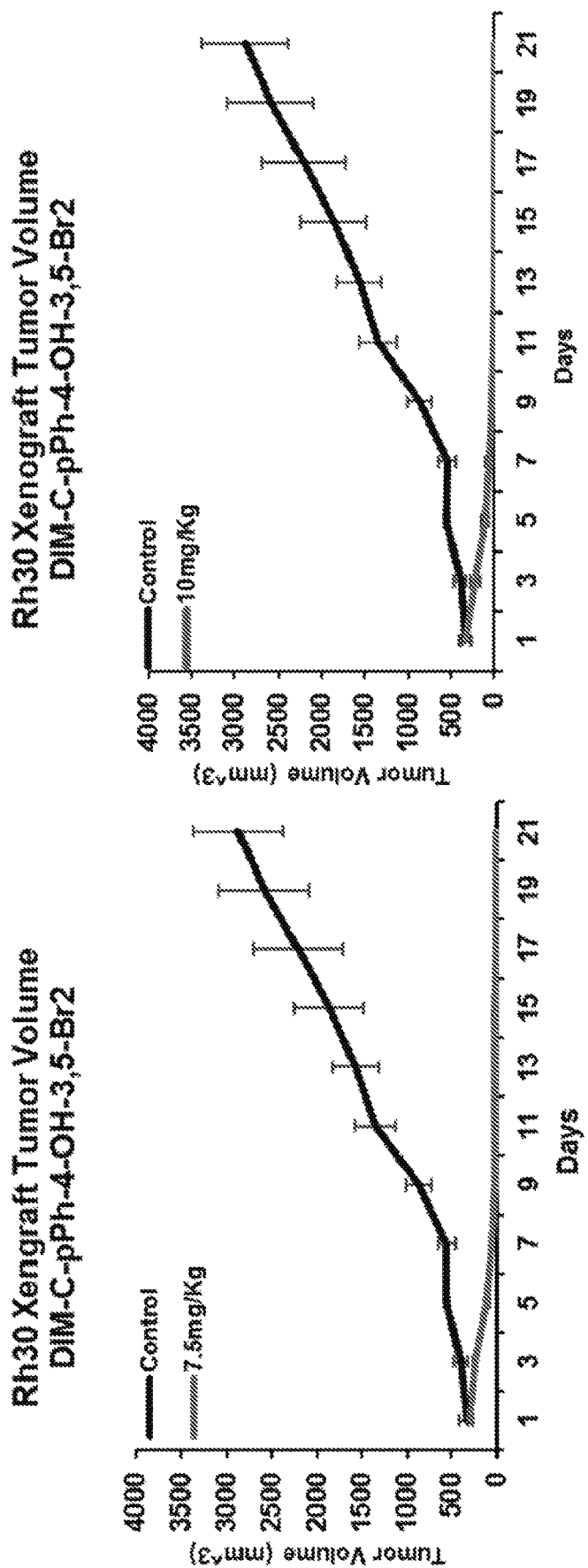
Figures 25A, 25B:
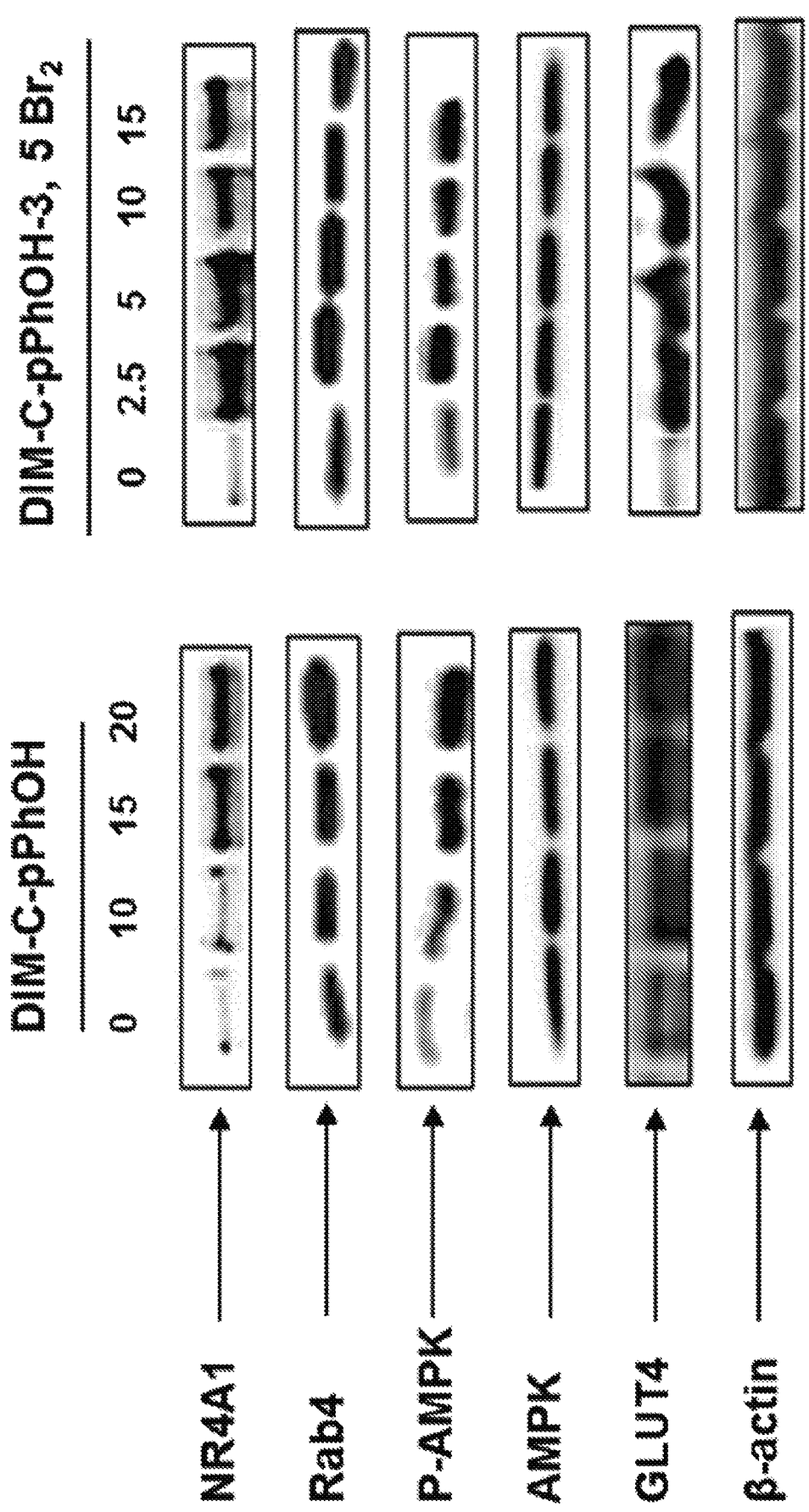
FIGS. 25A-25D are images of western blots of whole cell lysates of C2C12 cells treated with C-DIM analogs, according to embodiments of the present disclosure.
Figures 25C, 25D:
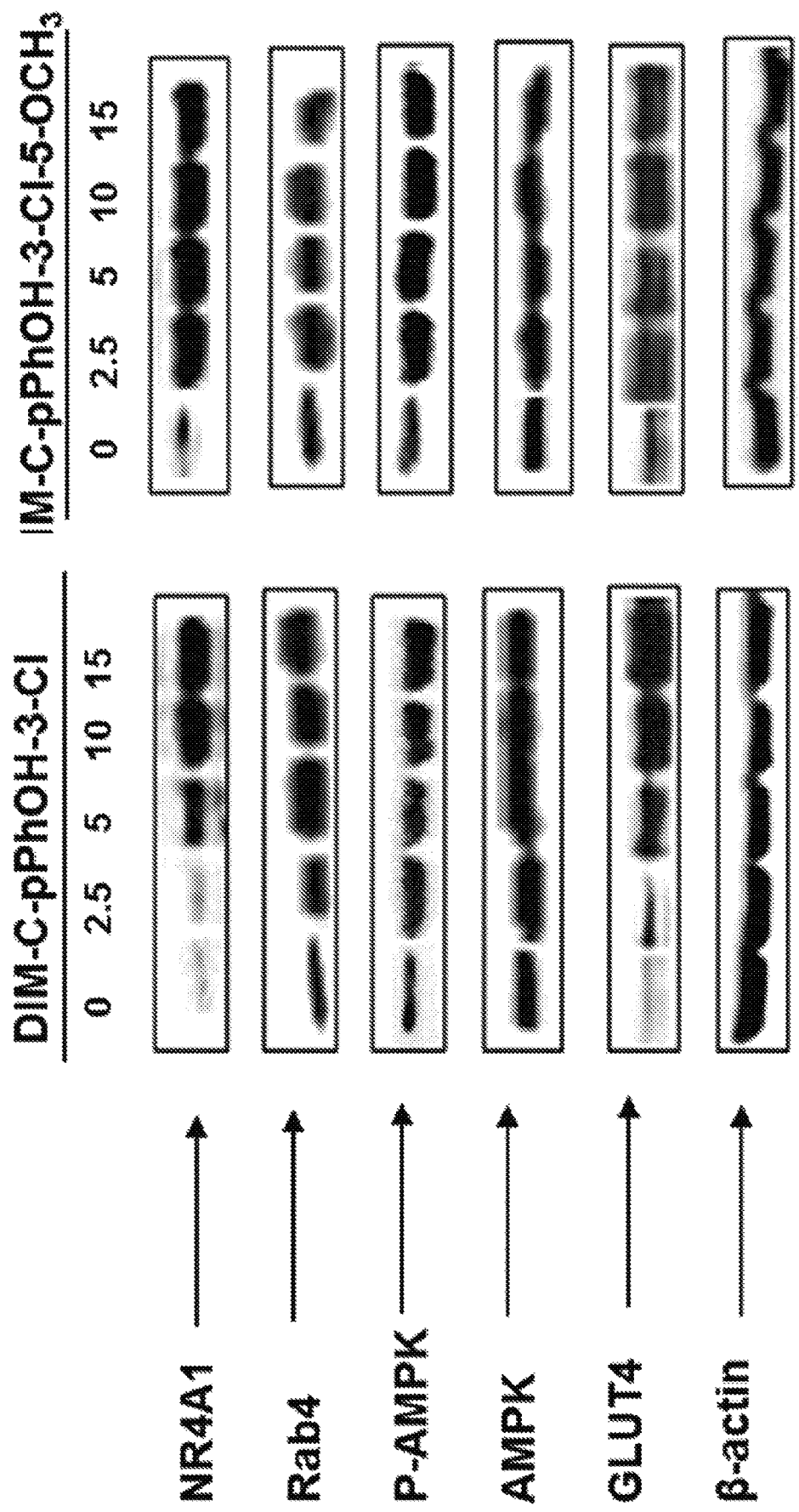
Figure 26B:
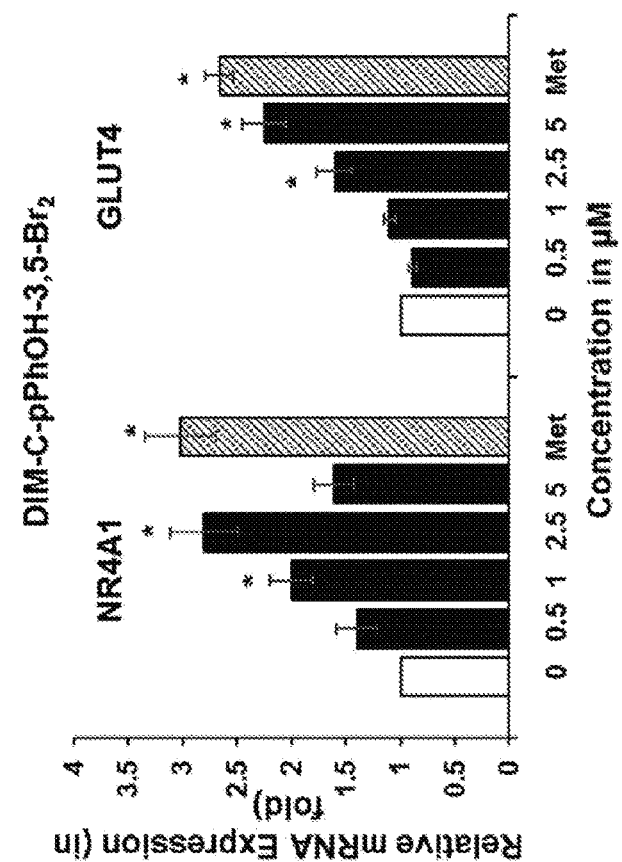
FIGS. 26A-26D graphically illustrate relative NR4A1/glucose transporter 4 (GLUT-4) mRNA expression in C2C12 cells treated with C-DIM analogs, according to embodiments of the present disclosure.
Figure 26A:
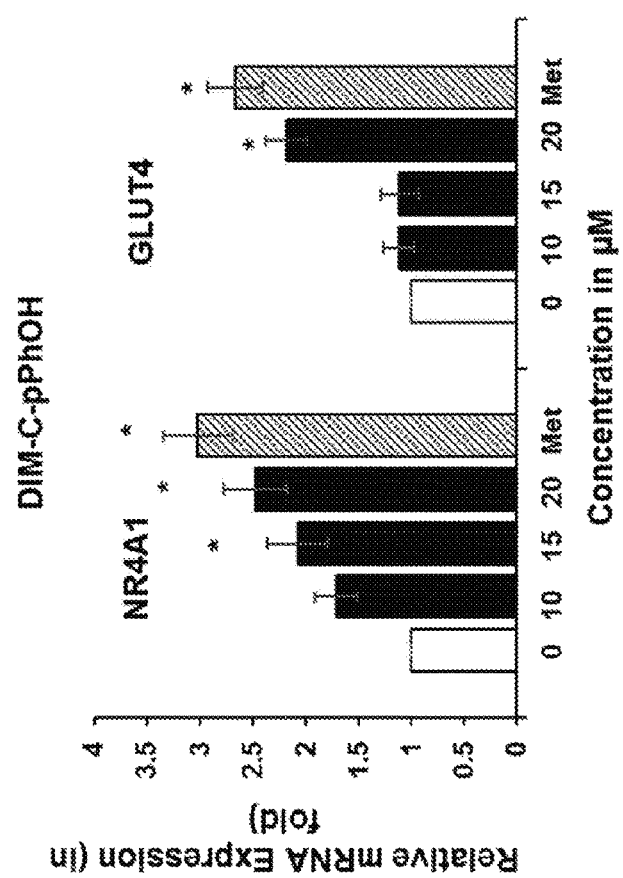
Figure 26D:
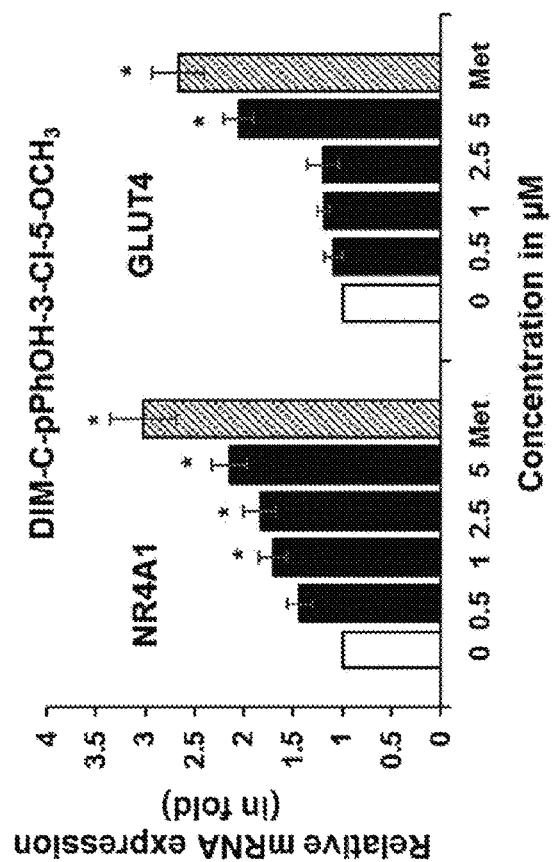
Figure 26C:
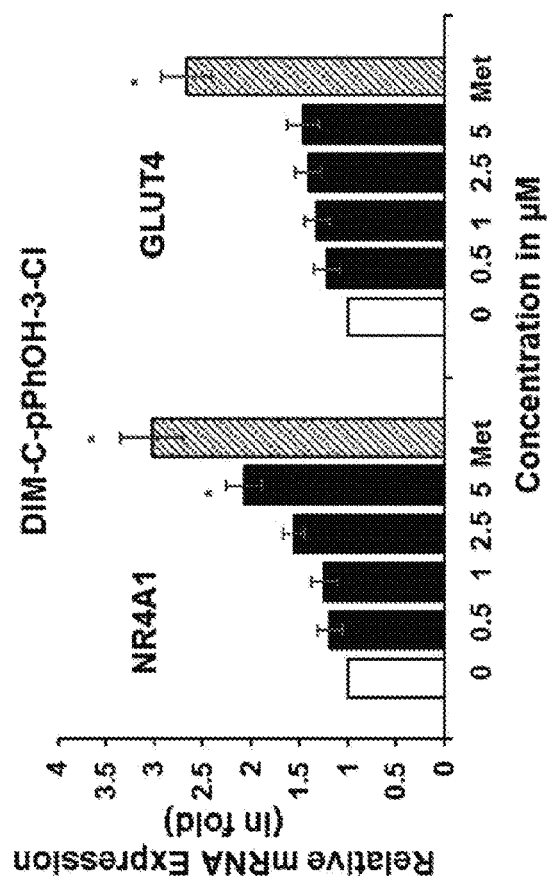

FIG. 24 summarizes results of a mouse xenograft study with the 3,5-dibromo second generation C-DIM/NR4A1 ligand and at doses of 10.0, 7.5, 5.0 and 2.5 mg/kg/day, there was complete tumor growth inhibition of RMS tumor growth. In both in vivo studies, toxicity was not observed, and an in vivo study showed RMS tumor growth inhibition at a dose of 0.25 mg/kg/d. Thus the in vitro GAL4-NR4A1 screening assay is highly predictive of both in vitro and in vivo NR4A1-dependent anticancer activity, and preliminary results with murine muscle cells (C2C12) indicate that the SARs for cancer are comparable to those for modulating NR4A1-mediated metabolic activity.

Glucose Uptake of C2C12 Cells Treated with Substituted NR4A1 Ligands

The following is a description of glucose uptake by cells treated with compounds in accordance with embodiments of the disclosure.

Previous studies show that NR4A1 regulates genes associated with glucose metabolism in C2C12 muscle cells and also enhances expression of GLUT-4. Moreover, mice with GLUT-4 knockdown in muscle cells are insulin resistant, indicating that drugs that increase GLUT-4 expression in muscle are potential anti-diabetic agents. There is also evidence that NR4A1 plays a role in enhancing glucose metabolism in muscle and this is consistent with potential anti-diabetic activity for NR4A1 ligands which has previously been reported for cytosporone-derived NR4A1 ligands in mouse models. Initial studies with DIM-C-pPhOH and second generation substituted analogs used C2C12 muscle cells as a model for investigating the anti-diabetic activity of these compounds. FIGS. 25A-25D illustrate that NR4A1 is expressed in C2C12 cells and treatment with C-DIM8 (DIM-C-pPhOH) and the second generation substituted C-DIM8 analogs 3,5-dibromo-(C-DIM8-3,5-Br$_2$), 3-chloro-(C-DIM8-3-Cl), and 3-chloro-5-methoxy-(C-DIM8-3-Cl-5-OCH$_3$) increased expression of NR4A1 in C2C12 cells. In addition, we also observed enhanced expression of Rab4 and activation (phosphorylation) of AMPK and similar results have been observed for the anti-diabetic drug metformin in C2C12 cells. Results illustrated in FIGS. 26A-26D show that both DIM-C-pPhOH (C-DIM8) and metformin induce NR4A1 and GLUT-4 gene expression in C2C12 cells and maximal induction was observed after treatment with 20 μM DIM-C-pPhOH. The second generation substituted compounds induced similar responses at concentrations from 2.5 to 5.0 μM.

Figure 27:
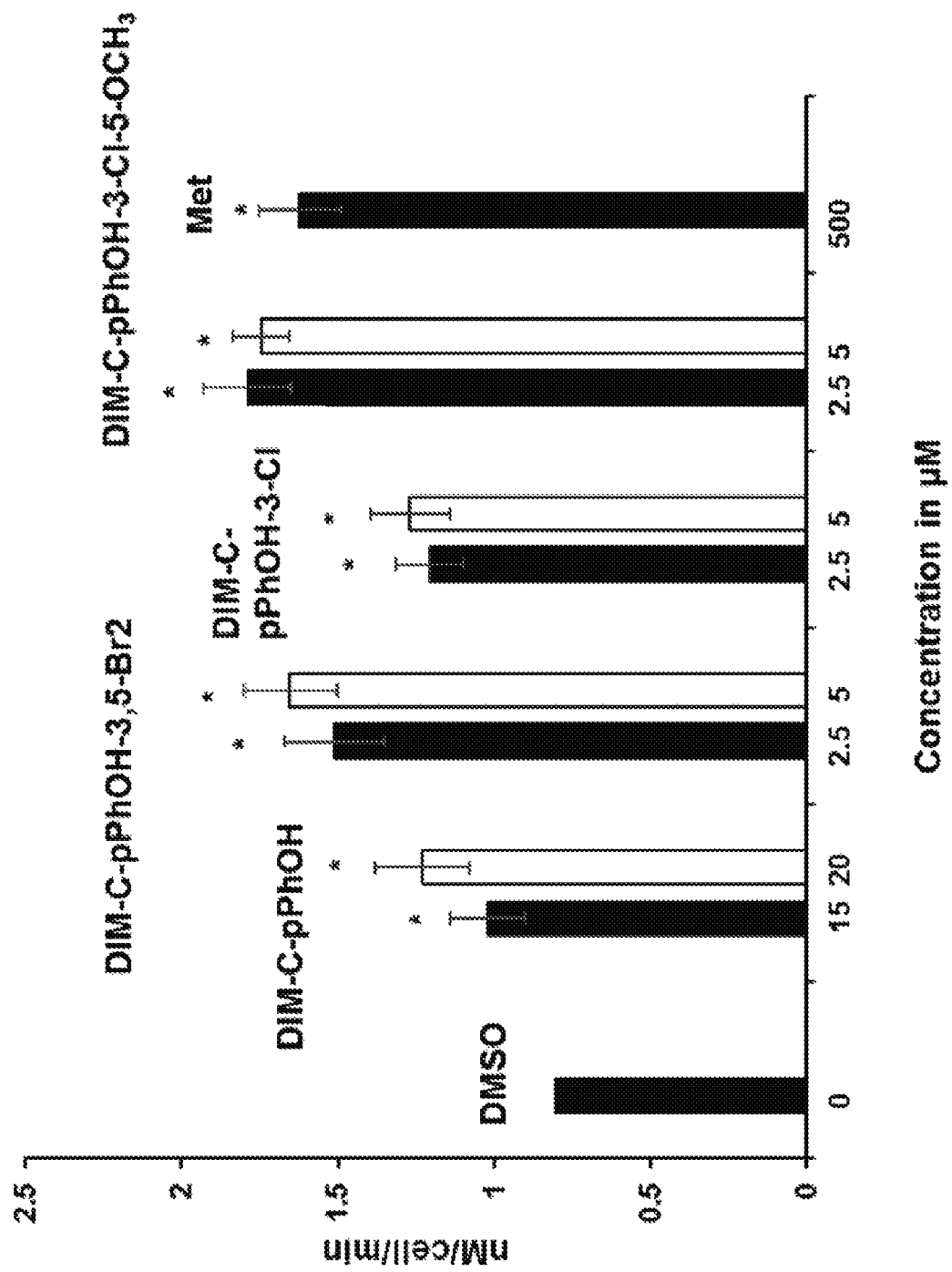
FIG. 27 graphically illustrates glucose uptake in C2C12 cells treated with C-DIM analogs, according to embodiments of the present disclosure.

The effects of DIM-C-pPhOH and the three substituted analogs on glucose uptake in C2C12 cells were investigated (FIG. 27), and it was observed that DIM-C-pPhOH (15 and 20 μM) and the substituted analogs (2.5-5.0 μM) significantly induced glucose uptake. The responses observed for C-DIM8-3,5-Br$_2$ and C-DIM8-3-Cl-5-OCH$_3$ were similar to that observed for 500 μM metformin.

Figure 28A:
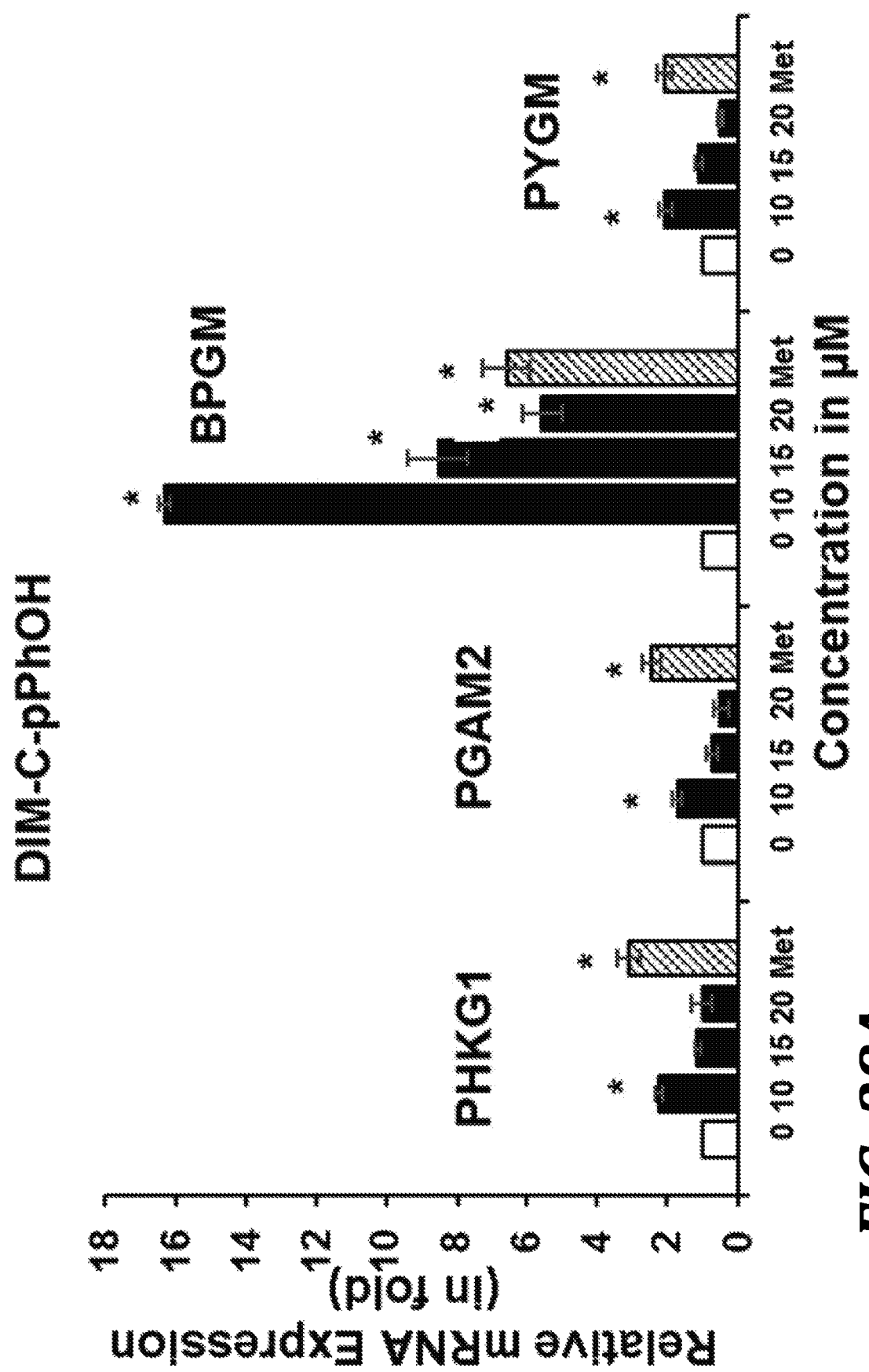
FIGS. 28A-28E graphically illustrate relative mRNA expression of glycolytic genes in C2C12 cells treated with DIM-C-pPhOH (A), DIM-C-pPhOH-3,5-Br$_2$ (B), DIM-C-pPhOH-3-Cl (C), and DIM-C-pPhOH-3-Cl-5-OCH$_3$ (D) for 24 hr, or cells were transfected with NR4A1 expression plasmid (E)
Figure 28B:
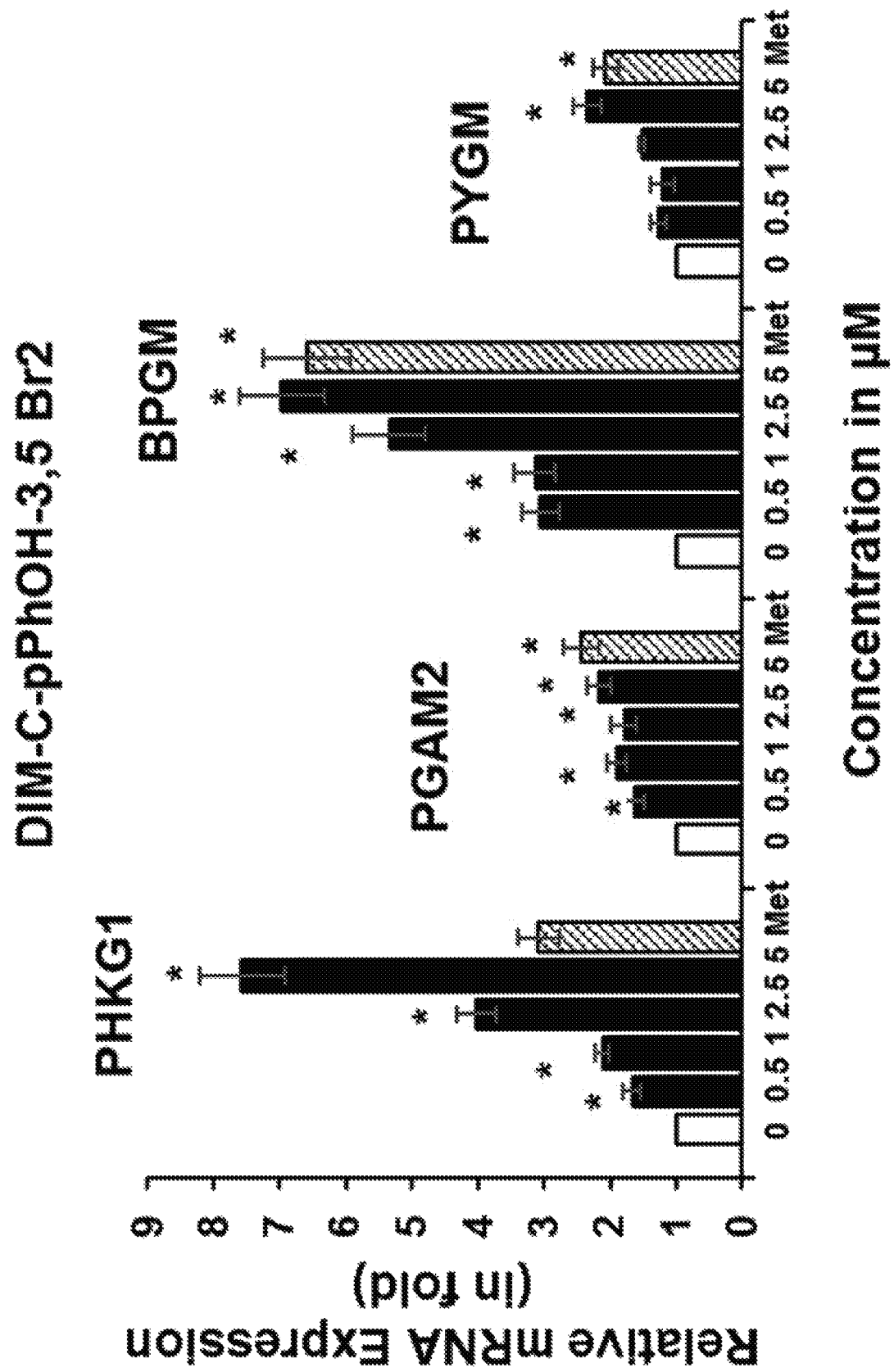
Figure 28C:
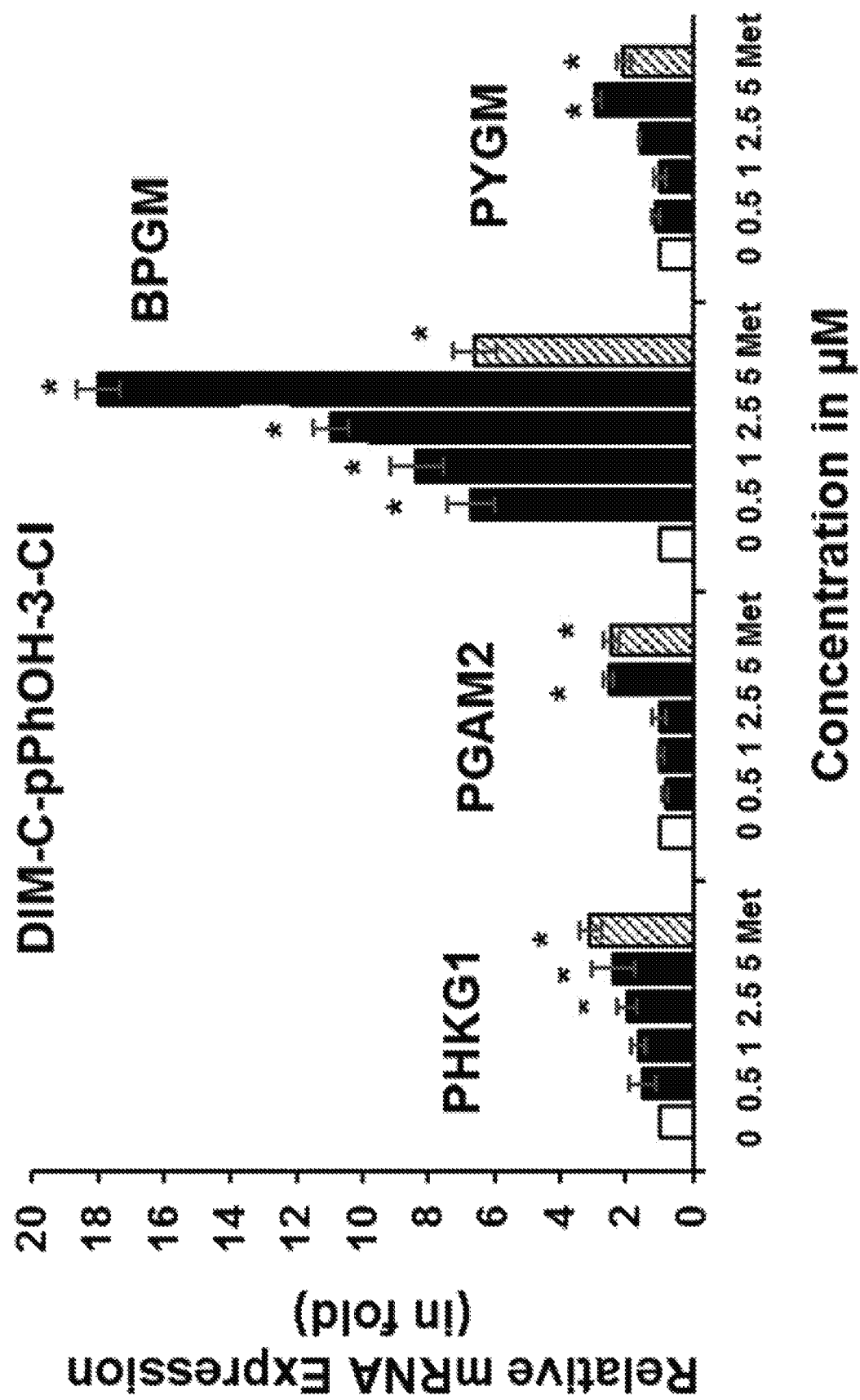
Figure 28D:
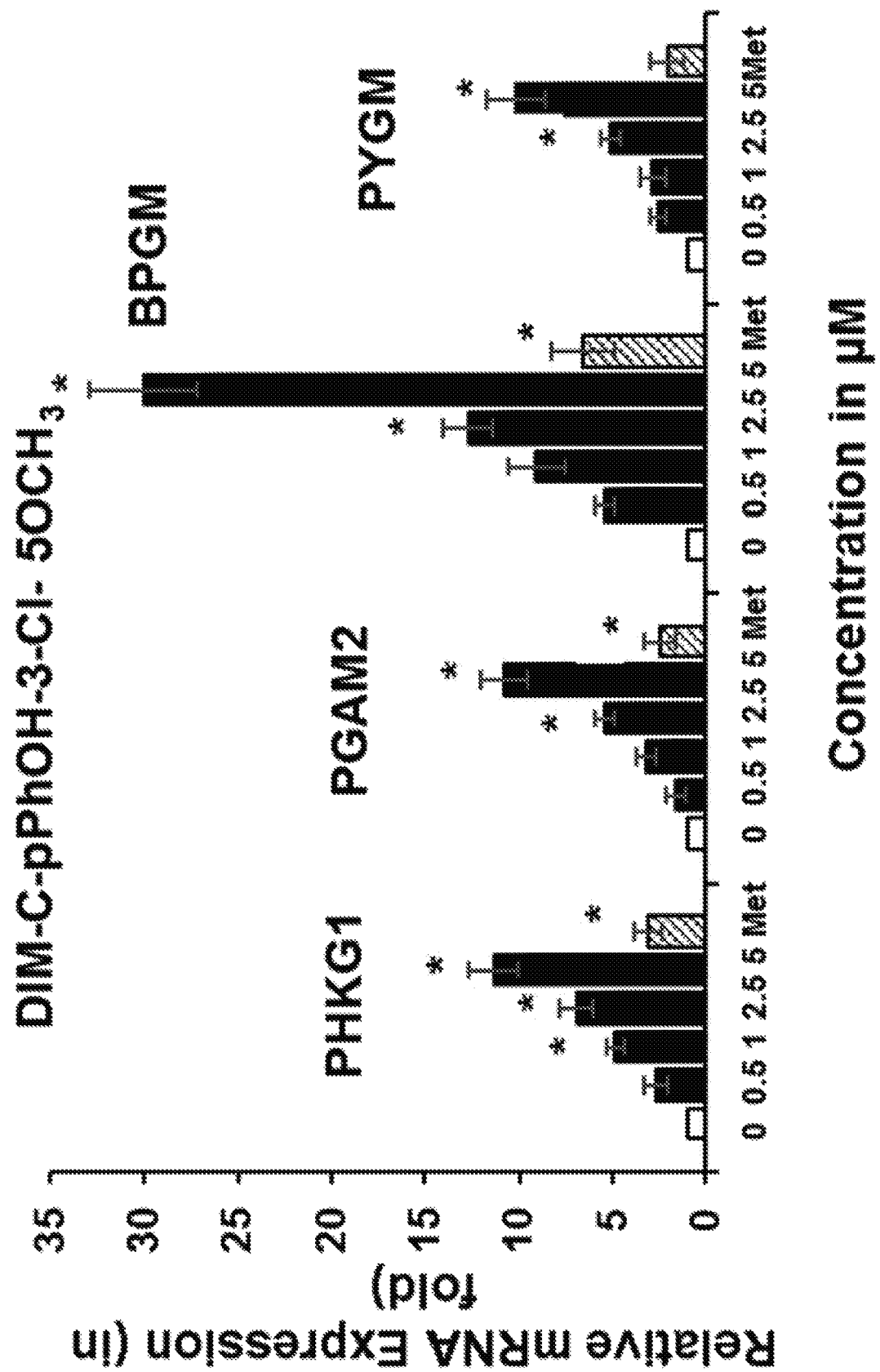
Figure 28E:
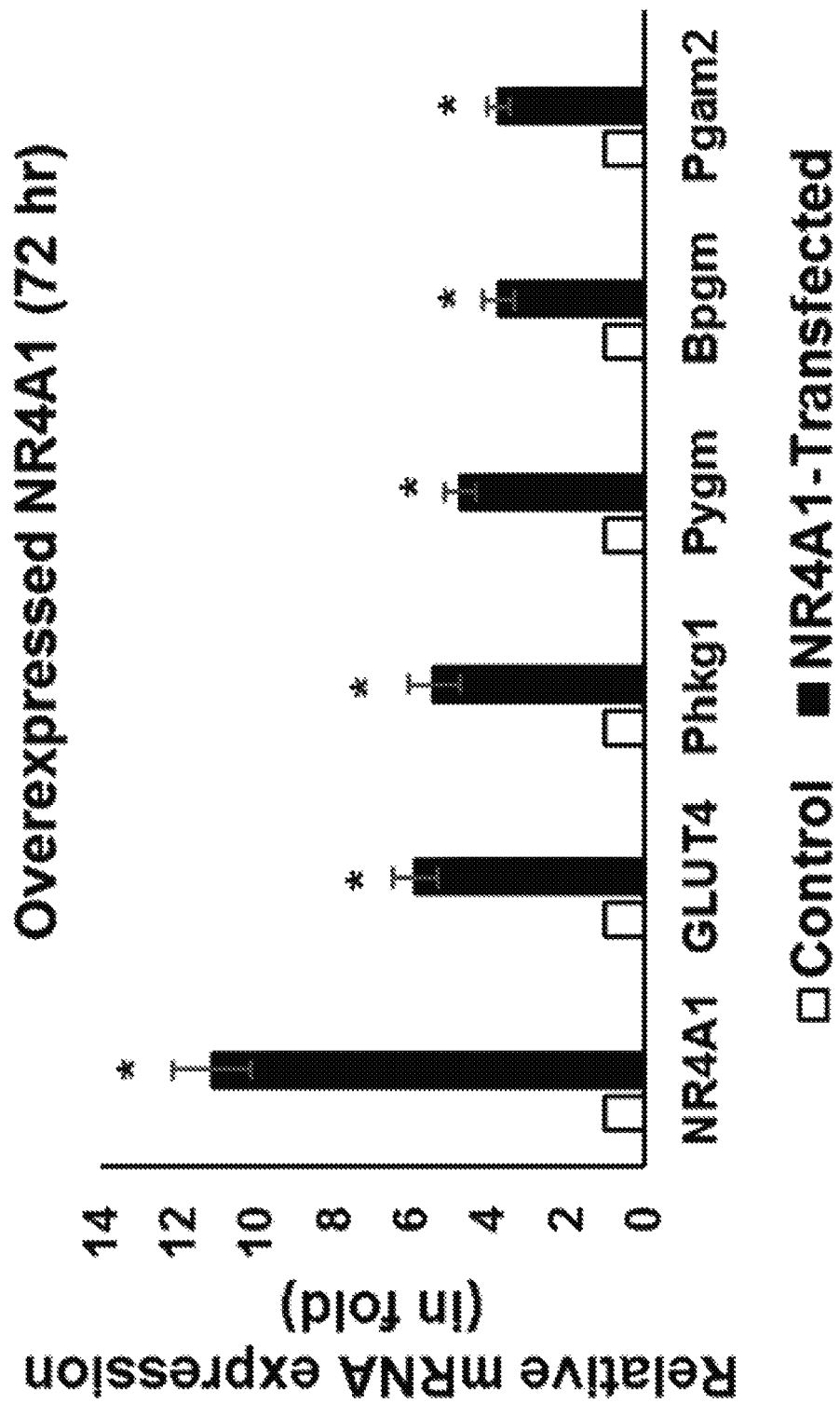

Overexpression of NR4A1 in C2C12 cells induces several genes involved in glycolysis including phosphofructokinase (PFKM), phosphoglycerate mutase 2 (PGAM2), bisphosphoglycerated mutase (BPGM), and glycogen phosphorylase M (PYGM). Treatment of C2C12 cells with the NR4A1 ligands and metformin significantly induced expression for all genes and similar induction responses were observed after overexpression of NR4A1 in C2C12 cells (FIG. 28E). These results (FIGS. 25-28) demonstrate that DIM-C-pPhOH and the substituted analogs induce glucose uptake and glycolysis in C2C12 muscle cells and represent a novel class of anti-diabetic drugs that act through NR4A1.

Figure 20A:
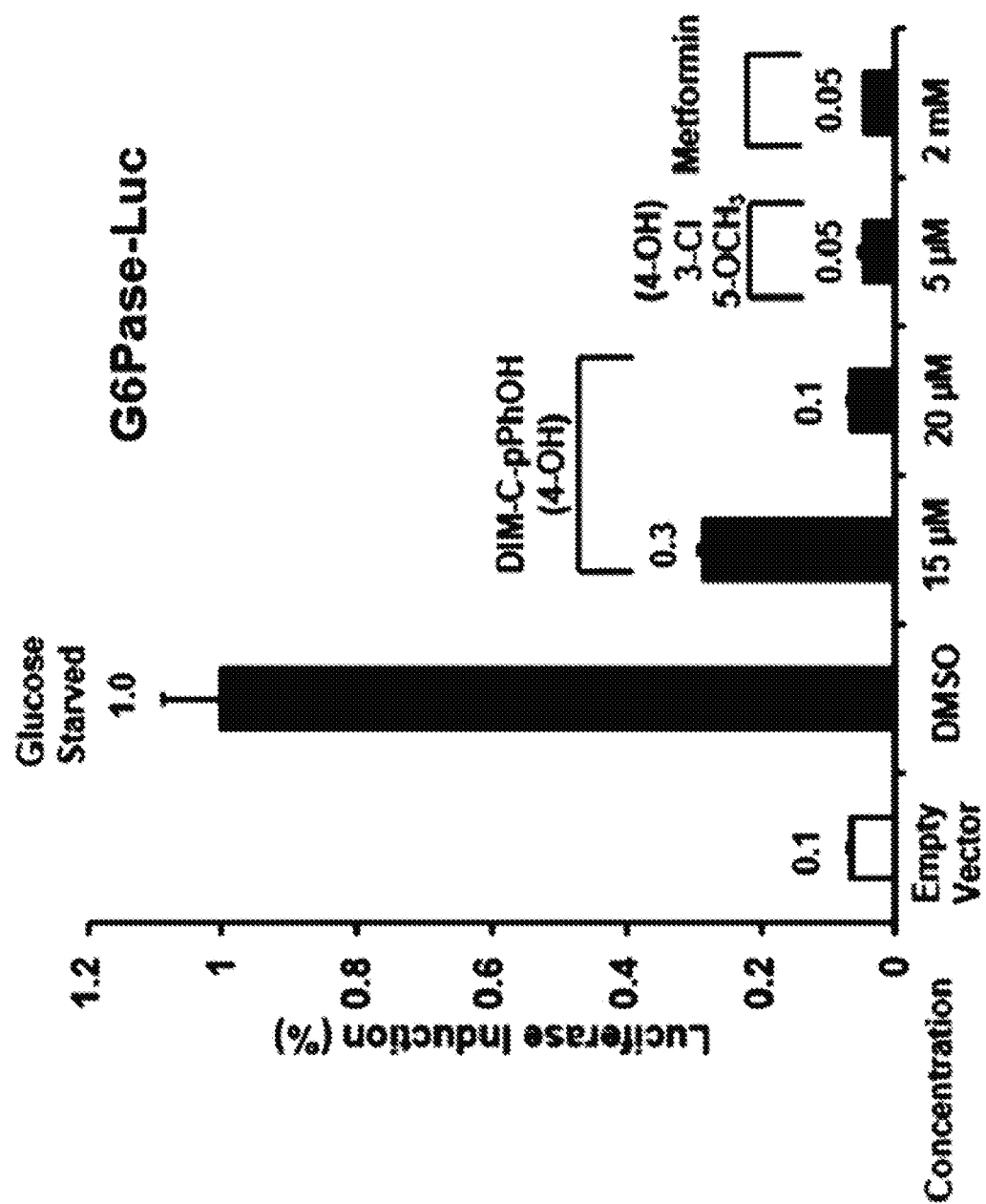
FIG. 20A graphically illustrates luciferase activity in glucose-starved HepG2 cells treated with a C-DIM analog, according to an embodiment of the present disclosure, demonstrating a down-regulation of G6Pase.
Figure 20B:
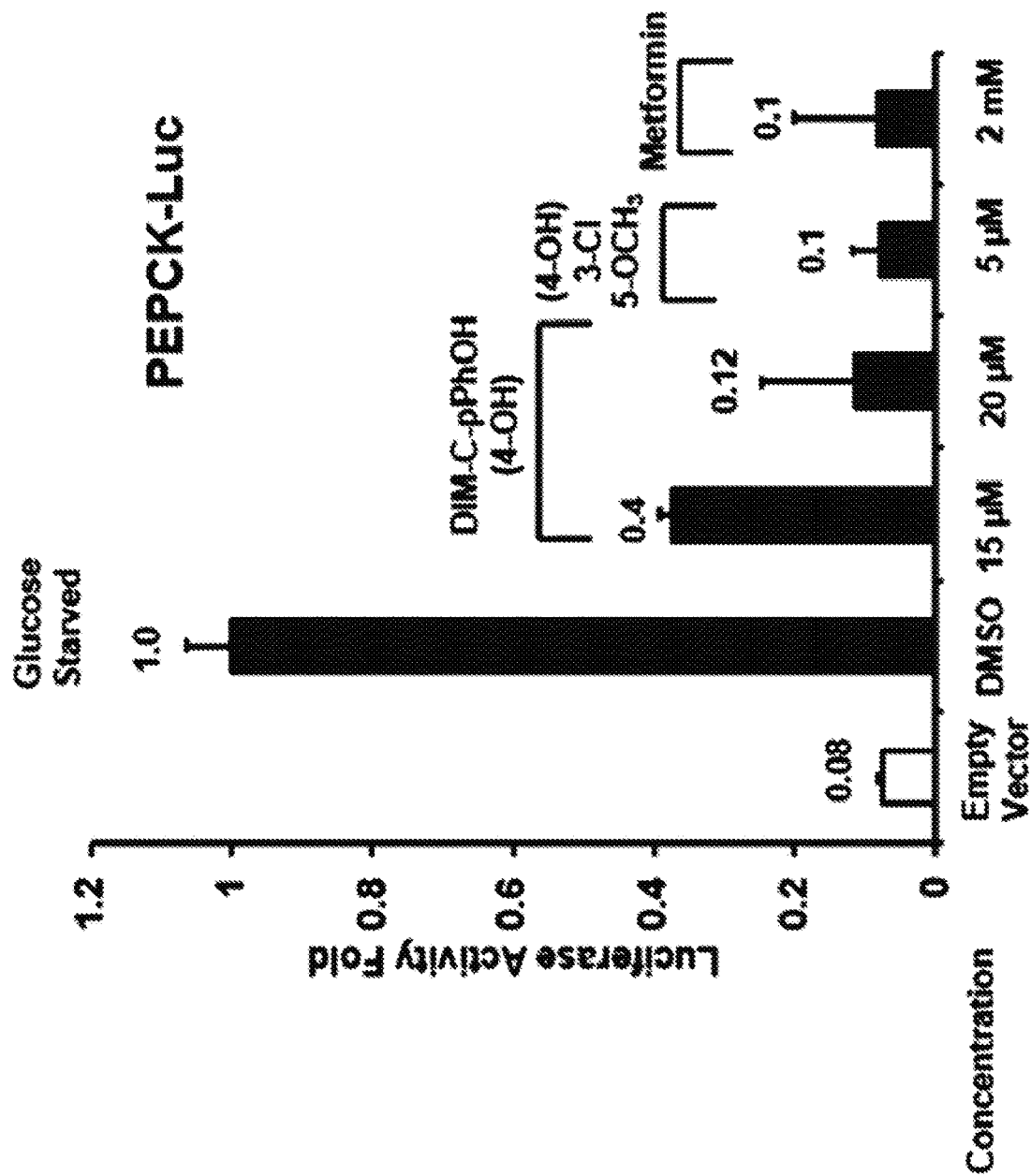
FIG. 20B graphically illustrates luciferase activity in in glucose-starved HepG2 cells treated with a C-DIM analog, according to an embodiment of the present disclosure, demonstrating a down-regulation of PEPCK.

FIG. 20 summarizes results in glucose-starved HepG2 cells which exhibit enhanced gluconeogenesis. DIM-C-pPhOH (C-DIM8) and the 3,5-dibromo analog inhibit G6Pase and PEPCK mRNA levels and results suggest that the mechanism involves NR4A1/AMPK-dependent inhibition of mTOR; however, the role of LKB/NR4A1 interactions may differ from that previously published.

These data demonstrate that the C-DIM analogs are selective receptor modulators of NR4A1, as they act in an agonistic fashion in diabetic models, whereas they act in an antagonistic fashion in tumor models.

Treatment of Mice Maintained on a High-Fat Diet with Substituted NR4A1 Ligands

The following is a description of mice maintained on a high-fat diet treated with compounds in accordance with embodiments of the disclosure.

Figure 29A:
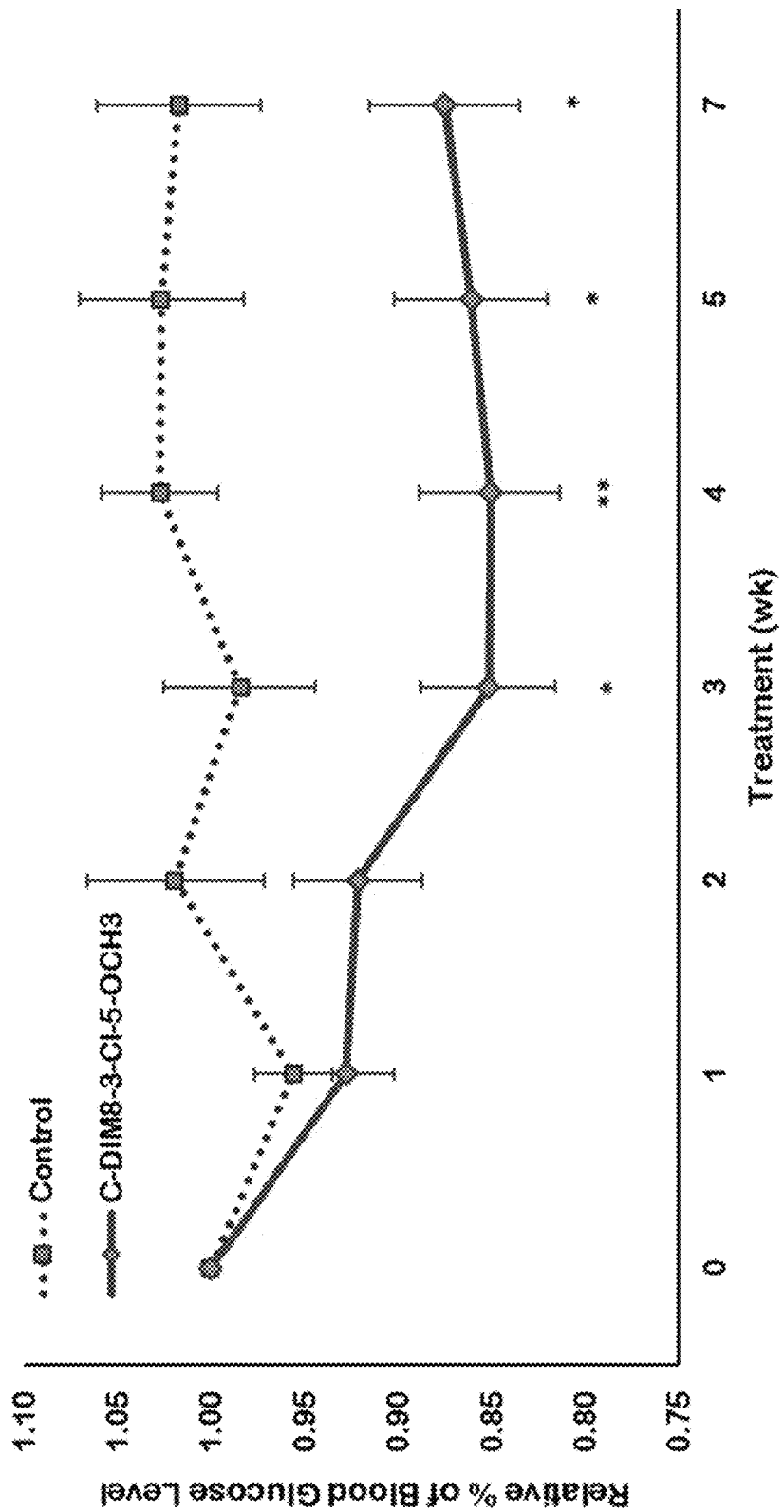
FIG. 29A graphically illustrates relative percent of blood glucose in mice treated with a vehicle control and C-DIM8-3-Cl-5-OCH$_3$ (10 mg/kg/d), according to an embodiment of the present disclosure.
Figure 29B:
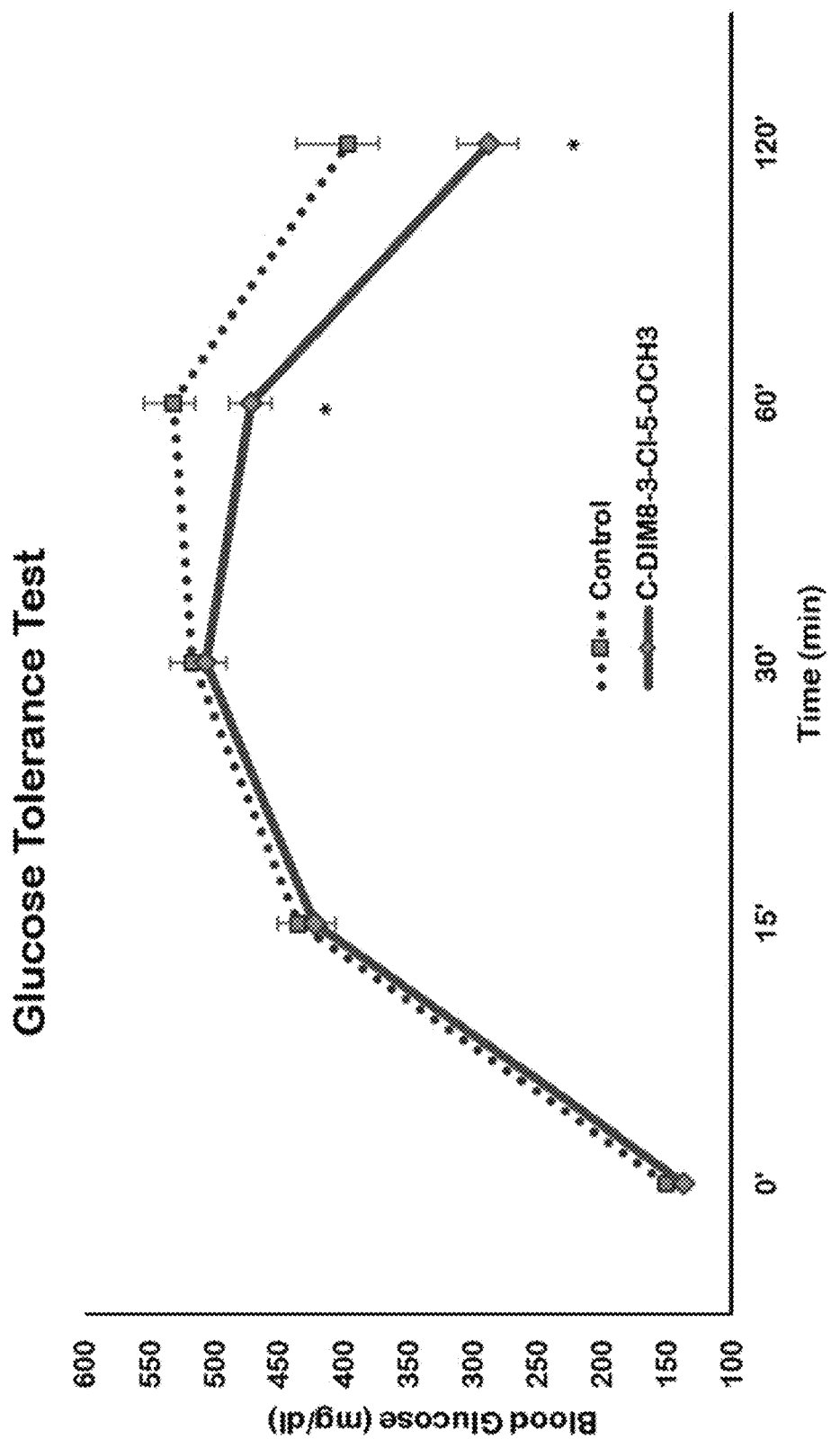
FIG. 29B graphically illustrates a decrease in blood glucose levels in a glucose tolerance levels in HFD-fed C57BL/6 mice treated with a vehicle control and C-DIM8-3-Cl-5-OCH$_3$, according to an embodiment of the present disclosure

C57BL/6 mice were maintained on a high-fat diet for several weeks and then treated with C-DIM8-3-Cl-5-OCH$_3$ (10 mg/kg/d in corn oil) every second day by oral gavage. Blood glucose was examined at several intervals over the treatment period and observed a significant decrease in blood glucose levels (FIGS. 29A and 29B). In addition, it was observed that mice treated with C-DIM8-3-Cl-5-OCH$_3$ (10 mg/kg/d) also exhibited decreased serum glucose levels compared to control animals in a glucose tolerance test and in a current study (25 mg/kg/d) we observed decreased serum glucose and increased serum insulin levels. These results are also typically observed for anti-diabetic drugs and confirms that the C-DIM8 analogs exhibits anti-diabetic activity and this in vivo data complements results of the in vitro studies, confirming that C-DIM8 and related substituted analogs represent a novel class of NR4A1-dependent anti-diabetic agents.

It will be understood that any embodiment, characteristic, element, definition, or general description provided for any aspect of the disclosure can be applied to any other aspect of the disclosure without limitation, unless explicitly stated. Thus, any embodiment discussed herein can be implemented with respect to any method, agent, or composition of the invention, and vice versa. Furthermore, agents and compositions of the invention can be used to achieve methods of the invention.

The use of the word "a" or "an," when used in conjunction with the term "comprising" herein can mean "one," but it is also consistent with the meaning of "one or more," "at least one," and "one or more than one."

The use of the term "or" is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. As an alternative to or in addition to "comprising," any embodiment herein can recite "consisting of." The transitional phrase "consisting of" excludes any element, step, or ingredient not specified in the claim. Words using the singular or plural number also include the plural and singular number, respectively. Additionally, the words "herein," "above," and "below," and words of similar import, when used in this application, shall refer to this application as a whole and not to any particular portions of the application.

Publications cited herein and the subject matter for which they are cited are hereby specifically incorporated by reference in their entireties.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound of the formula:

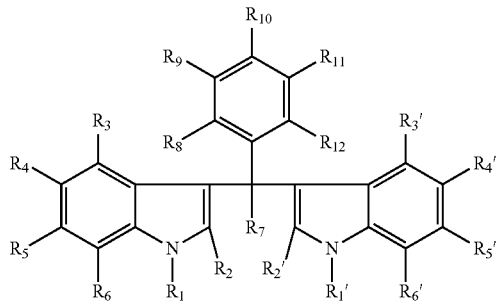

or a salt thereof,
wherein,
$R_1$, and $R_1'$ are each independently selected from the group consisting of hydrogen, a linear alkyl group containing one to about ten carbon atoms, and a branched alkyl group containing one to about ten carbon atoms;
$R_2$ and $R_2'$ are each hydrogen;

$R_3$, $R_4$, $R_5$, $R_6$, $R_3'$, $R_4'$, $R_5'$, and $R_6'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

$R_7$ is selected from the group consisting of hydrogen, a linear alkyl group containing one to about ten carbon atoms, a branched alkyl group containing one to about ten carbon atoms, a cycloalkyl group containing one to about ten carbon atoms, and an aryl group;

$R_8$ is OH;

$R_9$, is selected from the group consisting of H, a fluoro, a chloro, an iodo, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a phenyl, a cyano, and a haloalkoxy group containing one to about ten carbon atoms;

$R_{10}$ is selected from the group consisting of H, a fluoro, a bromo, an iodo, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a phenyl, a cyano, and a haloalkoxy group containing one to about ten carbon atoms;

$R_{11}$ is selected from the group consisting of a linear alkyl group containing one to about ten carbon atoms, a haloalkyl group containing one to about ten carbon atoms, a hydroxyl group, a phenyl, a cyano, and a haloalkoxy group containing one to about ten carbon atoms; and $R_{12}$ is selected from the group consisting of H, a halogen, a linear alkyl group containing one to about ten carbon atoms, a branched alkyl group containing one to about ten carbon atoms, an alkoxy group containing one to about ten carbon atoms, a haloalkyl group containing one to about ten carbon atoms, a hydroxyl group, a nitro group, a phenyl, a cyano, and a haloalkoxy group containing one to about ten carbon atoms.

2. The compound of claim 1, wherein $R_9$, $R_{10}$, $R_{11}$, and $R_{12}$ are independently selected from the group consisting of a $CH_3$, $OCCl_3$, $CF_3$, $OCH_3$, $C_6H_5$, and CN.

3. The compound of claim 1, wherein $R_{10}$ is $OCH_3$.

4. The compound of claim 1, wherein $R_{11}$ is selected from the group consisting of $CH_3$, and $CF_3$.

5. The compound of claim 1 selected from the group consisting of:

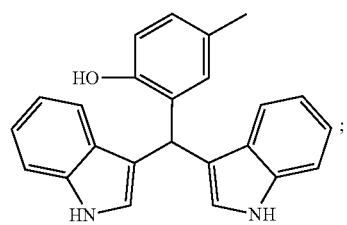

-continued

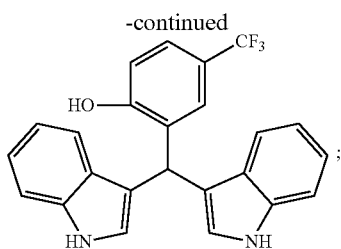

and salts thereof.

6. A compound of the formula:

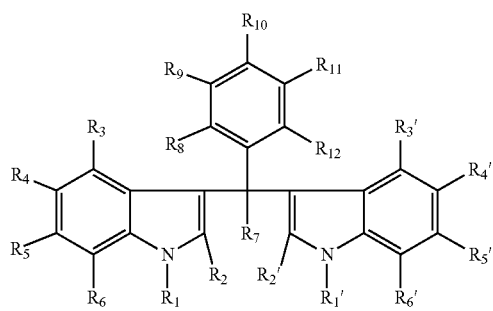

or a salt thereof,
wherein,
$R_1$, and $R_1'$ are each independently selected from the group consisting of hydrogen, a linear alkyl group containing one to about ten carbon atoms, and a branched alkyl group containing one to about ten carbon atoms;
$R_2$ and $R_2'$ are each hydrogen;
$R_3$, $R_5$, $R_6$, $R_3'$, $R_5'$, and $R_6'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;
$R_4$ and $R_4'$ are each independently selected from the group consisting of hydrogen, a fluoro, a chloro, an iodo, a linear alkyl group containing one to about ten carbon atoms, a branched alkyl group containing one to about ten carbon atoms, an alkoxy group containing one to about ten carbon atoms, and a nitro group;
$R_7$ is selected from the group consisting of hydrogen, a linear alkyl group containing one to about ten carbon atoms, a branched alkyl group containing one to about ten carbon atoms, a cycloalkyl group containing one to about ten carbon atoms, and an aryl group;
$R_9$ is OH;
$R_8$ is selected from the group consisting of a fluoro, a bromo, an iodo, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a phenyl, a cyano, and a haloalkoxy group containing one to about ten carbon atoms;
$R_{10}$ is selected from the group consisting of H, a halogen, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a phenyl, a cyano, and a haloalkoxy group containing one to about ten carbon atoms;
$R_{11}$ is selected from the group consisting of H, a halogen, a linear alkyl group containing one to about ten carbon atoms, a branched alkyl group containing one to about ten carbon atoms, an alkoxy group containing one to about ten carbon atoms, a haloalkyl group containing one to about ten carbon atoms, a nitro group, a phenyl, a cyano, and a haloalkoxy group containing one to about ten carbon atoms; and
$R_{12}$ is selected from the group consisting of H, a halogen, a linear alkyl group containing one to about ten carbon atoms, a branched alkyl group containing one to about ten carbon atoms, an alkoxy group containing one to about ten carbon atoms, a haloalkyl group containing one to about ten carbon atoms, a hydroxyl group, a nitro group, a phenyl, a cyano, and a haloalkoxy group containing one to about ten carbon atoms.

7. The compound of claim 6, wherein $R_8$, $R_{10}$, $R_{11}$, and $R_{12}$ are independently selected from the group consisting of a $CH_3$, $OCCl_3$, $CF_3$, t-butyl, $OCH_3$, $C_6H_5$, and CN.

8. The compound of claim 6, wherein $R_8$ is a fluoro, bromo, or iodo.

9. The compound of claim 6 selected from the group consisting of:

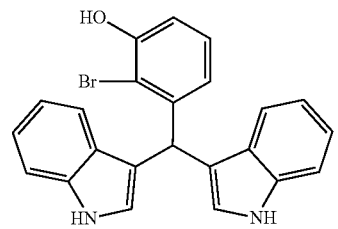 [SMILES: Oc1cccc(C(c2c[nH]c3ccccc23)c2c[nH]c3ccccc23)c1Br]

and salts thereof.

10. A compound of the formula:

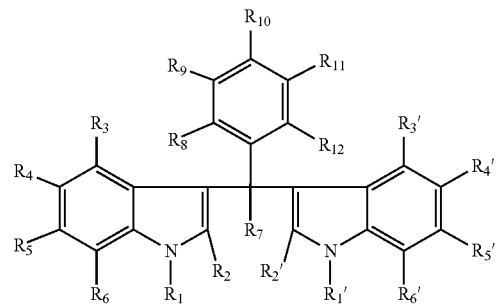

or a salt thereof,
wherein,
$R_1$, and $R_1'$ are each independently selected from the group consisting of hydrogen, a linear alkyl group containing one to about ten carbon atoms, and a branched alkyl group containing one to about ten carbon atoms;
$R_2$ and $R_2'$ are each hydrogen;
$R_3$, $R_5$, $R_6$, $R_3'$, $R_5'$, and $R_6'$ are each independently selected from the group consisting of hydrogen, a halogen, a linear alkyl group containing one to about ten carbon atoms, a branched alkyl group containing one to about ten carbon atoms, an alkoxy group containing one to about ten carbon atoms, and a nitro group;

$R_4$ and $R_4'$ are each independently selected from the group consisting of hydrogen, a fluoro, a chloro, an iodo, a linear alkyl group containing one to about ten carbon atoms, a branched alkyl group containing one to about ten carbon atoms, and a nitro group;

$R_7$ is selected from the group consisting of hydrogen, a linear alkyl group containing one to about ten carbon atoms, a branched alkyl group containing one to about ten carbon atoms, a cycloalkyl group containing one to about ten carbon atoms, and an aryl group;

$R_{10}$ is OH, provided at least one of $R_8$, $R_9$, $R_{11}$, and $R_{12}$ is not hydrogen;

$R_8$ is selected from the group consisting of H, a fluoro, a bromo, an iodo, a branched alkyl group containing one to about ten carbon atoms, an alkoxy group containing one to about ten carbon atoms, a haloalkyl group containing one to about ten carbon atoms, a nitro group, a phenyl, a cyano, and a haloalkoxy group containing one to about ten carbon atoms;

$R_9$ is selected from the group consisting of H, a fluoro, a bromo, an iodo, a branched alkyl group containing one to about ten carbon atoms, a haloalkyl group containing one to about ten carbon atoms, a nitro group, a phenyl, a cyano, and a haloalkoxy group containing one to about ten carbon atoms;

$R_{11}$ is selected from the group consisting of H, a fluoro, a bromo, an iodo, a haloalkyl group containing one to about ten carbon atoms, a nitro group, a phenyl, a cyano, and a haloalkoxy group containing one to about ten carbon atoms; and $R_{12}$ is selected from the group consisting of H, a halogen, a branched alkyl group containing one to about ten carbon atoms, an alkoxy group containing one to about ten carbon atoms, a haloalkyl group containing one to about ten carbon atoms, a nitro group, a phenyl, a cyano, and a haloalkoxy group containing one to about ten carbon atoms.

11. The compound of claim 10, wherein $R_8$, $R_9$, $R_{11}$, and $R_{12}$ are independently selected from the group consisting of a $OCCl_3$, $CF_3$, $C_6H_5$, and CN.

12. The compound of claim 10, wherein $R_9$ is a fluoro, bromo, or iodo, and $R_{11}$ is selected from the group consisting of H, a halogen, and $OCH_3$.

13. The compound of claim 10 selected from the group consisting of:

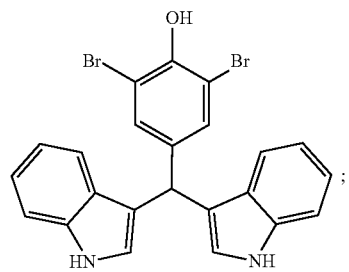 [SMILES: Oc1c(Br)cc(C(c2c[nH]c3ccccc23)c2c[nH]c3ccccc23)cc1Br]

and salts thereof.

14. A pharmaceutical composition, comprising a therapeutically effective amount of a compound according to claim 1, or a salt thereof, and a pharmaceutically acceptable carrier.

15. A method of modulating NR4A1 activity in a cell, comprising administering to the cell a compound according to claim 1, or a salt thereof.

16. The method of claim 15, wherein modulating NR4A1 activity in the cell comprises reducing a level of functional NR4A1 in the cell.

17. The method of claim 15, wherein the cell is a cancer cell.

18. The method of claim 15, wherein the cell is contacted with the compound or pharmaceutical composition in vitro.

19. The method of claim 16, wherein the cell is contacted with the compound or pharmaceutical composition in vivo by administering an effective amount of the compound or pharmaceutical composition to a subject.

20. The method of claim 15, wherein modulating of NR4A1 activity induces down-regulation of a protein selected from the group consisting of β1-integrin, TXNDC5, survivin, EFGR, PAX3-FOX01A, and combinations thereof.

21. The method of claim 15, wherein modulation of NR4A1 activity induces up-regulation of a protein selected from the group consisting of SERPINB5, GADD45α, and combinations thereof.

22. A pharmaceutical composition, comprising a therapeutically effective amount of a compound according to claim 6, or a salt thereof, and a pharmaceutically acceptable carrier.

23. A pharmaceutical composition, comprising a therapeutically effective amount of a compound according to claim 10, or a salt thereof, and a pharmaceutically acceptable carrier.

24. A method of modulating NR4A1 activity in a cell, comprising administering to the cell a compound according to claim 6, or a salt thereof.

25. The method of claim 24, wherein modulating NR4A1 activity in the cell comprises reducing a level of functional NR4A1 in the cell.

26. The method of claim 24, wherein the cell is a cancer cell.

27. The method of claim 24, wherein the cell is contacted with the compound or pharmaceutical composition in vitro.

28. The method of claim 25, wherein the cell is contacted with the compound or pharmaceutical composition in vivo by administering an effective amount of the compound or pharmaceutical composition to a subject.

29. The method of claim 24, wherein modulating NR4A1 activity induces down-regulation of a protein selected from the group consisting of β1-integrin, TXNDC5, survivin, EFGR, PAX3-FOX01A, and combinations thereof.

30. The method of claim 24, wherein modulation of NR4A1 activity induces up-regulation of a protein selected from the group consisting of SERPINB5, GADD45α, and combinations thereof.

31. A method of modulating NR4A1 activity in a cell, comprising administering to the cell a compound according to claim 10, or a salt thereof.

32. The method of claim 31, wherein modulating NR4A1 activity in the cell comprises reducing a level of functional NR4A1 in the cell.

33. The method of claim 31, wherein the cell is a cancer cell.

34. The method of claim 31, wherein the cell is contacted with the compound or pharmaceutical composition in vitro.

35. The method of claim 32, wherein the cell is contacted with the compound or pharmaceutical composition in vivo by administering an effective amount of the compound or pharmaceutical composition to a subject.

36. The method of claim 31, wherein modulating NR4A1 activity induces down-regulation of a protein selected from the group consisting of β1-integrin, TXNDC5, survivin, EFGR, PAX3-FOX01A, and combinations thereof.

37. The method of claim 31, wherein modulation of NR4A1 activity induces up-regulation of a protein selected from the group consisting of SERPINB5, GADD45α, and combinations thereof.

* * * * *